(12) United States Patent
Williams et al.

(10) Patent No.: US 7,711,578 B2
(45) Date of Patent: May 4, 2010

(54) INFLUENCING COMMUNICATIONS AMONG A SOCIAL SUPPORT NETWORK

(75) Inventors: Michael David Williams, Boulder, CO (US); Paul Davoust, Louisville, CO (US); David Taenzer, Aurora, CO (US)

(73) Assignee: Caringfamily, LLC, Louisville, CO (US)

( * ) Notice: Subject to any disclaimer, the term of this patent is extended or adjusted under 35 U.S.C. 154(b) by 1539 days.

(21) Appl. No.: 10/972,000

(22) Filed: Oct. 23, 2004

(65) Prior Publication Data

US 2005/0114759 A1 May 26, 2005

Related U.S. Application Data

(60) Provisional application No. 60/514,172, filed on Oct. 24, 2003.

(51) Int. Cl.
*G06Q 10/00* (2006.01)
*G06Q 50/00* (2006.01)

(52) U.S. Cl. .......................................................... 705/2

(58) Field of Classification Search ...................... 347/2; 358/400, 407, 442, 468, 1.15; 370/352; 379/96; 395/149, 615; 705/2, 4, 27; 707/102
See application file for complete search history.

(56) References Cited

U.S. PATENT DOCUMENTS

| | | | |
|---|---|---|---|
| 5,115,326 A | | 5/1992 | Burgess et al. |
| 5,247,591 A | | 9/1993 | Baran |
| 5,410,646 A | * | 4/1995 | Tondevold et al. .......... 715/207 |
| 5,499,108 A | * | 3/1996 | Cotte et al. ................. 358/400 |
| 5,528,672 A | * | 6/1996 | Wert ....................... 379/93.22 |
| 5,668,990 A | * | 9/1997 | Bajorinas et al. ......... 707/104.1 |
| 6,266,162 B1 | * | 7/2001 | Okamura et al. ............ 358/468 |
| 6,429,946 B1 | * | 8/2002 | Bresnan et al. ............ 358/1.15 |
| 6,442,573 B1 | | 8/2002 | Schiller et al. |
| 6,480,294 B1 | | 11/2002 | Toyoda et al. |
| 6,643,663 B1 | * | 11/2003 | Dabney et al. .............. 707/102 |
| 6,788,672 B1 | * | 9/2004 | Buyukkoc et al. .......... 370/352 |

(Continued)

OTHER PUBLICATIONS

"A Digital Photography Framework Enabling Affective Awareness in Home Communication"; Lieghti & Ichikawa; Aug. 2000.*

(Continued)

*Primary Examiner*—Gerald J. O'Connor
*Assistant Examiner*—John A Pauls
(74) *Attorney, Agent, or Firm*—Hamilton, DeSanctis & Cha LLP

(57) ABSTRACT

Methods and systems are provided for promoting and managing communications among a social support network. According to one embodiment, a communication system includes a closed communication service platform and a hardcopy-based communication appliance. The communication service platform provides a caregroup virtual private network (VPN) through which only registered members of the caregroup, authorized personnel of the communication service platform, processes associated with the communication service platform, and a target of the caregroup are permitted to exchange communications. The hardcopy-based communication appliance is associated with the caregroup VPN and used by the target and is operable to be communicatively coupled to the communication service platform to print inbound communications received from registered members of the caregroup, and to upload to the communication service platform outbound digital representations of annotated pages defining communications to be delivered to one or more members of the caregroup.

41 Claims, 38 Drawing Sheets

U.S. PATENT DOCUMENTS

| | | | |
|---|---|---|---|
| 6,862,348 | B2 | 3/2005 | Toyoda et al. |
| 6,865,594 | B1 | 3/2005 | Belissent |
| 6,885,470 | B1 | 4/2005 | Toyoda et al. |
| 7,023,586 | B2 | 4/2006 | Eguchi |
| 7,136,184 | B2 | 11/2006 | Tonegawa |
| 2002/0075514 | A1* | 6/2002 | Wright et al. .............. 358/1.15 |
| 2002/0075524 | A1* | 6/2002 | Blair et al. ................. 358/442 |
| 2003/0074411 | A1 | 4/2003 | Nale |
| 2003/0193530 | A1* | 10/2003 | Blackman et al. ............. 347/2 |
| 2003/0233411 | A1 | 12/2003 | Parry et al. |
| 2004/0010554 | A1 | 1/2004 | Hall et al. |
| 2004/0024811 | A1 | 2/2004 | Kitada et al. |
| 2004/0254859 | A1* | 12/2004 | Aslanian, Jr. ................ 705/27 |
| 2005/0012965 | A1 | 1/2005 | Bloomfield |
| 2005/0094189 | A1 | 5/2005 | Aoyama et al. |
| 2005/0117527 | A1 | 6/2005 | Williams et al. |
| 2005/0144244 | A1 | 6/2005 | Landesmann |
| 2005/0179943 | A1 | 8/2005 | Silverbrook et al. |
| 2005/0195447 | A1* | 9/2005 | Os ............................ 358/407 |
| 2005/0273498 | A1 | 12/2005 | Sasaki et al. |
| 2006/0190542 | A1 | 8/2006 | Rhoades |
| 2006/0232813 | A1 | 10/2006 | Henry et al. |
| 2006/0250648 | A1 | 11/2006 | Silverbrook et al. |

OTHER PUBLICATIONS

Ceiva, *Sharing Made Easy*, Digital Photo Receiver. 2005; pp. 1-2. http:www.ceiva.com/lmore/dpr/dpr.jsp;jsessionid=aYf7dfILCe_c.

MSN TV: Experience, MSN TV- Microsoft Internet Explorer. http://www.webtv.com/pc/experience/.

EarthLink, Mail Station 250 Product Information FAQ. http://support.earthlink.net/mu/1/psc/img/walkthroughs/other/Cidco_Mailstation; 2005.

Rowe, J.W. et al. "Successful Aging." The MacArthur Foundation Study. Ch.10; 1998.

Faber, A.D. et al., "Social Support and Social Networks: Synthesis and Review." p. 30-72.

Glass, Thomas A., "Population Based Study of Social and Productive Activities as Predictors of Survival Among Elderly Americans- Statistical Data Included." http://findarticles.com/p/articles/mi m0999/is 7208 319/ai 55721107/print; 2004.

Veghese, J. et al., "Leisure Activities and the Risk of Dementia in the Elderly." The New England Journal of Medicine. pp. 2508-2516. 2003;www.nejm.org.

McGrath, Ellen., "Action Strategies: Family Depression." Psychology Today. 2002; https://cms.psyhcologytoday.com/articles/2002.html.

Hall, M. et al., "The Effects of Social Isolation and Loneliness on the Health of Older Women." Department of Community Health Sciences. 1999.

Family Caregiver Alliance ©. "Caregiving and Depression" http://www.caregiver.org/caregiver/jsp/content_node.jsp?nodeid=393.

Beneditctis, T. et al, "Caring for a Person With Alzheimer's Disease or Another Dementia." http://www.helpguide.org/elder/alzheimers_disease_dementias.

Stress. 2001; http://www.reutershealth.com/wellconnected/doc31.html.

Yapko, Michael D., "The Art of Avoiding Depression- Cover Story." Psychology Today. 1997.

"Mental Health: A Report of the Surgeon Central." http://surgeongeneral.gov/library/mentalhealth/chapter5/sec.3.html.

"Depression Research at the National Institute of Mental Health." NIHM National Institute of Mental Health. http://www.nimh.nih.gov/publicat/depresfact.cfm pp. 1-10.

* cited by examiner

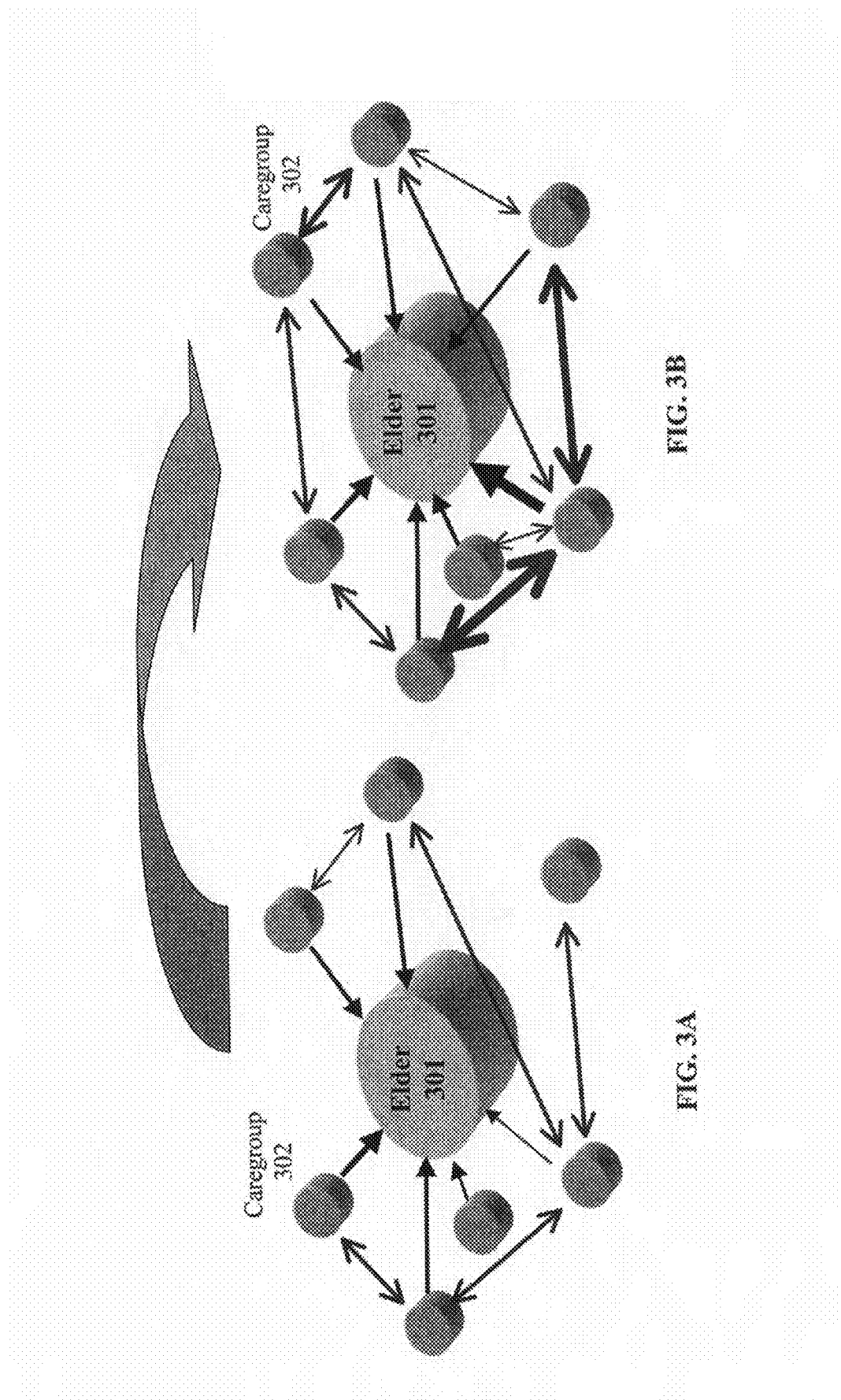

FIG. 22

INFLUENCING COMMUNICATIONS AMONG A SOCIAL SUPPORT NETWORK

This application claims the benefit of Provisional Application No. 60/514,172, filed Oct. 24, 2003 which is hereby incorporated by reference in its entirety.

COPYRIGHT NOTICE

Contained herein is material that is subject to copyright protection. The copyright owner has no objection to the facsimile reproduction of the patent disclosure by any person as it appears in the Patent and Trademark Office patent files or records, but otherwise reserves all rights to the copyright whatsoever. Copyright© 2003-2004 CaringFamily, LLC.

BACKGROUND

1. Field

Embodiments of the present invention generally relate to lifestyle-adapted communications solutions, and in particular, to electronic communications with elders or others disinclined or unable to use personal computers and pseudo computers.

2. Description of the Related Art

Families are frequently located far away from one another, including their aging loved ones. Technology, including personal computers and the Internet, are natural mechanism used by younger members of the family to stay in touch. However, the older a person is, the less likely they are able or interested in owning and using a personal computer, the Internet or email.

The mismatch in the rate of technology adoption between younger and older cohorts of the population makes it increasingly difficult for families to cultivate and sustain the level of communication with their elders that is required to help the elders avoid loneliness and isolation.

Existing mechanisms for connecting non-computer users into the electronic life of their friends and families, such as MSN® TV (formerly WebTV) and EarthLink MailStation™, are plagued with problems that lead to non-acquisition, abandonment or ineffective use of the system chosen. Consequently, alternatives to complicated personal computers and pseudo computers for elders and similarly situated people are needed to provide them with means of communicating via email.

SUMMARY

Methods and systems are described for promoting and managing the quantity, type, quality, and time of delivery of communications among a social support network. According to one embodiment, a hardcopy-based communication appliance includes a scanner, a scan queue, a print queue, and a printer. The scanner is operable to create outbound digital representations of annotated pages one or more portions of which are intended for email delivery to one or more addressees of a caregroup associated with the hardcopy-based email appliance. The scan queue is communicatively coupled to the scanner and operable to buffer accumulated outbound digital representations of annotated pages received from the scanner until the digital representations of annotated pages are directly or indirectly uploaded to a closed communication service which is configured to facilitate and encourage communications among a the members of a caregroup and a target of the caregroup. The closed communication service is operable to process the uploaded digital representations of annotated pages and distribute corresponding resulting email messages to the one or more addressees. The print queue is operable to be communicatively coupled to the closed communication service and to receive inbound digital representations of pages of correspondence received via the closed communication service from members of the caregroup intended for delivery to the target of the caregroup and user of the hardcopy-based email appliance. The printer is communicatively coupled to the print queue and operable to create hard copy output of the inbound digital representations of pages.

According to another embodiment, a communication system is provided to facilitate communications among members of a caregroup and a target of the caregroup. The communication system includes a closed communication service platform and at least one hardcopy-based communication appliance. The closed communication service platform provides a caregroup virtual private network (VPN) through which only registered members of the caregroup, authorized personnel associated with the closed communication service platform, automated processes associated with the closed communication service platform, and a target of the caregroup are permitted to exchange communications to the registered members of the caregroup and the target of the caregroup. The hardcopy-based communication appliance is associated with the caregroup VPN and used by the target and is operable to be communicatively coupled to the closed communication service platform to receive and print inbound communications received from registered members of the caregroup, and to upload to the closed communication service platform outbound digital representations of annotated pages defining communications to be delivered to one or more members of the caregroup via the closed communication service platform.

According to another embodiment, a method of performing content derived addressing is provided. A digital representation of an annotated routing form, including thereon a set of item identification marks, is received from a hardcopy-based communication appliance. The annotated routing form is of a particular form type of a number of predetermined form types. One or more portions of the digital representation of the annotated routing form is intended for email delivery to one or more addressees. The set of item identification marks are read from the digital representation of the annotated routing form and a determination is made regarding the particular form type of the annotated routing form based on the set of item identification marks. One or more characteristics of the annotated routing form, including information regarding a location of an address sector within the annotated routing form, are also determined based on the set of item identification marks. Then, an attempt is made to determine the one or more addressees by processing a portion of the digital representation corresponding to the location of the address sector. A digital representation of a resulting message is composed based at least in part upon the particular form type. Finally, the digital representation of the resulting message is distributed by associating the digital representation of the resulting message with an email message addressed to email accounts associated with each of the one or more addressees.

According to another embodiment automated coaching of the target of a caregroup is performed by a communication service provider. The communication service provider maintains information regarding events of significance to members of a family support network and a target of the family support network and dates associated with the events of significance. Then, responsive to determining a particular event among the events of significance is within a predetermined amount of time, the communication service provider encourages communications among the members of the family support network and the target of the family support network at least in part by delivering a coaching message regarding the particular event to a hardcopy-based communication appliance associated with the family support network and used by the target. The coaching message may include (i) a suggestion regarding an appropriate digital gift that may be sent via the communication service provider by the target to one or more members of the family support network, and (ii) a form depicting representations of one or more images from which the target may select to personalize the suggested digital gift.

According to another embodiment automated coaching of members of a caregroup is performed by a communication service provider. A communication service is provided that is configured to facilitate and encourage communications among members of a caregroup and a target of the caregroup. The target of the caregroup uses a hardcopy-based communication appliance associated with the caregroup to transmit and receive electronic communications via the communication service to or from the members of the caregroup. The communication service captures information regarding digital gifts exchanged among the plurality of members of the caregroup and the target of the caregroup via the communication service and calculates one or more metrics based on the captured information. Based on the one or more metrics, the communication service automatically generates and delivers a coaching message to one or more members of the caregroup. The coaching message includes a suggestion regarding an appropriate digital gift to be sent to the target of the caregroup via the communication service.

Other features of embodiments of the present invention will be apparent from the accompanying drawings and from the detailed description that follows.

BRIEF DESCRIPTION OF THE DRAWINGS

Embodiments of the present invention are illustrated by way of example, and not by way of limitation, in the figures of the accompanying drawings and in which like reference numerals refer to similar elements and in which:

FIG. 3A conceptually illustrates communication flow among a social support network.

FIG. 3B illustrates increased communication with the targeted recipient as well as among the social support network resulting from use of an embodiment of the present invention.

FIG. 22 illustrates a drill down member activity user interface screen listing communications by a specific member of a caregroup according to one embodiment of the present invention.

DETAILED DESCRIPTION

Figure 1:
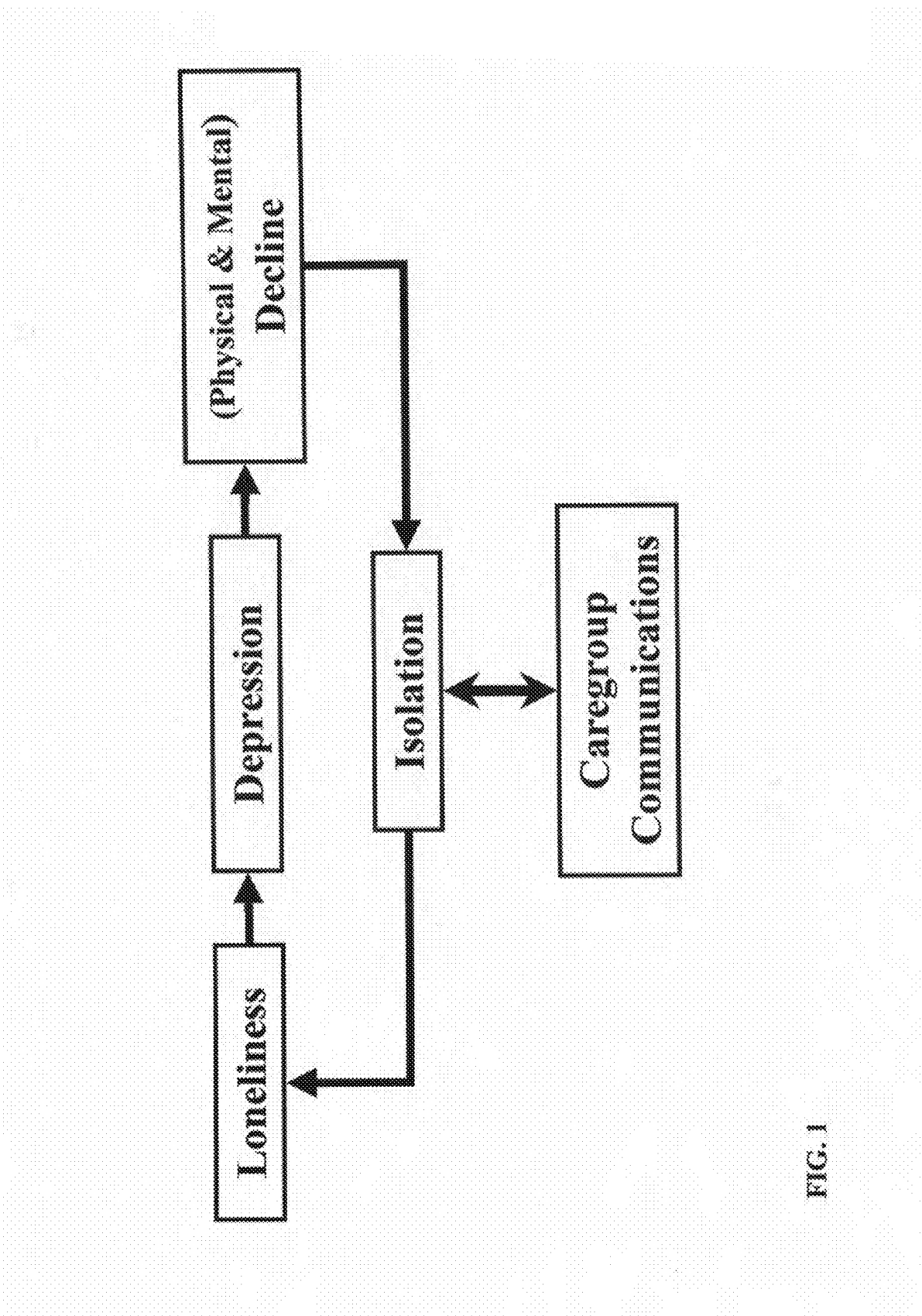
FIG. 1 illustrates a typical cycle of decline that may be experienced by an elder family member.

Methods and systems are described for promoting and managing the quantity, type, quality, and time of delivery of communications among a social support network.

According to one embodiment, a digital mailbox system facilitates receipt and transmission of electronic communications without requiring the end user to have a personal computer. The digital mailbox system includes a novel architecture through which the various interacting parties may use an electronic communication access system that suits their particular needs and technological comfort level thereby adding grace back to the lives of both the elder and their social support network. The novel architecture may provide various tools and applications to promote communications among members of a social support network. For example, according to one embodiment, collaborative and/or individual publishing tools are provided via a website interface to enable collaborative and/or individual development of a daily delivery of a digital publication, such as a newsletter-like publication or the like, for communication to elders by friends, caregivers, family and volunteers. In one embodiment, members of a social support network may select and/or customize content for inclusion in the digital publication from various predefined data streams (e.g., jokes, business news, global news, local news, sports news, puzzles, cartoons, weather, etc.) based upon interests, hobbies and/or cognitive needs (e.g., intellectual stimulation) of the intended recipient. For example, the kinds of material typical of newspaper syndicated features can be provided, such as horoscope, literary quote of the day, "on this day in history", "in your garden today", and the like, selected by the members of the elder's social support network to be appropriate to the elder's interests. In one embodiment, members of a social support network may create or harvest existing family content, such as digitized photos, daily deliveries, digitized art created by children (a/k/a "kid art"), and use it to create various compositions to share among one another and/or the digital mailbox appliance user.

Meanwhile, an elder may make use of a dedicated hardcopy device for sending and receiving electronic communications without the need for a computer, keyboard or mouse. In this manner, the novel architecture acts as a communications transformer by receiving electronic communications in one form from the originator of the communication and outputting the electronic communication in a form suitable for access by an intended recipient thereby facilitating communication to and from those disinclined or unable to use computers, the internet, and/or home networks.

In the following description, numerous specific details are set forth in order to provide a thorough understanding of embodiments of the present invention. It will be apparent, however, to one skilled in the art that embodiments of the present invention may be practiced without some of these specific details. In other instances, well-known structures and devices are shown in block diagram form.

Embodiments of the present invention include various steps, which will be described below. The steps may be performed by hardware components or may be embodied in machine-executable instructions, which may be used to cause a general-purpose or special-purpose processor programmed with the instructions to perform the steps. Alternatively, the steps may be performed by a combination of hardware, software, customer service personnel associated with a communication service provider, caregroup members serving in a customer service role and/or firmware.

Embodiments of the present invention may be provided as a computer program product, which may include a machine-readable medium having stored thereon instructions, which may be used to program a computer (or other electronic devices) to perform a process. The machine-readable medium may include, but is not limited to, floppy diskettes, optical disks, compact disc read-only memories (CD-ROMs), and magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments of the present invention may also be downloaded as a computer program product, wherein the program may be transferred from a remote computer to a requesting computer by way of data signals embodied in a carrier wave or other propagation medium via a communication link (e.g., a modem or network connection).

While according to one embodiment, a digital mailbox system is described as a communication mechanism among families and elders, other embodiments of the digital mailbox system are equally applicable to facilitating electronic communications to and from other groups of individuals, such as developmentally disabled adults. Furthermore, the communications may include unrelated individuals within a common social support network.

While, for convenience, embodiments of the present invention are described with reference to an Application Service Provider (ASP) model, embodiments of the present invention are equally applicable to various other operational models. For example, the systems and methods described herein may be deployed in accordance with a model in which the application is hosted internally by a organization and made accessible to various distributed locations of the organization.

Terminology

Brief definitions of terms used throughout this application are given below.

The phrase "administrating caregiver" generally refers to a member of a caregroup that has certain administrative privileges within the communication system platform. In one embodiment, administrating caregivers have access and permissions to operate a communications service dashboard. Administrating caregivers may have the ability to add or remove members to the caregroup, update family data, manage member viewing, editing and notification permissions, originate coaching prompts, configure many of the VPN and digital mailbox appliance behaviors like time of elder's daily delivery, default printing font, etc. Caregroups may have one or more administrating caregivers.

The term "caregroup" and the phrases "social support network" and "family support network" generally refer to a collection of individuals, including family, friends, caregivers, volunteers and/or service providers, who are registered members of a VPN associated with a user of a communication appliance, such as a digital mailbox appliance. An individual may be a member of multiple caregroups. Members may have different viewing, editing and notification permissions independently associated with each caregroup in which they participate. For example, administrative caregiver permissions described above are one such set of permissions.

The term "carousel" generally refers to a software implemented content buffering mechanism that may receive and store content at one rate and output the stored content at another rate. In one embodiment, one or more carousels are provided by a communication service provider that allow members of a family support network to collect material, such as family photos, items of information, articles, personalized messages, jokes, etc., that will be incorporated over time in a periodic digital publication delivered to an elder. In this manner, a family member can automatically direct selected data feed content to a carousel or manually place original and/or personalized content into a carousel, whenever he or she has time to do so. Then, content from the carousel may be included in various periodic digital publications intended for the elder, such as a daily delivery, when space permits and as needed to provide content in such periodic digital publications. The buffering provided by use of one or more carousels, e.g., photo carousels or personalized content carousels, may be used to smooth the resulting communication over variations in how much time the members of the family support network have to devote to communication or contribution of content or photos. Like photos, items of information from data feeds may also be collected in carousels for use over time. A predetermined or customizable delay may be established before buffered carousel content can be used in the periodic digital publication. This allows members of the family support network to examine, filter, edit, personalize and/or delete unwanted items before they are delivered to the elder. A brief, personal note on a cartoon or joke can add to its affective impact by pointing out a special meaning of the item for the elder or the family.

The phrase "coaching message" generally refers to a message intended to directly or indirectly encourage activity. According to one embodiment coaching messages are messages originated internal to a caregroup VPN either from the communication service provider or a caregroup member or the user of a communication appliance associated with the caregroup VPN that encourages or "prompts" the generation of a new message within the caregroup. For example, a coaching message may directly or indirectly encourage communication with the user(s) of a digital mailbox appliance or encourage the use of new or under used content types available within the communication system platform. Coaching messages may be originated by staff members and/or administrators of the communication service provider, administrating caregivers, or even the user (e.g., an elder) of a digital mailbox appliance. According to one embodiment, various coaching editors are provided within the communication system platform to assist administrating caregiver(s) with the task of creating and sending coaching messages.

In one embodiment, the communication system provider may detect a behavior (or an individual user or a family) and generate a coaching message to one or more family members in response to what is detected. For example, a coaching message may simply encourage a family member to check in by logging onto the family VPN. Certain automatically generated coaching messages may also encourage use of new or under used content types, boost personalization or even add to the members personal data to enhance the overall experience. Other types of coaching messages may supply intellectual stimulation to the elder, recognize family "days of note," encourage an increase in the affective content of correspondence directed to the elder, encourage wider group participation, require specific responses from the elder, and the like.

The terms "connected" or "coupled" and related terms are used in an operational sense and are not necessarily limited to a direct connection or coupling.

The phrase "content derived addressing" generally refers to a process that permits a user of a communication appliance, such as a hardcopy-based email appliance, to send a message to one or more caregroup members without having to specify an email address, phone number or the like. Rather, the message itself contains sufficient information to allow a communication service provider to determine the intended addressee(s). According to one embodiment, with a single press of a button on a hardcopy-based communication appliance an elder may have a message delivered electronically to any caregroup member as part of an email message.

The phrase "digital gift" generally refers to an electronically delivered communication sent by a participant in a social support network or by the individual(s) that are the focus of the social support network. Examples of digital gifts include collages of digital photos, simple text messages, email messages, photo essays, eCards, ready made communications, FamilyWeather, customized/customizable Health and Wellness tips, Kid Art and personalized ready made communications. According to one embodiment, certain ready made digital gifts for delivery to (or from) an elder can be personalized within a few seconds to a few minutes and electronically delivered message (to or from an elder). Digital gifts may be responses to queries, created in digital gift editors, parsed out of standard email formats, or derived from paper forms supplied to the user of a hardcopy communication appliance. Digital gifts often have attractive and emotive decoration and layout. Digital gifts may also contain customized health and wellness status indicators (including, but not limited to mood, sleep, eating, measurements of body fluids or status). According to one embodiment, the printed form of digital gifts that are deliverable to a digital mailbox appliance may be adapted for an elder's personal requirements (e.g., large fonts, high contrast presentation, even adaptation for color blindness).

The phrase "digital mailbox appliance" generally refers to a communication appliance or component configured to be associated with a caregroup VPN through a closed communication service. In one embodiment, a digital mailbox appliance is a hardcopy-based communication appliance that (i) accepts hardcopy input, e.g., paper-based messages, and creates a digital representation of the hardcopy input for electronic delivery, e.g., email delivery of such digital representation or digital gifts based on such digital representation, to one or more members of the caregroup associated with the digital mailbox appliance; and (ii) creates hardcopy output, e.g., paper-based messages, responsive to electronic delivery of communications from caregroup members that are directed to the user of the digital mailbox appliance. According to one embodiment, digital mailbox appliances are remotely maintained by a communication service provider responsive to calls to the communication service provider initiated by the digital mailbox appliances. Depending upon the particular embodiment, a digital mailbox appliance is both simpler than a multifunction printer (MFP) and more functional than an MFP. According to one embodiment, a digital mailbox appliance is simpler than an MFP in that it excludes many MFP features, such as a copier, a universal serial bus (USB) connection to and operation with a PC (or network of PC's), local control of quality (print and scan). According to one embodiment, a digital mailbox appliance is more functional than a MFP in that it connects to and depends on a closed communication service, in that it schedules daily printing, in that it connects to the closed communication service at a time of it's choosing (modem management based on local configuration). It is envisioned that a digital mailbox appliance may be embedded within other consumer devices, such as printers, fax machines, or the like. Also, in embodiments in which hardcopy output is not desired or needed, the digital mailbox appliance may comprise or be part of a cell phone, a personal digital assistant (PDA), or other current or future handheld wireless devices.

The term "eCard" generally refers to an generally refers to an electronically delivered communication in the form of a card, such as a greeting card.

The term "elder" generally refers to an aging family member, such as a parent or grand parent. Typically, the elder is the user of a digital mailbox appliance and a center of focus of a social support network, such as a caregroup, and a target recipient of communication services. An elder might also might be an isolated or disabled family member.

The phrase "ex-officio member" generally refers to a member of a caregroup that has been granted access because of some commercial or support group relationship to the caregroup. Without limitation, examples include the entity or organization that provides the communication service, church groups (e.g., the elder's shut-in committee of their church), an "attending" home care agency, supporting personnel in an assisted living situation, physician, nurse, physician's assistant, insurance provider . . . etc. Ex-officio members typically have access to specialized customer support tools (though a communication service provider customer services website). The tools available and access to information within them may be configured for each caregroup-ex-officio role.

The phrase "helper member" generally refers to a volunteer or commercial caregiver with member status within a caregroup permitted by the administrating caregiver. Examples of helper members include members of a church group, employees of a home care agency, a geriatric consultant, or members of a specialized supporting group (e.g., for Alzheimer's care).

The phrases "in one embodiment," "according to one embodiment," and the like generally mean the particular feature, structure, or characteristic following the phrase is included in at least one embodiment of the present invention, and may be included in more than one embodiment of the present invention. Importantly, such phases do not necessarily refer to the same embodiment.

If the specification states a component or feature "may", "can", "could", or "might" be included or have a characteristic, that particular component or feature is not required to be included or have the characteristic.

The phrase "photo essay" generally refers to a story accompanied by one or more photos. Photo essays are typically about an event or adventure and typically include a paragraph or two about each photo and may include several pages of annotated photos. Examples of photo essays include, without limitation, a story about a trip to Belize by the great granddaughter, stories about diving trips, a photo home tour of a recently purchased condo, pet essays, a retirement party, a classroom party, a Tahiti cruise in planning, participation in a major running race, several local parades, kids climbing a rock wall, and fishing trips. According to one embodiment of the present invention, a photo essay digital gift editor is provided that makes it easy to format and create this kind of content.

The phrase "presentation components" generally refer to editable elements of a digital gift in a digital gift editor.

The term "project" generally refers to multi-day and/or multi-person communication activities, such as the joint creation of an archive of family recipes, an annotated collection of old family photos, a turn taking game (e.g. scrabble, chess, checkers, . . . ) etc.

The term "responsive" includes completely or partially responsive.

The term "scan," when used as a noun, generally refers to a digital representation of a page of correspondence originated at a digital mailbox appliance.

Overview

Social isolation and loneliness are problems for many elders, and such conditions are strongly associated with health problems and reduced feelings of well-being. To address this problem, the methods and systems described herein seek to promote what Liechti and Ichikawa (1999) call *affective awareness*: "a general sense of being in touch with one's family and friends." According to various embodiments of the present invention, communications from a social support network to the individual(s) that are the focus of the social support network are designed to carry not only an informational message but also, more importantly, a message of engagement and caring.

Studies of family communication have shown that the actual content or information exchanged during or in a communication is not the most important aspect of a communication. Rather, it is the expression of interest in the relationship that is of importance as a result of the initiation of a call or sending of a card or email message. Patrick and Metcalf {Patrick, E. and Metcalf, C. (nd) Mediated communication between extended family and friends: A case study. Motorola Labs User Research Report at http://internet2.motlabs.com/user/vmc-study/.} have indicated, "The most striking implication . . . is that communication for shared experience, so important in maintaining distance relationships, is not adequately supported by the communication media available today." Embodiments of the present invention also attempt to address this need.

Meanwhile, not only elders but also family caregivers need support that increased and better communication can provide. Biegel and Schultz (1999), in their introduction to a special issue of Family Relations devoted to family caregivers, note both the prevalence of family caregiving and the burdens it creates. These can include lack of support and assistance from other family members. Picot and Lowell (2001) estimate that there are more than 25 million family caregivers in the United States, and that many feel a significant burden. In the extreme, family caregivers can suffer caregiver burnout (Lee et al. 2001).

Embodiments of the present invention provide methods and systems for creating a virtual private network (VPN) connecting non-computer users with their social support networks who do use computers, camera phones, and/or email appliances. In one embodiment, coaching techniques are employed to influence the quantity, quality, effectiveness and timeliness of electronic communications to and from individuals frequently isolated from family and friends.

Information technology methods and systems are described herein that seek to empower participants in a social support network by simplifying the task of creating and initiating communications. In the context of various embodiments described herein the methods and systems seek to allow family members to provide more effective support to an elder living independently. For example, various communications tools make it easier for family caregivers to provide stimulating and useful information to the elder, helping to sustain health, activity and engagement. Embodiments of the present invention operate as a communication transformer making it possible for family members to communicate with elders using the Internet, without requiring the elders to operate or maintain a computer. It is contemplated that the methods and systems described herein will make it easier for family caregivers to share information and ideas among themselves, and increase the general level of communication within the family generally as well as to and from the elder.

In one embodiment, a proprietary device or set of devices referred to as a "digital mailbox" allows electronic communication with elders. The digital mailbox provides a much simpler user interface for the elder than email or other existing computer applications. The digital mailbox may incorporate features of a fax machine, a photo printer, and a scanner, backed by servers operated by a communication service provider. A member of a social support network is able to generate email or create a digital gift or contribute to a periodic publication which is delivered to the elder as a high-quality hardcopy with no intervention required by the elder via the communication service provider. According to one embodiment, the elder can send correspondence to a member of his/her social support network from his/her digital mailbox by simply placing it on a flat scanner bed and pressing a single button. No typing or dialing is required. As described further below with respect to content derived addressing, addressing the correspondence may accomplished by checking off address information on a routing form provided by the communication service provider and customized for the elder. In another case described below the addressing the correspondence is automatic because the form being used is an explicit reply to a prior communication. Thus, elders can receive and send electronic messages, including images, with no use of a computer and with an extremely simple interface.

According to one embodiment of the present invention, a communication system in which the digital mailbox operates provides an online interface, such as a password protected portion of a web portal, into which participants in a social support group my login. The communication system may include various automated communication tools that allow family members or others in an elder's social support network to send engaging, interesting and useful information to the elder. In view of empirical evidence suggesting elders specifically value predictable communication, versus just getting emails every now and then, embodiments of the present invention facilitate the delivery of information to the elder on a predictable schedule, even when the schedules of the participants in the social support network do not permit such regular communications. The communication system may also provide tools that help family members support one another in their various caregiver roles.

According to one embodiment of the present invention, the digital mailbox appliance provides an unattended printing feature. This unattended printing aspect of the digital mailbox appliance has significant impact. In one embodiment, to receive messages and digital gifts the elder does not have to turn anything on, to login, to use a keyboard, or mouse, or even a TV-like remote control. Gifts and messages simply appear at a regular time of day much as does the mail delivered by the US Post Office.

The communication system may also gather information about the communications exchanged within participating social support networks to allow assessment of the impact of the communications on elders. Impact metrics may then be viewed and analyzed in graphical form by a social support network administrator, such as a family representative or other administrating caregiver. Exemplary impact metrics may include simple counts, assessed value or other measures of effects, communications and gift categories by member, by type, and/or during a specified time period. Effect monitoring may include calculating an assessed value of affective communications, communications that induce intellectual stimulus and/or communications that induce activity. Communication monitoring may include a simple count of digital gifts originated by participants in a social support network and/or the individual(s) that are the focus of the social support network. Digital gift monitoring and analysis may include categorization of digital gifts and tracking of the number of digital gifts in the categories (e.g., collages, simple text messages, email messages, photo essays, ready made communications, and personalized ready made communications).

FIG. 1 illustrates a typical cycle of decline that may be experienced by an elder family member. Isolation may begin in any of a number of ways, e.g., death of a spouse, kids moving away, restrictions to mobility. Isolation usually leads to a sense of loneliness. Loneliness often causes or amplifies depression (clinical or sub-clinical). Depression is strongly linked with both physical and mental decline. Physical and/or mental decline may lead to further loss of mobility and/or less frequent interactions with others. This in turn increases isolation and the downward spiral continues. Family communications can interrupt the isolation slowing and even reversing the decline.

Figure 2A:
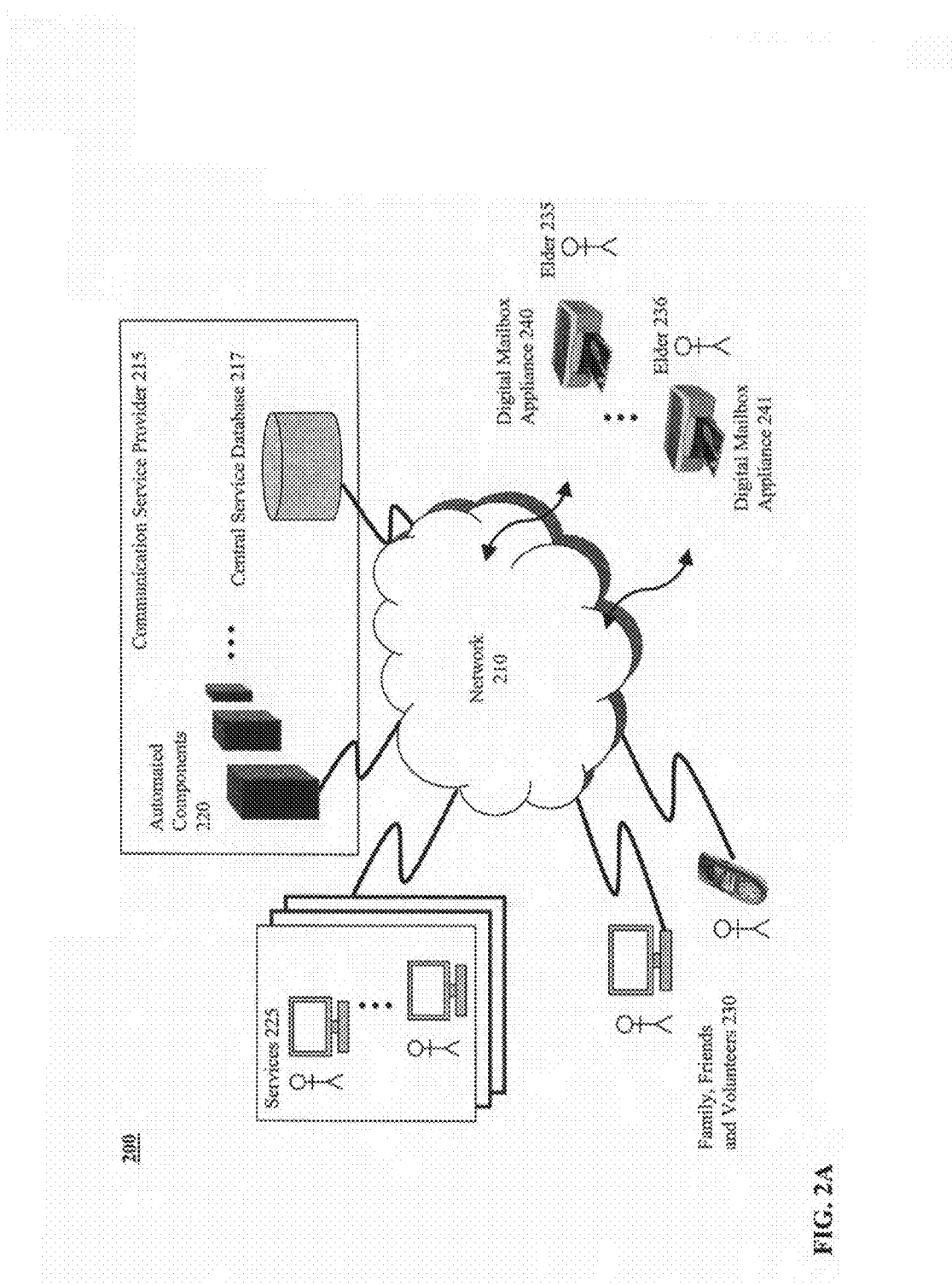
FIG. 2A is a block diagram conceptually illustrating a high-level architectural view of a communications system in accordance with one embodiment of the present invention.

FIG. 2A is a block diagram conceptually illustrating a high-level architectural view of a communications system 200 in accordance with one embodiment of the present invention. In the embodiment depicted, the communications system includes a communication service provider 215, services 225, digital mailbox appliances 240 and 241 used by elders 235 and 236, respectively and family, friends, and volunteers 230 communicatively coupled through a network 210.

According to one embodiment, the network 140 is a public communications network, such as the Internet; however, it is contemplated that smaller scale communication systems may be implemented within a private communications network, such as a local area network (LAN) (e.g., an Ethernet LAN or a token ring LAN), an Intranet, an Extranet, a wide area network (WAN) comprising multiple inter-linked LANs and/or leased lines or any other communication structure designed to carry data between a plurality of computers associated with a particular enterprise or organization.

While for simplicity, in this example, only two elders 235 and 236 are discussed as being subscribers of communication service provider 215, it is to be understood that the communications service provider 215 may scale to serve any number of elders and associated caregroup members. Additionally, as mentioned above, while various embodiments of the present invention are described in the context of the communication service provider 215 serving as a communications transformer between elders and their family and friends, the concepts described herein are broadly applicable to other social support networks caring for or looking after one or more individuals that are cognitively or physically unable to use a computer system or simply disinclined to use a computer system to send and receive email.

Furthermore, for sake of illustration, embodiments of the present invention are described in the context of a configuration of a communication system in which there is a one-to-one-to-one relationship between digital mailbox appliances, elders, and caregroups and messages are exchanged among the elder associated with a particular digital mailbox appliance and the corresponding caregroup members. However, it is contemplated that multiple individuals, such as an elder dyad (say man and wife), could share a digital mailbox appliance and caregroup. Additionally, digital mailbox appliance to digital mailbox appliance messages may be sent in scenarios in which an elder using one digital mailbox appliance is a member of the caregroup of another elder using another digital mailbox appliance.

In one embodiment, elders 235 and 236 are able to participate in exchanges of messages with their families and friends via digital mailbox appliances 240 and 241 using familiar paper-based communications. The digital mailbox appliances 240 and 241 preferably reside in the elders' residence and connect to the communication service provider 215 via a residential phone line. According to one embodiment the digital mailbox appliances 240 and 241 comprise multi-function photo quality printers (e.g., color or grayscale, inkjet or laser) with flatbed scanners and modems and are operated by local software configured and managed remotely by the communication service provider 215. To accommodate single phone line residences, the digital mailbox appliances 240 and 241 may be specifically designed to effectively share a single phone line with the elders' normal phone usage. In alternative embodiments, the digital mailbox appliances 240 and 241 may be configured to interface with the communication service provider through digital subscriber line (DSL) service, cable modem, integrated services digital network (ISDN) service, or other broadband or narrow band service. In alternative embodiments, the digital mailbox appliances 240 and 241 may include one or more other forms of output devices in addition to or instead of a printer, such as a video monitor or a text-to-speech conversion apparatus.

In the present example, elders 235 and 236 represent individuals participating in and having access to a communication service provided by the communication service provider 215. While the participants or users of the digital mailbox appliances, e.g., elders 235 and 236, are the focus of the communication service, typically, the subscriber to the communication service (i.e., the payer) is one or more members of a participant's caregroup.

The communication service may include communications transformation and management services to facilitate electronic communications among the participants and their social support networks. For example, as described in further detail below, members of the elders' social support networks may access and use tools and templates for formatting and creating various types of digital gifts and for creating collaborative publications for the elders 235 and 236.

According to the present example, the communication service provider 215 comprises automated components 220 and a central database 217. Automated components 220 may include multiple websites supporting family members, customer service operations for the communication service provider 215, research team service tools, coaching and communications management systems and tools, mailbox configuration management systems, publication and delivery systems, email services customized to caregroup management and digital mailbox appliance publication services, etc. The central database 217 is a central repository for all systems programs and manages data on caregroups, elders, individual members, family photos, digital gifts and their component parts, specific delivery information for each communication, digital mailbox log histories, configuration information, etc. Further details regarding the hardware and software infrastructure of an exemplary communication service provider are provided below.

Services 225 may represent pre-screened service providers selected to meet various needs of the subscriber base (e.g., digital mailbox appliance users) of the communication service provider 215.

In one embodiment, a unique identifier is assigned to each digital mailbox appliance that is permanently stored in a non-volatile memory of the digital mailbox appliance. This digital mailbox appliance identifier may be used for initial connection and registration of the end user, e.g., elder, into their supporting VPN. The digital mailbox appliance identifier may also be used to validate the digital mailbox appliance each time it attempts to connects to the communication service provider 215. Further, the identifier permits the elder to move their digital mailbox appliance to a new location (e.g., a convalescent home, a relative's home, etc.) and maintain seamless service. The digital mailbox appliance identifier may also be used by the communication service provider 215 to facilitate interpretation of problem reports, logged events, etc.

Figure 2B:
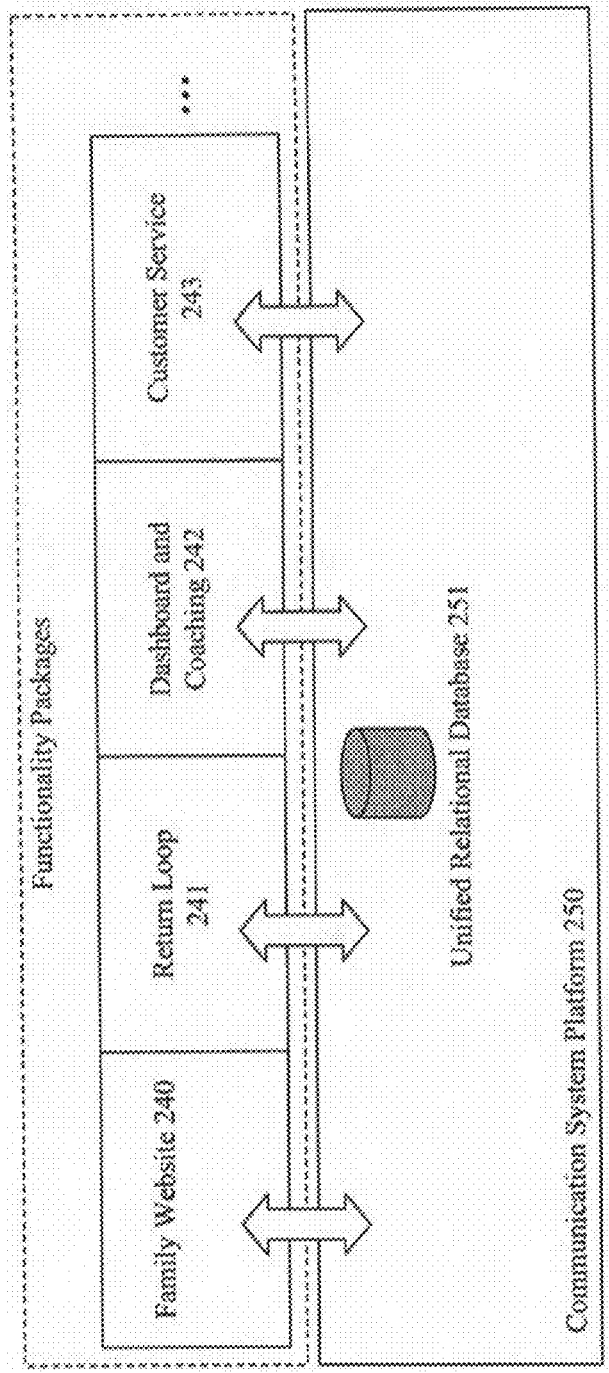
FIG. 2B is a block diagram conceptually illustrating various collections of functionality packages and their relation to the communication system platform according to one embodiment of the present invention.

FIG. 2B is a block diagram conceptually illustrating various collections of functionality packages 240-243 and their relation to the communication system platform 250 according to one embodiment of the present invention. In the example depicted, the communication system platform 250 includes a unified relational database 251, the digital mailbox appliances associated with particular elder(s) and corresponding caregroup, a publication and distribution server, customer service personnel, and basic web and email services.

In the present example, for purposes of explanation, the digital mailbox service is described as a number of functionality packages 240-243. Each functionality package 240-243 interacts with the unified relational database 251 of the communication service platform. These functionality packages 240-243 provide services variously to family members, elders, communication service provider personnel and ex-officio caregroup members. The services provided typically have some automated components, some specialized website elements for family members and/or customer support personnel of the communication service provider, as well as some specialized elements of the unified relational database 251. Some software and system components are common to more than one functionality package. For example, digital mailbox logging may be used by several of the functionality packages in slightly different ways. Similarly, an email parsing component may be utilized by multiple functionality packages.

According to one embodiment, a family website functionality package 240 is unique for each caregroup and thereby supports individual family VPNs into which members login. Because the digital mailbox appliances are associated with and embedded in a family VPN, the communication service provider is able to prevent SPAM and viruses from invading the elder's environment. While, due to the appliance environment, elders are largely immune to viruses, the communication service provider may whitelist (e.g., expressly define) all potential senders for the elder and automatically filter all deliveries for viruses. According to one embodiment, whitelist-based filtering involves creating a list of addresses of people that are authorized to send communications to the user of the digital mailbox appliance and caregroup members and filtering communications that are not on the authorized list. Meanwhile, because all web pages delivered to the elder go through custom rendering engines and because the digital mailbox appliance is not a standard PC using a standard operating system, worms are prevented from accessing the elder's side of the communication system.

The primary purpose of the family website service is to facilitate communication between family members and the target elder(s). The family website functionality package 240 interacts with a distribution server (not shown) of the communication system platform to deliver family communications to the elder's digital mailbox appliance. The family website functionality package 240 also facilitates the creation of communications by providing various digital gift editors that simplify the task of customization and personalization, suggesting ready made digital gifts, and allowing members to view what other members have sent to the elder.

A return loop functionality package 241 manages traffic sent from the digital mailbox appliances. Missives received from a digital mailbox appliance are typically originated by the elder. However, it is contemplated that various support and service personnel working in the elder's environment may occasionally send communications via the elder's digital mailbox appliance. According to one embodiment, the return loop functionality package 241 includes dispatcher workbench websites for both family dispatcher volunteers and customer service personnel of the communication service provider. Further discussion of manual and automated dispatching of traffic sent from digital mailbox appliances is provided below.

A dashboard and coaching functionality package 242 performs communications assessment, monitoring, and provides the coaching environment used to influence and manage electronic family communications to and from the elder through the communication system platform 250. The dashboard and coaching functionality package 242 may include various monitoring charts, tables, and instruments described further below. The dashboard and coaching functionality package 242 may also provide a collection of coaching editors to help administrating caregiver(s) in creating and sending coaching messages (also called "prompts") to other caregroup members and/or the target elder(s).

A customer service functionality package 243 serves as an access point for customer support personnel of the communication service provider. The customer service functionality package 243 may also provide a range of traditional services to the communication service platform 250, other services, or other of the functionality packages 240-242. For example, in one embodiment, one or more of online (or phone) purchase and registration, testing, responding to bugs, recovering data, identifying the frequency of problems, and repairing communications flow problems may be supported via the customer service functionality package 243.

Additional custom interfaces (not shown) for services can also be provided to restricted sets of the database permitting ex-officio membership (as granted by the family) to home care agencies, geriatric consultants, assisted living personnel, support groups, etc.

One or more research service interface functionality packages (not shown) may also be provided. Such specialized service interfaces may be used to support specific scientific research projects funded by the government or foundations. The various different research service interface functionality packages may create specialized links into the VPNs associated with families supporting elders in various circumstances (e.g. Alzheimer's dyads, elder alone, assisted living, etc.). The interfaces may limit access in accordance with the corresponding research plan. For example, some interfaces may allow access to detailed data on a subset of the caregroups represented within the communication service provider's subscriber base while limiting access to statistical data regarding other caregroups.

A digital mailbox operation and management functionality package (not shown) may serve as a network operations center (NOC) for the communication service provider's collection of VPNs. According to one embodiment, the digital mailbox operation and management functionality package may include web-based tools for the communication service provider's customer service personnel and various software programs to remotely monitor and/or manage the digital mailbox appliances' (ink levels, logging, mailbox behavior configuration, software updates, heartbeat, error and error recovery . . . etc.). The digital mailbox operation and management functionality package also includes software components that support final stage publication and delivery of family digital gifts and missives originated by the elder.

FIG. 3A and FIG. 3B illustrate before and after communication flows, respectively, among a social support network based on the findings of various pilot studies. While communications are complex and varied (there is no single channel, there is no simple uniform effect on participants), increases in communication between the elder and family members, as shown by heavier arrows, and also increased or newly-established communication among other family members have been observed. Notably, communications increases to and from the elder through the communication service provider as well as outside the service (e.g., phone). Communication also increases among members of the social support network (again within the service provided by the communication service provider as well as outside). Within the context of family communications sending a communication often provokes one or more responses, which in turn create more responses establishing complex dialogs binding families into a shared experience.

Figure 4:
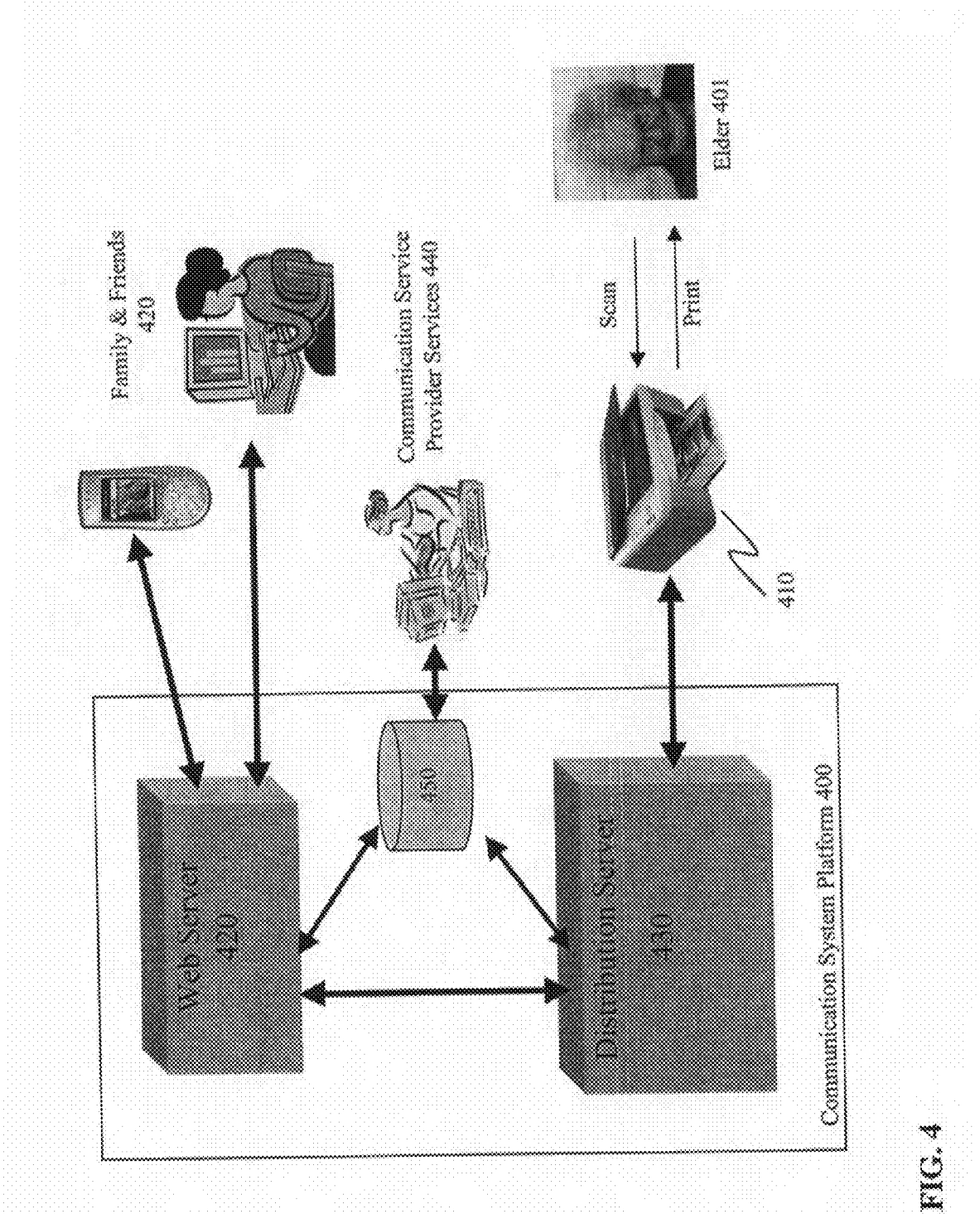
FIG. 4 is a block diagram conceptually illustrating a communication architecture according to one embodiment of the present invention.

FIG. 4 is a block diagram conceptually illustrating a communication architecture of a communication system platform 400 according to one embodiment of the present invention. This highly simplified description of major conceptual blocks is intended primarily to illustrate the major flows of information from the caregroup members, e.g., family and friends 420, using various appliances to the elder 401 (through the elder's digital mailbox appliance 410) with the communication service provider and other service personal participating as necessary.

In this simplified illustration, the communication system platform 400 provides interfaces for the elder 401 via digital mailbox appliance 410, family and friends 420 of the elder 401, and communication service provider services 440. In this example, the communication service provider may provide various services, such as monitoring, tracking, and analysis of family communications, to support the administrating caregiver in his/her coaching role.

Given the personal and potentially sensitive nature of communications that are contemplated to be exchanged through the communication system platform 400, participants should expect any entity serving in the capacity of a communication service provider to implement and enforce strict privacy policies. For example, in one embodiment the closed nature of the communication service seeks to protect families and their elders from the familiar risks of Internet communication including spam, viruses, spyware, unsolicited commercial offers, and more. While the communication service provider may collect personal information during the course of use by members of caregroups and the targets of the caregroups with the goal of establishing and maintaining caregroup VPNs, this information may be used to protect and empower the participants in various ways, including limiting access to caregroup VPNs, allowing families to share the caregiving load, and prohibiting advertising and/or solicitation by external commercial entities. In one embodiment, admission to caregroups may be limited to family, friends, and other approved caregivers and/or service providers designated by the elder and the family. Furthermore, privileges within the caregroup may be defined by the elder and/or an administrating caregiver. By way of the closed communication service enabling wide, but exclusive, membership in an elder's caregroup and by aggregating information about the types and frequency of communication within these groups, families are empowered to share the caregiving load and are able to work together in new and more efficient, effective ways to support their elders.

According to the present example, the communication system platform 400 provides a communications transformer that emphasizes familiar paper output for elders and leverages the increasing use of computer technology by their families and friends. In this manner, a solution is provided to address the disparate technologies used for communication and styles of communication among various members of a family support network. Each member of the family support network may use a system adapted to their individual lifestyles. As will be described further below, the communication system platform 400 exploits the power of collaboration and community to share the load of creating personalized communications for aging loved ones.

The communication system platform 400 includes a web server 420, a distribution server 430, and a central service database 450. Participating family members may send emails, digital gifts, or camera phone messages to the elder 401 through traditional email and/or the web server 420, which hosts the family VPN websites. Communications, such as email, Multimedia Messaging Service (MMS) messages from camera phones, and digital gifts are stored in the central service database 450 and forwarded to the distribution server 430 for processing into an appropriate printable format and stored for delivery to the elder's digital mailbox appliance 410 by the communication service provider services 440, which delivery may be automated or may include manual intervention by a customer service representative or an administrating caregiver as described further below.

According to one embodiment, the digital mailbox appliance 410, which would typically reside in the elders' home, has two functions. It provides for unattended printing (e.g., periodic digital publications to which various members of the caregroup have contributed) and permits the elder to scan self addressing content for delivery as email to one or more of the members of her caregroup.

According to one embodiment, the quality of the hardcopy output of the digital mailbox appliance 410 and the color scan input is such that color snapshots can readily be incorporated into the digital gifts sent to or from the elder 401, respectively.

In a preferred embodiment, the digital mailbox appliance 410 comprises a new multi-function device priced at about $250 (or less) retail and provides ≧300 dpi color printing, flatbed scanning, scheduled polling, a large status display, a single-button control panel, a hidden auxiliary control panel, a high-output speaker, a proprietary communications interface, physical forms storage, remote connectivity over an analog phone line, as well as remote monitoring and management.

Design trade-offs for a digital mailbox appliance 410 targeted for elders and similarly situated individuals are atypical. For example, print speed is not perceived to be a key issue. However, the speed of the communications link is perceived to be relatively important. In one embodiment, personal printing features, such as low-cost inkjet technology are mixed with enterprise features, such as remote monitoring and management. According to one embodiment, copying will not be offered despite the presence of all of the necessary hardware to provide copying capabilities. In one embodiment, the digital mailbox appliance 410 includes no standard computer interface and functions solely as a standalone appliance rather than as a computer peripheral.

According to various embodiments of the present invention, instead of the frustration of a personal computer, a digital mailbox appliance provides to elders or other digital mailbox appliance users the welcome familiarity of simple paper-based communications. The elders' digital mail arrives automatically. Deliveries to the digital mailbox appliance 410 may be configured to occur every day on a pre-set schedule. To send a handwritten note seniors press a single button to initiate scanning and delivery of the note. Various benefits of the digital mailbox appliance 410 include its simplicity, security, robustness, low-maintenance, remote supportability by the family or communication service provider personnel. Additionally, paper-based communications having configurable font size tailored to the recipient accommodates visual impairments. Because the printed output can be customized on the level of an individual digital mailbox user numerous needs and preferences can be accommodated (consider color-blindness, contrast requirements, . . . etc.).

Note that in this description, in order to facilitate explanation, the web server 420, distribution server 430, central service database 450 and communication service provider services 440 are generally discussed as if they each reside on or are part of a single computer system. However, it is contemplated that such servers, databases and services may each actually comprise multiple physical and/or logical devices connected in a distributed architecture. Additionally, in alternative embodiments, the functions performed and the data stored may be consolidated and/or distributed differently than as described.

Figure 5:
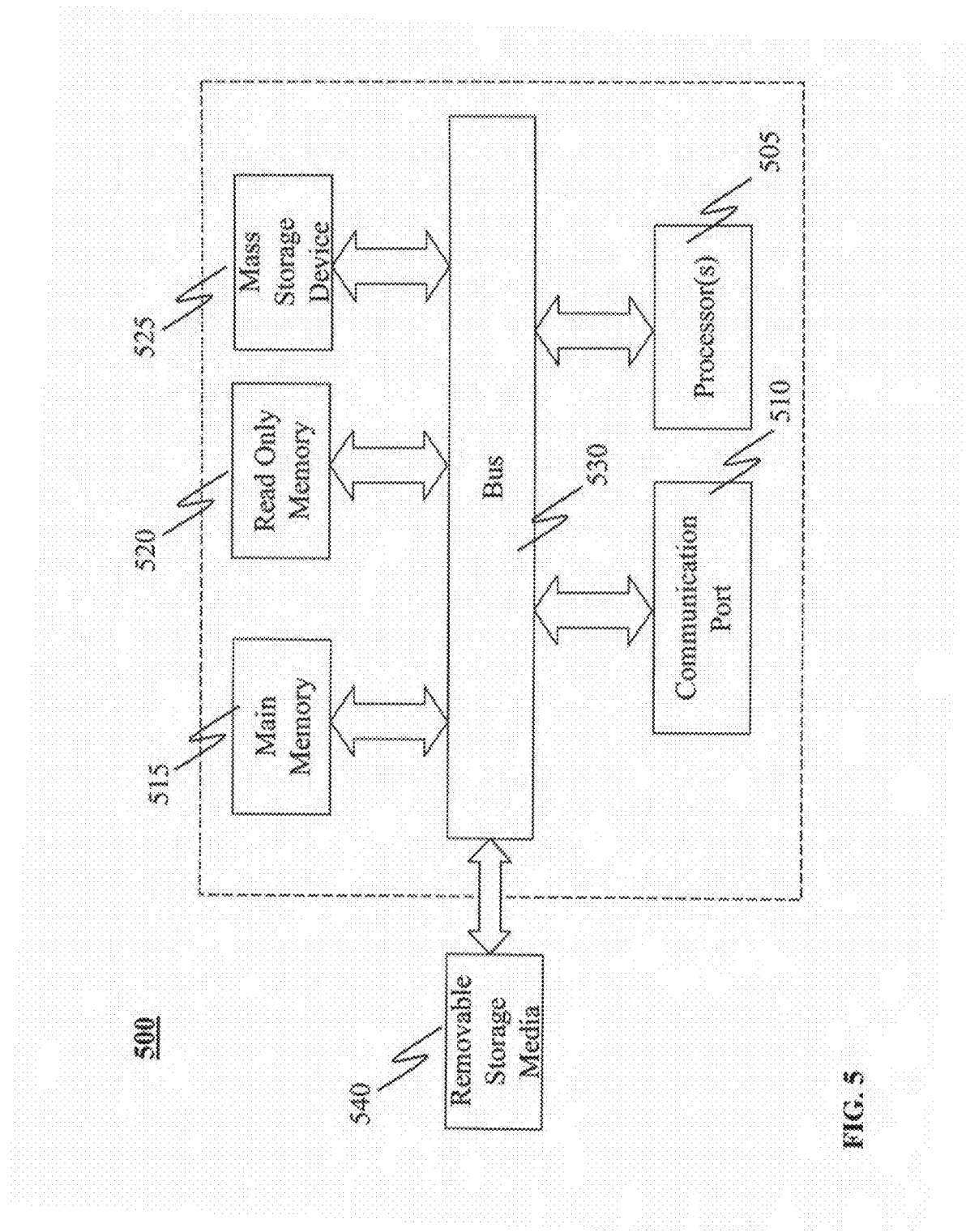
FIG. 5 is an example of a computer system with which embodiments of the present invention may be utilized.

FIG. 5 is an example of a computer system 500 with which embodiments of the present invention may be utilized. The computer system 500 may represent a web server, presentation server, a distribution server and/or other computer systems involved in the communication system platform. According to FIG. 5, the computer system 500 includes one or more processors 505, one or more communication ports 510, main memory 515, read only memory 520, mass storage 525, a bus 530, and removable storage media 540.

The processor(s) 505 may be Intel® Itanium® or Itanium 2® processor(s), AMD® Opteron® or Athlon MP® processor(s) or other processors known in the art. Communication port(s) 510 can be any of an RS-232 port for use with a modem based dialup connection, a 10/100 Ethernet port, or a Gigabit port using copper or fiber. Communication port(s) 510 may be chosen depending on the network environment in which the computer system 500 operates, such as the Internet, a Local Area Network (LAN), Wide Area Network (WAN), or any network to which the computer system 500 connects.

Main memory 515 may be Random Access Memory (RAM), or any other dynamic storage device(s) commonly known in the art.

Read only memory 520 may be any static storage device(s) such as Programmable Read Only Memory (PROM) chips for storing static information such as instructions for processors 505.

Mass storage 525 may be used to store information and instructions. For example, hard disks such as the Adaptec® family of SCSI drives, an optical disc, an array of disks such as RAID, such as the Adaptec family of RAID drives, or any other mass storage devices may be used.

Bus 530 communicatively couples processor(s) 505 with the other memory, storage and communication blocks. Bus 530 may be a PCI/PCI-X or SCSI based system bus depending on the storage devices used.

Optional removable storage media 540 may be any kind of external hard-drives, floppy drives, IOMEGA® Zip Drives, Compact Disc—Read Only Memory (CD-ROM), Compact Disc—Re-Writable (CD-RW), Digital Video Disk—Read Only Memory (DVD-ROM).

Figure 6A:
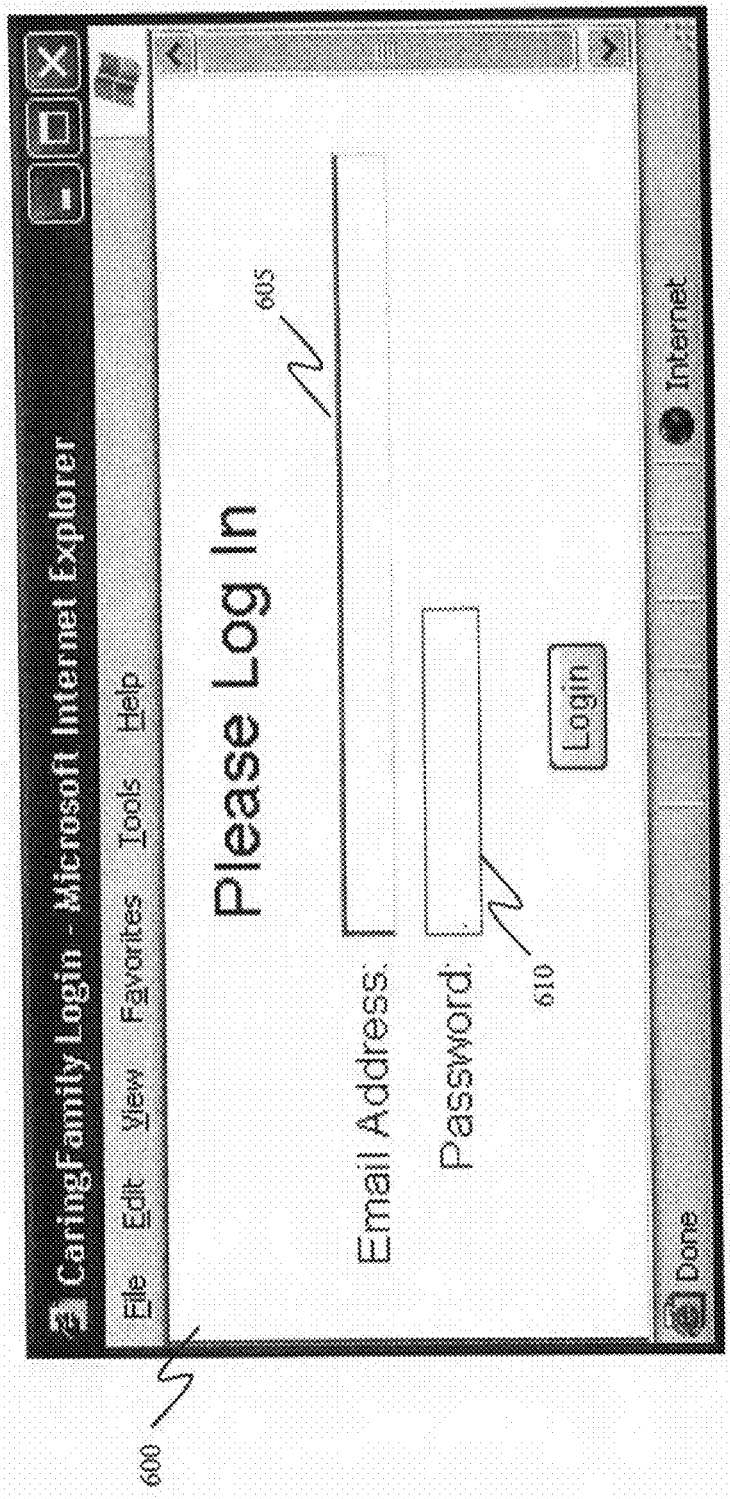
FIG. 6A illustrates a member login user interface screen according to one embodiment of the present invention.

FIG. 6A illustrates a member login user interface screen 600 according to one embodiment of the present invention. In this example depicted, if an individual is a member of only a single caregroup, the member logs in to the caregroup VPN by entering his/her email address into an email address field 605 and entering his/her password into a password field 610 of the member login user interface screen 600. If, however, the individual is a member of multiple caregroups, then a caregroup selection user interface screen, such as that illustrated in FIG. 6B may be used to solicit information regarding the desired caregroup VPN into which the member would like to login.

Figure 6B:
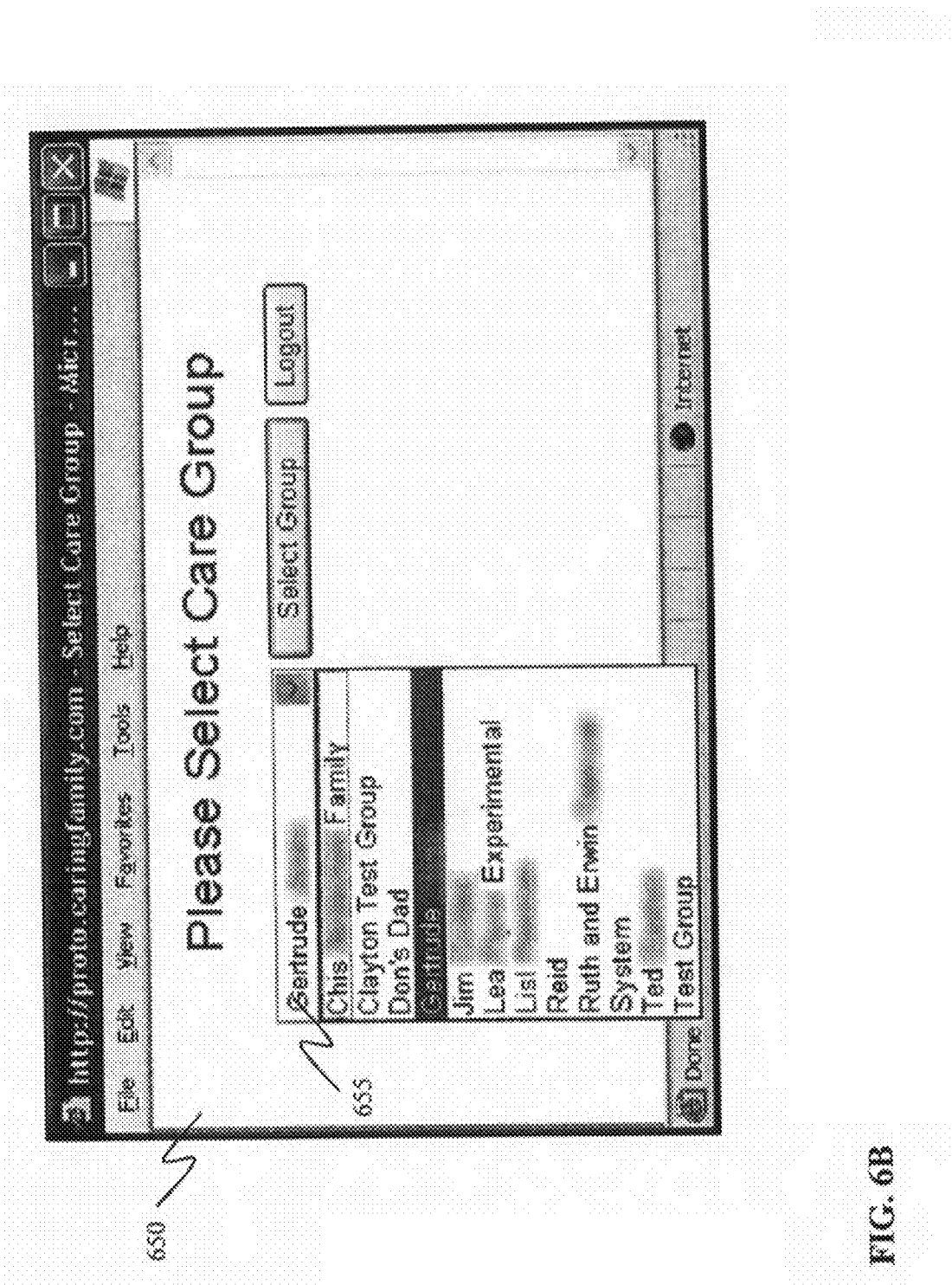
FIG. 6B illustrates a caregroup selection user interface screen according to one embodiment of the present invention.

FIG. 6B illustrates a caregroup selection user interface screen according to one embodiment of the present invention in which the user is a member of multiple caregroups. According to one embodiment of the present invention, each digital mailbox appliance has one and only one caregroup. Caregroup members are typically family and friends of the elder using the digital mailbox appliance. After logging in via a member login user interface screen, such as that illustrated in FIG. 6A, if the member participates in more than one caregroup they are asked to select the caregroup VPN into which they want to be placed.

Figure 7:
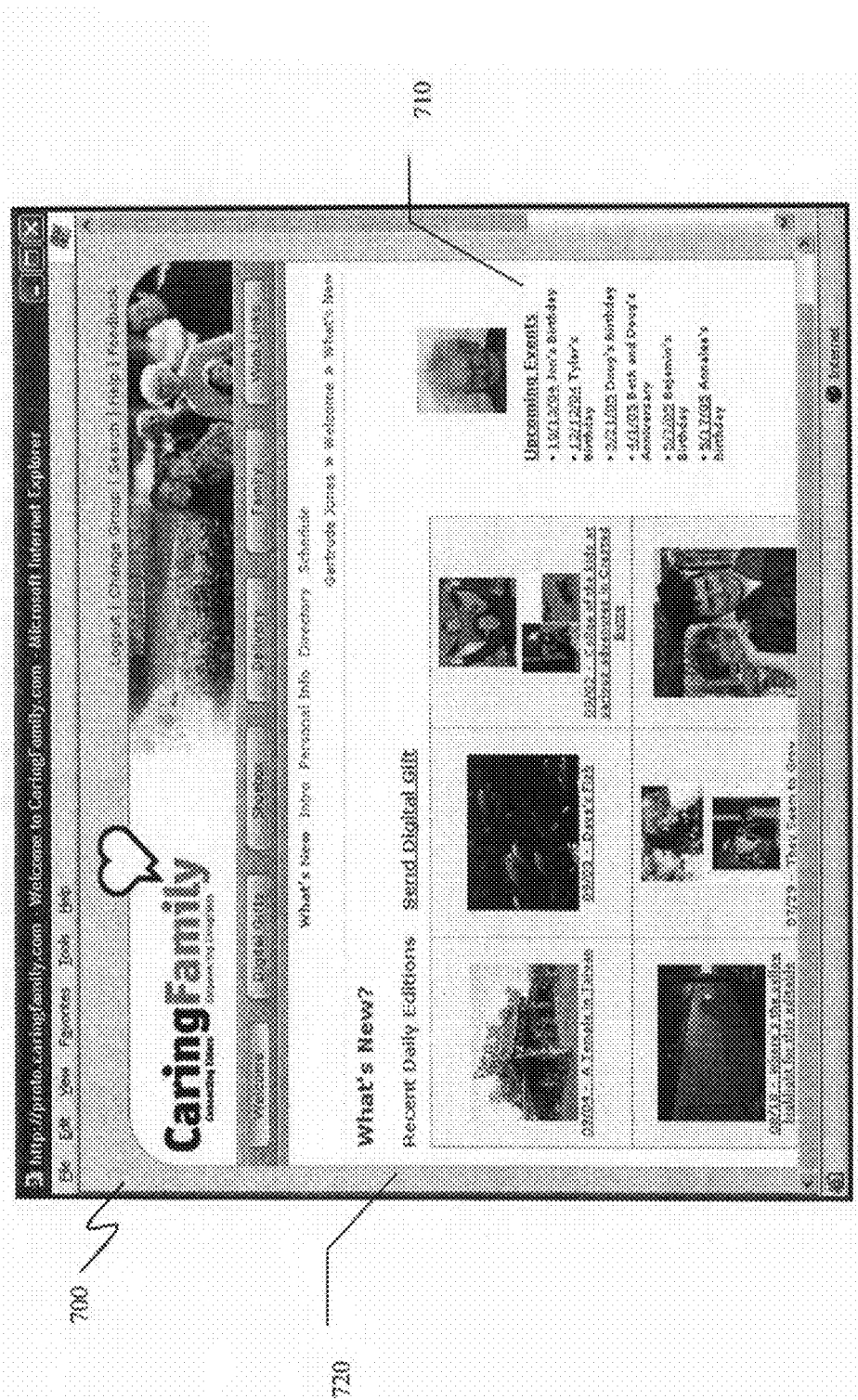
FIG. 7 illustrates a caregroup home page user interface screen according to one embodiment of the present invention.

FIG. 7 illustrates a caregroup home page user interface screen 700 according to one embodiment of the present invention. According to one embodiment, once logged in members work within a website that encapsulates the VPN of the social support network of a particular elder with a digital mailbox appliance. In the present example, the home page includes a list 710 of various upcoming events, such as birth dates of various family members. The home page also includes an area 720 depicting thumbnail representations of recent "Daily Deliveries" thereby allowing members to review digital gifts that have been sent to the elder.

Figure 8:
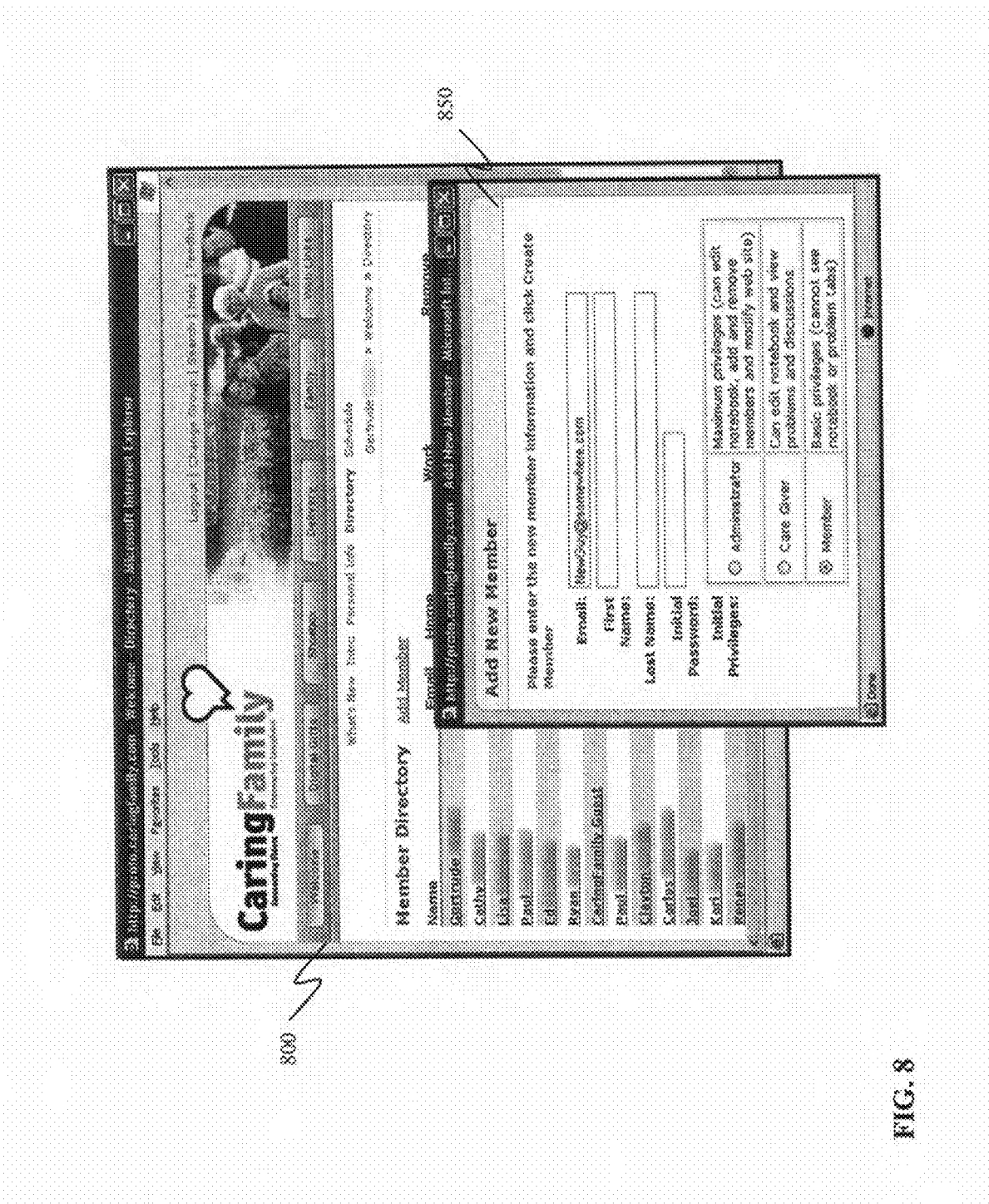
FIG. 8 illustrates a member registration user interface screen according to one embodiment of the present invention used by caregroup administrators to register a new member to their caregroup.

FIG. 8 illustrates a member registration user interface screen 800 according to one embodiment of the present invention used by caregroup administrators to register a new member to their caregroup. In one embodiment, an administrating caregiver is provided with the ability to register new caregroup members. The administrating caregiver(s) have administrative privileges and may therefore add members through a pop-up editor in the website as shown by member registration user interface screen 850.

If the communication service provider already has information regarding the member by way of the member being part of another caregroup, for example, then the member is simply added to this caregroup with all their existing directory information. If not, additional initial information is requested. According to one embodiment, new members are sent an email requesting that they opt-in and directing them to a registration page and further training (as appropriate).

In the present example, to add a new member to a family support network, the administrating caregiver navigates to a member directory user interface screen 800, selects the "Add Member" link, and then enters the new member information on the member registration user interface screen 850.

In alternative embodiments, phone to a customer service representative of the communications service provider or to an automated telephone system or other web interfaces may be provided to the administrating caregiver to add new caregroup members. Furthermore, administrating caregivers may act as recruiters and provide a list of desired members to the communication service provider. Subsequently, the communication service provider may send an email introduction to each of the individuals listed by the administrating caregiver and allow the individual family members to opt-in.

Figure 9:
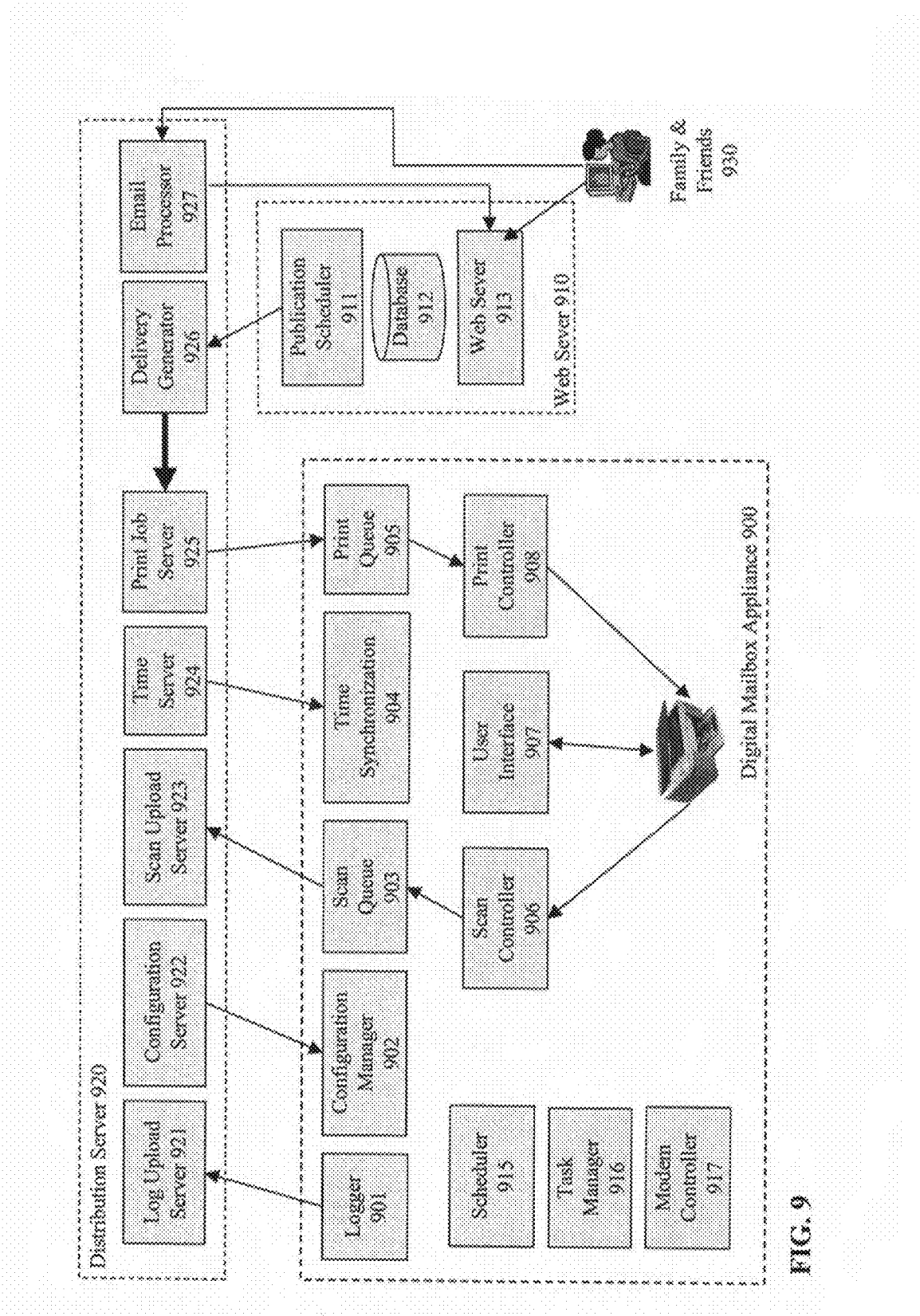
FIG. 9 is a software architecture block diagram conceptually illustrating application-level software components of the distribution server, web server, and internal components of the digital mailbox according to one embodiment of the present invention.

FIG. 9 is a software architecture block diagram conceptually illustrating application-level software components of a distribution server 920, a web server 910, and internal components of a digital mailbox appliance 900 according to one embodiment of the present invention.

According to the software architecture depicted, the web server 910 includes a publication scheduler 911 that gathers up digital gifts and publishes them to the delivery generator 926 based on a schedule configurable by the administrating caregiver(s), a centralized database 912 holding all caregroup data, and a web server 913 providing the web site services to the caregroup members, to the customer service groups, to the digital mailbox network operators and managers, and to the research team running clinical trials.

In the example depicted, the distribution server 920 includes a log upload server 921, a configuration server 922, a scan upload server 923, a time server 924 a print job server 925, an edition generator 926 and an email processor 927.

According to one embodiment, communications to and from any digital mailbox appliance 900 occurs only when initiated by the digital mailbox appliance 900. The scheduler 915 notifies the task manager 916 which launches the modem controller 917 which establishes contact with the distribution server 920. An alternative method of connection occurs when the user puts an item (form, reply requested, paper clipping, anything . . . ) on the scanner and presses the send button (part of the User interface 907). The send button initiates execution of a scan through the scan controller 906 which puts a compressed digital representation of an image of the item on the scan queue 903 and then establishes a connection to the distribution server 920 by notifying the task manager 916 which directs the modem controller 917.

Once connection is established a number of communications processes take place between elements of the distribution server 920 and the digital mailbox appliance 900. In one embodiment, the processes that occur during a connection fall into three major categories: 1) delivery of print jobs to the digital mailbox appliance 900, receipt of the scan jobs from the digital mailbox appliance 900, and remote maintenance of the digital mailbox appliance 900.

In one embodiment, remote maintenance consists of 1) tracking logged mailbox events (e.g., print and scan events, problem occurrences, program operation histories, heartbeat history, . . . etc.), 2) time synchronization, 3) configuration update (e.g. phone numbers for the modem to call under various conditions, contact schedules, software version information), 4) digital mailbox status information (e.g., ink levels) and 5) applications software updates.

The log upload server 921 collects logging reports from each digital mailbox appliance logger 901 and records them in the database 912 appropriately indexed to the corresponding digital mailbox appliance 900 (using the mailbox's unique ID, for example). Recognized digital mailbox appliance errors are specially noted and appropriate alerts are sent to representatives of the communications service provider.

The configuration server 922 maintains and transmits configuration changes to the configuration manager 902 of each digital mailbox appliance 900 (recognized by its unique ID, for example). Configuration changes (such as the scheduled time of printing the elder's regular delivery) from a variety of sources (such as the administrating caregiver through the caregroup's VPN) are registered in the database 912 and updated into the configuration manager 902 with each contact with the appropriate digital mailbox appliance 900.

According to one embodiment, scans are initiated by the elder pressing a single "Send" button. The scan controller 906 launches a scan process, compresses the scan into JPEG format and places the scan in the local scan queue 903. The scan queue 903 holds the image(s) accumulated until they are transferred to the scan upload server 923. The scan upload server 923 gathers scans sent from each digital mailbox appliance 900 and registers the scans in the database 912. These scans are then delivered to the intended recipient(s) via automated dispatch processes that are launched as described below.

The time server 924 updates the local clocks of each digital mailbox appliance 900. According to one embodiment, each time a digital mailbox appliance 900 contacts the distribution server 920, the time server 924 updates the digital mailbox appliance's local clock through the Time Synchronization process 904. In alternative embodiments, in which the digital mailbox appliance 900 is configured to receive calls, the time server 924 may periodically push time updates to the digital mailbox appliance 900. In other embodiment, the time server 924 may provide time information to the digital mailbox appliance 900 responsive to explicit requests by a digital mailbox appliance.

The print job server 925 collects and sends print jobs to the appropriate digital mailbox appliance 900. According to one embodiment, each time a digital mailbox appliance 900 contacts the distribution server 920, the print job server 925 updates the digital mailbox appliance's local print queue 905.

The delivery generator 926 periodically creates a print job for each digital mailbox appliance. The print job is formatted as specified by preferences stored in the database 912 and includes each of the digital gifts defined in the database 912 that are scheduled for the next delivery to the digital mailbox appliance 900. According to one embodiment, the publication of the caregroup's digital gifts, the timing of publication, the timing of scheduled contact from the digital mailbox appliance 900 and the timing of printing at the digital mailbox appliance 900 is set by the administrating caregiver(s).

At the time schedule for delivery, the scheduler 915 notifies the task manager 916 which launches the print controller 908 to print the print jobs on the print queue 905. According to one embodiment, some print jobs are specially marked for immediate delivery. Such print jobs are printed at the first available opportunity, such as (1) upon completion of the next send operation, (2) upon completion of the digital mailbox appliance's initial connection after being powered up, or (3) at the next scheduled delivery time(s), whichever is first.

The email processor 927 provides traditional email services and parses and manages email transmissions, Short Message Service (SMS) messages, instant messages via ICQ, AIM, MSN, Jabber, Yahoo, Gadu-Gadu, Tlen, Netsend and other IM protocols, and/or MMS messages. Such transmissions and messages may be translated into digital gifts and stored in the database 912 for later batch delivery with a daily delivery, for example. Email messages are also transmitted to members of caregroups on behalf of a user of a digital mailbox appliance, for example when self addressing messages are received and parsed from the digital mailbox appliance. According to one embodiment, handwritten missives originated at a digital mailbox appliance are transmitted by email as attached images or embedded images. Alternatively, a Universal Resource Locator (URL) or other hypertext link may be transmitted to the recipient(s) to allow more efficient delivery and provide the recipient control over when the images are retrieved and displayed.

Figure 10:
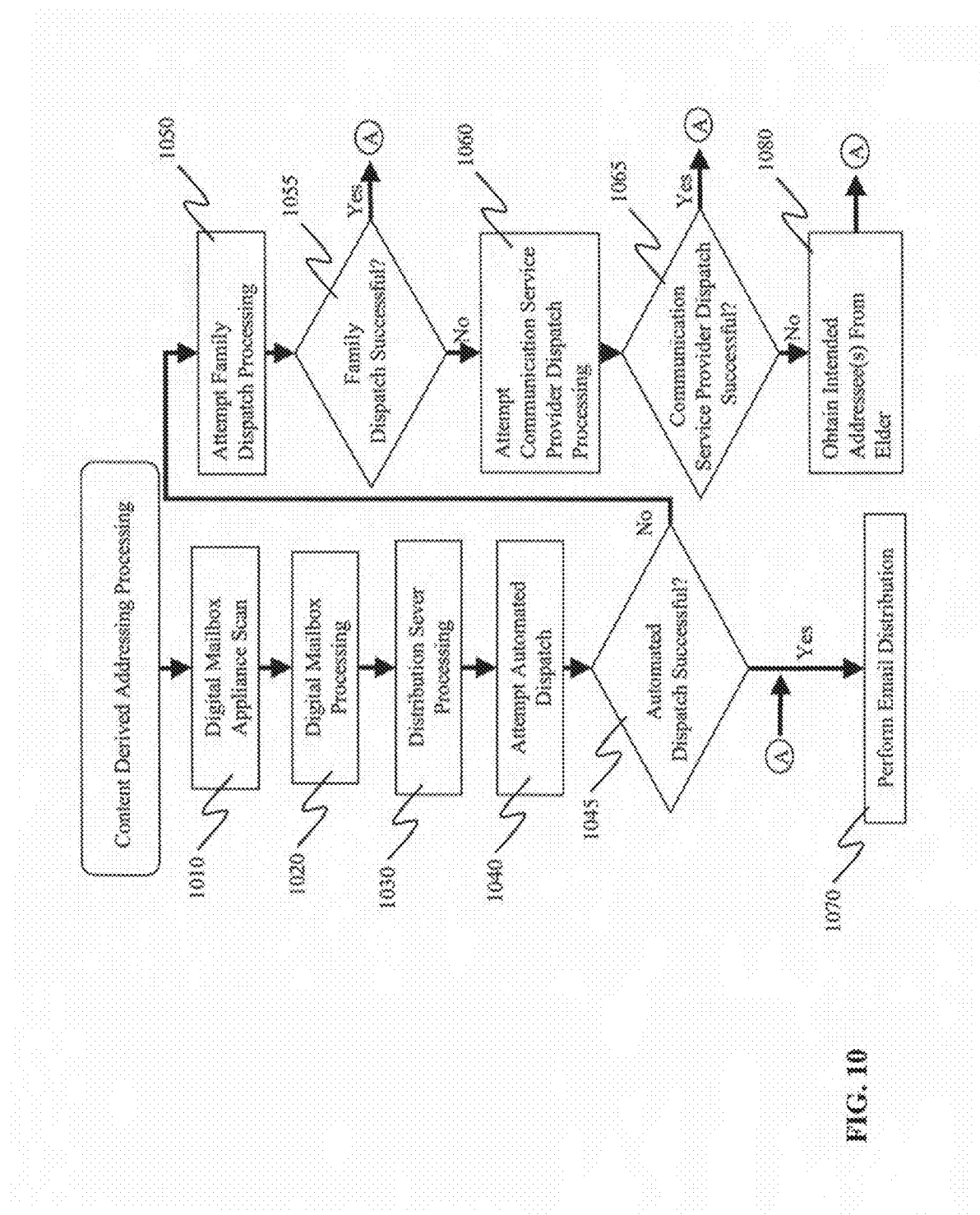
FIG. 10 is a flow diagram illustrating a method of performing content derived addressing according to one embodiment of the present invention.

FIG. 10 is a flow diagram illustrating a method of performing content derived addressing according to one embodiment of the present invention. This process begins as items are scanned into the digital mailbox appliance by the user of the digital mailbox appliance. In one embodiment, an elder may initiate delivery of a correspondence to a member of his/her caregroup by simply placing it on a flat scanner bed and pressing a single button. No typing or dialing is required. Additionally, the elder need not be aware of the individual intended recipients' preferred electronic communications delivery mechanism (e.g., email device, facsimile, digital mailbox appliance, computer system, wireless handheld, etc.) or their "addresses" (e.g., email address, fax number, unique digital mailbox appliance ID, cell phone number, IM username, etc.).

At block 1010, responsive to an indication that a page of a correspondence is present on the flatbed scanner, the digital mailbox appliance "scans" the page to create a digitized version in the form of an image file having a particular graphic, raster or image file format, e.g., Joint Photographic Experts Group (JPEG), JPEF File Interchange Format (JFIF), Tag (ged) Image File Format (TIFF), PostScript, Encapsulated PostScript (EPS), Computer Graphics Metafile (CGM), PICT, Graphics Interchange Format (GIF), Bitmap (BMP), Portable Document Format (PDF) or the like.

At block 1020, the digital mailbox appliance may perform various limited local processing, such as scan conversion, storing of the scan, error recognition and reporting, time stamping and logging the scan, local transaction processing, buffering multiple scans, contacting the distribution server of the communication service provider and forwarding the scan(s) and re-tuning scan parameters of the digital mailbox appliance flatbed scanner as appropriate. According to one embodiment, the scan resolution, file type and compression specification are managed as a part of the digital mailbox appliance configuration definition and are updateable from the distribution server.

According to one embodiment, when the scan of the document by the digital mailbox appliance scanner is complete, the raw bitmap is converted into a JPEG image file that is then saved in an internal upload message queue in a file system local to the digital mailbox appliance. This file system may be either in persistent (non-volatile) memory or RAM, depending upon how the digital mailbox appliance is configured. If the local file system is in persistent memory, then if there is a power failure, the document will not be lost and may be sent upon restoration of power.

According to one embodiment, the digital mailbox appliance may initiate a connection with the communication service provider via an internal modem concurrently with the initiation of a scan. Once the digital mailbox appliance has connected to the Internet, it may look for the existence of any scanned images in its internal upload message queue. The digital mailbox appliance may then upload any files that are in the upload queue. Each time the digital mailbox appliance successfully uploads a file to the distribution server, it may delete the file from the upload queue.

In one embodiment, if there are no files in the upload queue once the modem has connected. If the scanner is still in the process of scanning, the digital mailbox appliance may remain connected to the Internet, wait until the scan is complete, and then upload the scanned message to the distribution server. This process may be repeated until the upload queue is empty and the scanner is no longer scanning. In this manner, the elder may scan multiple documents during one connected session to the Internet.

According to one embodiment of the present invention, various locally detectable errors, such as recognition of blank pages, empty scanner, backside-down pages (i.e., form facing away from scanner as determined by bleed through sensing), duplicate pages, etc., may be resolved locally or reported to the elder (e.g., in the form of an error notification, such as a buzz, screen update, etc.).

According to one embodiment, custom forms are provided to the elder for use in generating correspondence. "Decorations" on any given form may be designed to have a minimum scan compression size (e.g., on the order of 40K bytes to 150K bytes) that exceed a typical blank page (e.g., scan size of between approximately 5K bytes and approximately 15K bytes) or upside-down scan. Pages scanned upside-down typically result in a larger scan size (e.g., >=15K bytes, but less than 40K bytes) than blank pages as a result of bleed through. In this manner, a simple evaluation of the size of the resulting scan may be performed to categorize the scan as one resulting from a legitimate and acceptable page of correspondence, an empty scanner, a blank page, or an upside-down page.

At block 1030, the distribution server performs processing of sets of scan(s) (i.e., one or more uploaded messages originated by the digital mailbox appliance). According to one embodiment, once a scanned image is uploaded, it is saved to the central service database of the communication service provider within a scan data structure along with additional data extracted from the scan (e.g., scanned image file name, date and time information, sizing, etc.) and a scan. For purposes of facilitating coaching by the administrative caregiver, for example, the scan may also be registered in the central service database as having been originated by the particular digital mailbox appliance using the unique digital mailbox ID, for example.

After the set of scans has been successfully stored in the central service database, a notification may be sent to the automated dispatch processing to initiate the automated dispatch processing of block 1040 where automated dispatching software may examine the set of scans for item identification marks, such as a barcode, a MaxiCode (i.e., a two dimensional barcode used by United Parcel Service (UPS) on packing slips for package sorting and addressing), or other identification marks sufficiently identifiable by linear barcode scanning, 2D barcode scanning or Optical Character Recognition (OCR) techniques, to facilitate automated dispatch of the set of scan(s) as described further below.

At decision block 1045, a determination is made whether automated dispatch was successful. If automated dispatch is successful and a particular set of scans is capable of automated dispatch without manual intervention, then processing continues with block 1070. Otherwise, processing branches to block 1050.

According to various embodiments, one or more assisted dispatch processes may be provided as a fallback strategy if automated dispatch processing cannot be successfully completed. In one embodiment, partial processing by the automated dispatch process is preserved and supplied to the assisted dispatch processes to minimize human time and effort.

In one embodiment, if a set of scans cannot be automatically dispatched by the automated dispatch processing of block 1040, the set of scans are placed on an inbound queue for family dispatch processing. When sets of scans are placed on the inbound queue for family dispatch processing, they may be time stamped to ensure timely handling. If a time threshold is exceeded for a particular set of scans, they may be dequeued and placed on an inbound queue for dispatch processing by the communication service provider.

At block 1050, a family dispatch process is performed. At this point in the distribution cycle, image, core data (from, date/time, sizing, . . . etc.), and partial automated dispatch processing (e.g., form identification, resolution of zero or more addressee(s), component parsing (subimage, original), etc.) has already been completed. According to one embodiment, the family dispatch process comprises a manual process of determining the intended recipient(s) of the set of scans.

The responsibility for performing the family dispatch process may be shared or rotated among individuals in the caregroup or may be performed by the administrating caregiver. Regardless, the individual(s) serving in the role of family dispatcher is preferably both capable of interpreting the desires of the elder based on familiarity and specific knowledge and motivated to serve the elder.

At decision block 1055, a determination is made whether family dispatch was successful. If family dispatch is successful, meaning the family dispatcher has handled and a particular set of scans within an acceptable timeframe by identifying one or more members of the caregroup as intended recipients of the set of scans, and marking the set of scans for delivery to the intended recipients (e.g., by including appropriate address information in a distribution list associated with the set of scans), then the distribution of the set of scans continues with block 1070. Otherwise, processing branches to block 1060. The family dispatcher may also manually pass the set of scans and current dispatch state on to the communication service provider dispatcher. Forwarding to the communication service provider dispatcher may also be automated with a vacation setting, for example.

At block 1060, a communication service provider dispatch process is performed. According to one embodiment, the communication service provider dispatch process comprises a manual process of determining the intended recipient(s) of the set of scans and tagging, labeling or otherwise marking the set of scans accordingly.

At decision block 1065, a determination is made whether communication service provider dispatch was successful. Assuming the communication service provider dispatcher is capable of identifying one or more members of the caregroup as intended recipients of the set of scans, then the dispatcher fills in the proper address information for the one or more addressees and the distribution of the set of scans continues with block 1070. Otherwise, at block 1080, the intended addressee(s) may be solicited from the elder via in-band or out of band communications.

According to one embodiment, a workbench application and tools are provided to the dispatchers (e.g., the family dispatcher(s) and/or the communication service provider dispatcher(s)) to facilitate review and analysis of incoming sets of scans for dispatch. For example, a tool for quick orientation flipping may be provided, such as a website "reader" with one click rotation. As a last resort, a family or communication service provider dispatcher may initiate a query to the elder through a communication delivered to the elder's digital mailbox appliance, by phone, or otherwise.

Figure 11:
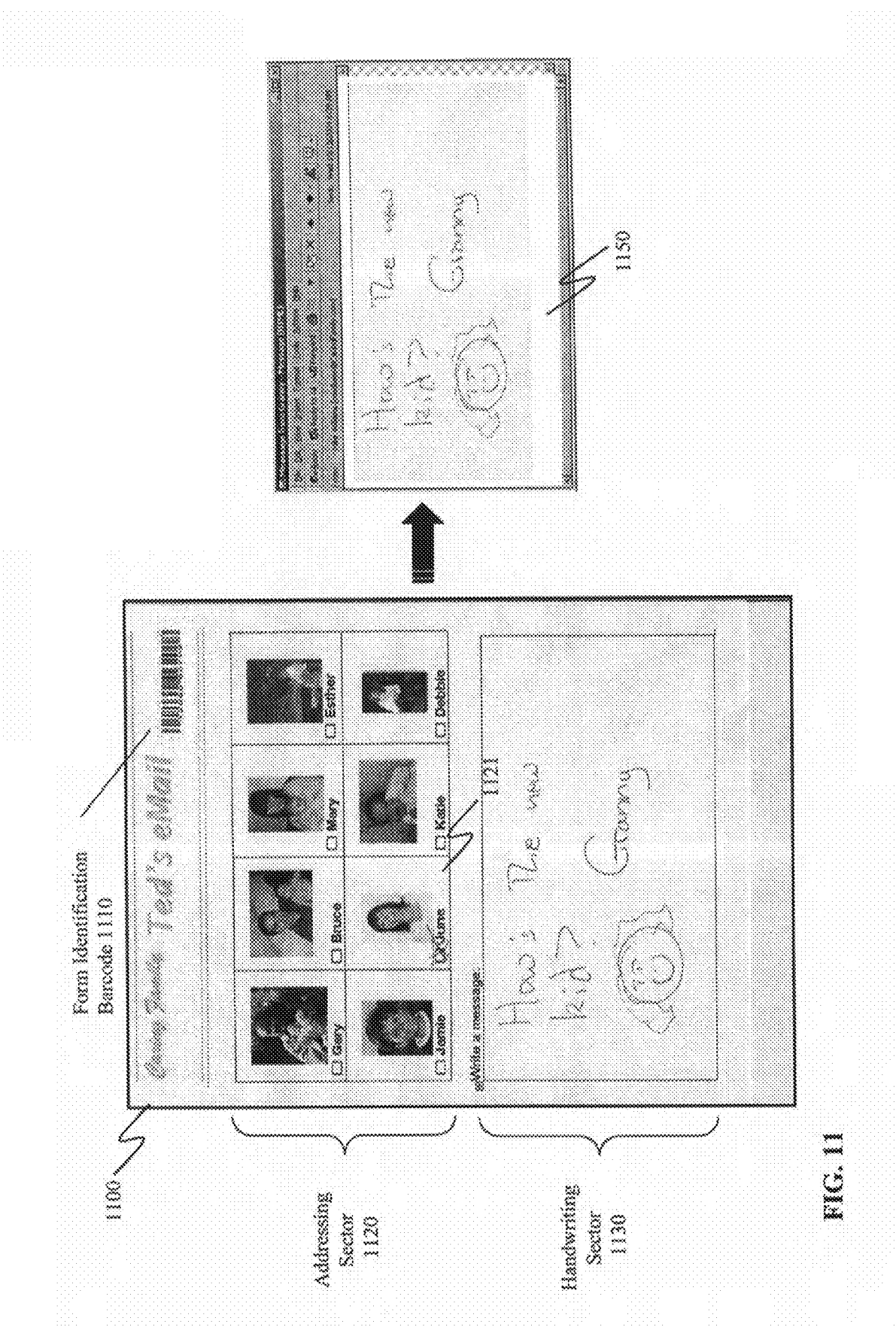
FIG. 11 illustrates a sample completed routing form and resulting email message delivered to the addressee according to one embodiment of the present invention.

FIG. 11 illustrates a sample completed routing form 1100 and resulting email message 1150 delivered to the addressee according to one embodiment of the present invention. According to the present example, the user of the digital mailbox appliance is supplied with pre-formatted routing forms that allow the user to "address" correspondence by simply checking off address information on a routing form. The pre-formatted routing forms may be periodically mailed to the digital mailbox user or printed on his/her digital mailbox appliance.

The routing form 1100 of the present example includes a form identification barcode 1110 and various information segments, such as an addressing sector 1120 and a handwriting sector 1130. As will be described further below, based upon the content and location of the various sectors as identified by the form type, the forms may be parsed by image processing routines running on the distribution server.

In the example depicted, the user of the digital mailbox appliance has marked one of the members 1121 of his/her caregroup as the intended recipient of a brief handwritten message provided in the handwriting sector 1130. If automated dispatch is desired, the intended addressee 1121 may be determined by applying various image processing algorithms to the address sector 1120 as described further below. For example, in one embodiment, an original version of the address sector 1120 of the routing form 1100 may be compared to the completed (marked) version of the address sector 1120 of the routing form 1100 to determine whether one or more addressees have been marked.

According to alternative embodiments, the user of the digital mailbox appliance may be provided with preprinted addressee identification labels containing the names and/or photos of the members of the user's caregroup and identification marks, such as a barcode, data matrix, semicode, MaxiCode, or the like, uniquely associated with individual members of the caregroup. The elder might be encouraged to think of them as addressing "stamps." The user then "addresses" correspondence prior to scanning by affixing one or more preprinted labels in a specified area of the routing form. Identification labels may also be created to represent certain subgroups of the caregroup members, such as grandkids, nieces, nephews, children, and everyone. In this manner, the user of the digital mailbox appliance may easily direct correspondence to appropriate subgroups of his/her caregroup when appropriate. According to another alternative embodiment, the user has reusable addressing card(s) that they lay down on the flatbed along with the correspondence, photo or clippings they intend to send. Addressing card variations include, (1) a "to card" for each possible recipient (and one for everybody—the aggregate) and (2) a single plasticized card with check boxes for the desired addressee(s).

Yet another way to simplify addressing of correspondence for users of digital mailbox appliances is to provide pre-printed forms that are recognized by the communication service provider as being destined to a specific member of the caregroup or a specific subgroup. Again, identification marks may be used, such as barcodes and the like to communicate the information regarding the intended addressee(s), but in this case the identification marks would be part of the routing form rather than supplied as preprinted labels. According to another embodiment, the digital mailbox appliance user uses any previously received message or digital gift from a caregroup member as a routing form to identify that caregroup member as the intended addressee, jots a note (or not) and then sends the optionally annotated previously received message or digital gift optionally followed by photos, clippings, or any number of additional pages. All the scans are gathered up by the communication service provider and delivered to the original sender of the message or digital gift. Thus, an elder can send off a quick thank you note on any digital gift (or even items from the communication service provider).

In one embodiment, in order to send an electronic communication to the indicated addressee(s), the digital mailbox appliance user places the completed routing form on the flatbed scanner of the digital mailbox appliance and presses the "Send" button. In the present example, the result of the user sending the routing form 1100 is delivery of message 1150 to June. Upon receiving the scanned image of the routing form 1100, the communication service provider's infrastructure takes care of the rest, as described below, for example, by extracting the handwriting sector 1120 from the scanned image of the routing form 1100 and including the extracted image of the handwriting sector 1120 as an inline image within a standard email message. Alternatively, the extracted image may be sent as an attachment or a URL to the extracted image may be sent.

Figure 12:
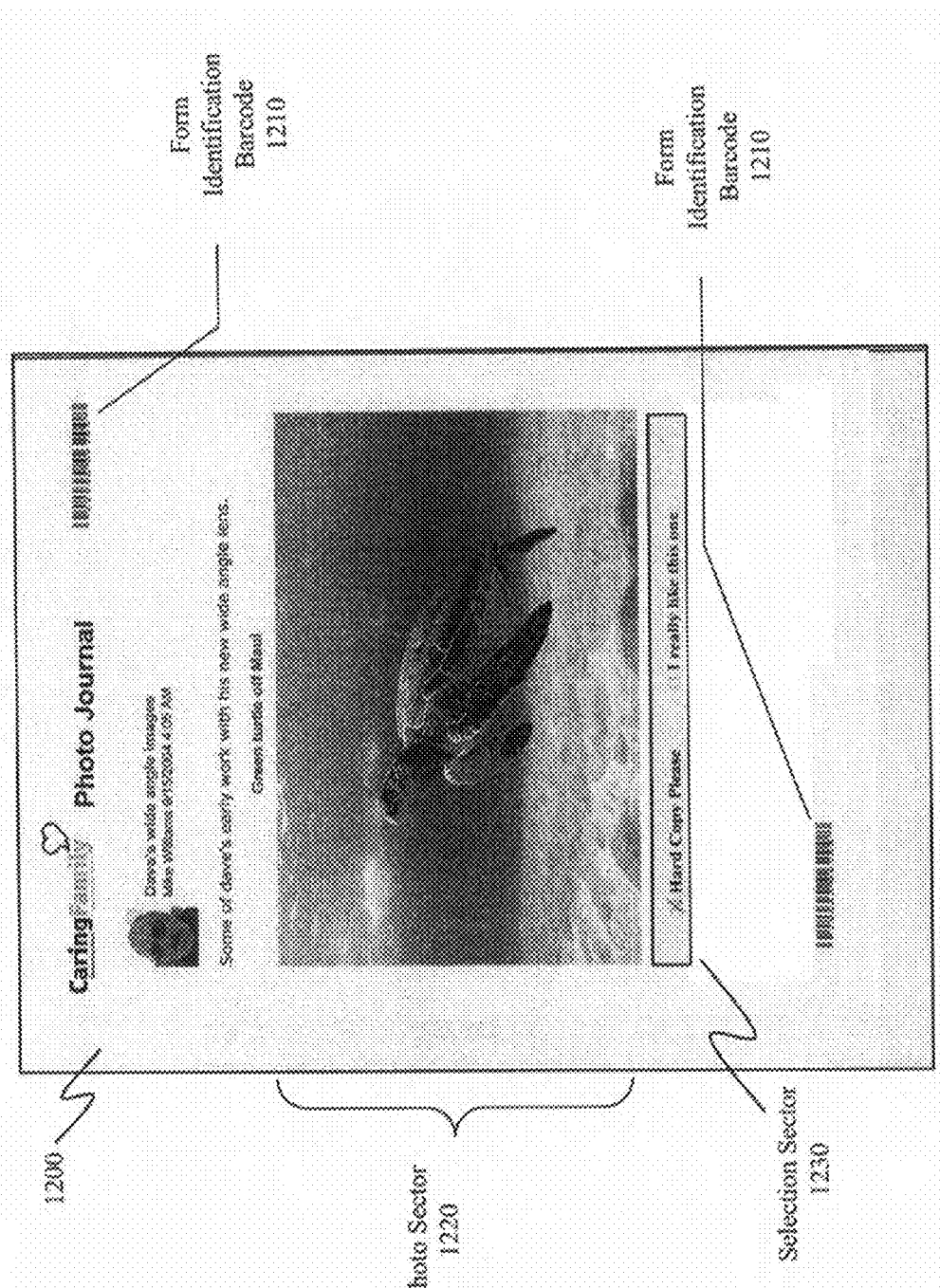
FIG. 12 illustrates a sample completed return-reply requested form that may be created and delivered to a digital mailbox appliance responsive to a caregroup member request according to one embodiment of the present invention.

FIG. 12 illustrates a sample completed return-reply requested form 1200 that may be created and delivered to a digital mailbox appliance responsive to a caregroup member request according to one embodiment of the present invention. According to the present example, a caregroup member may provide a photo journal form 1200 to an elder and/or other members of the caregroup to allow reprints to be ordered of one or more photos or allow the recipient(s) to vote for a favorite.

In this example, the photo journal form 1200 includes a form identification barcode 1210 to allow the communication service provider to identify and parse the form, a photo sector 1220 depicting a photo and a corresponding selection sector 1230. In alternative embodiments, one or more pairs of photo sectors 1220 and selection sectors 1230 may be include on a single form. In any event, the originator of the completed photo journal form 1200 has marked a "Hard Copy Please" selection from the check-off list to request a hard copy of the photo depicted in the photo sector 1220. Various alternative selections are contemplated. For example, the digital mailbox appliance user, may be provided with the option of having a digital version of the photo stored as an eCard image and/or in his/her photo shoebox for future use.

Figure 13:
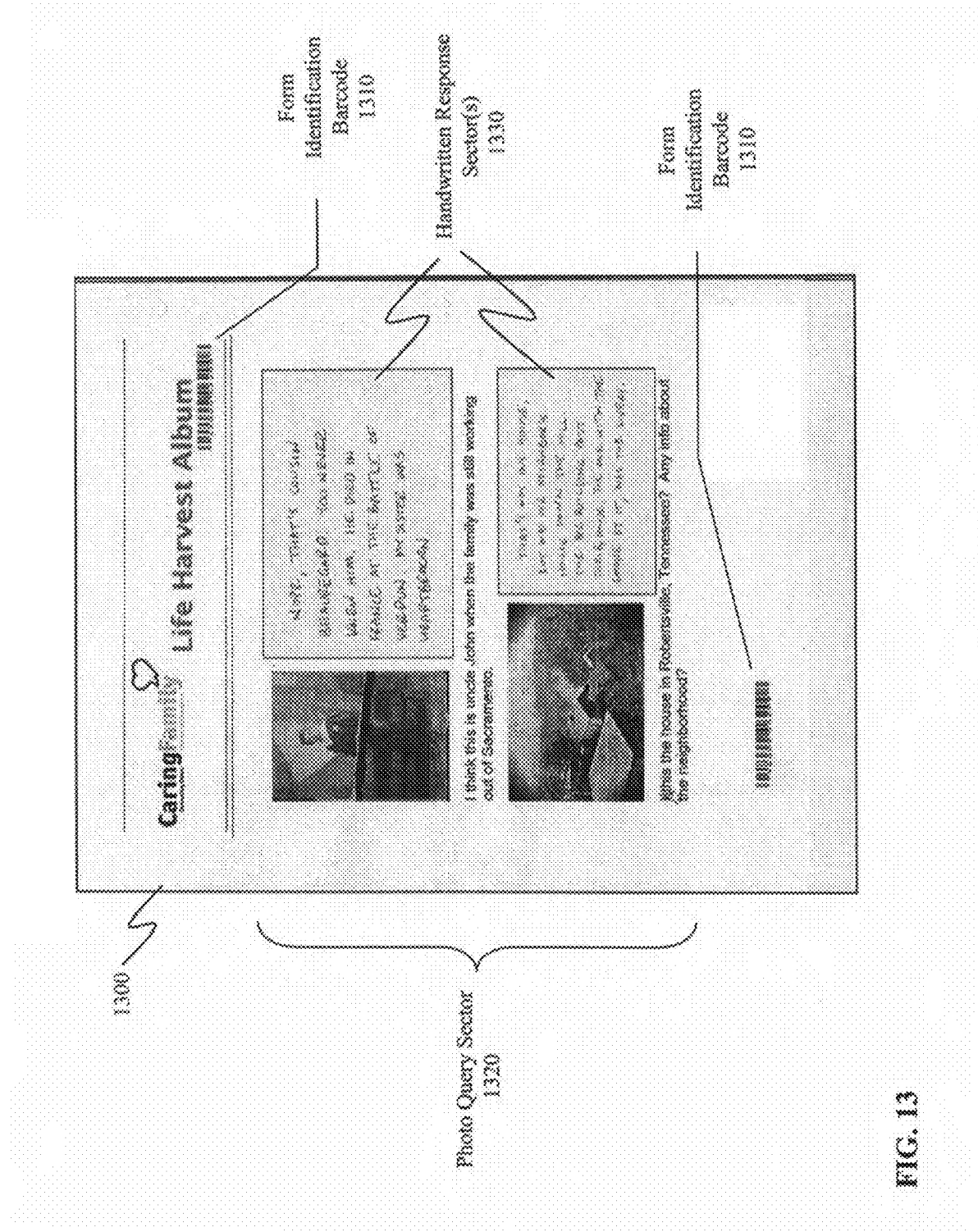
FIG. 13 illustrates another sample completed return-reply requested form that may be created and delivered to a digital mailbox appliance responsive to a caregroup member request according to one embodiment of the present invention.

FIG. 13 illustrates another sample completed return-reply requested form 1300 that may be created and delivered to a digital mailbox appliance responsive to a caregroup member request according to one embodiment of the present invention. According to the present example, a caregroup member may send a life harvest album form 1300 to an elder to solicit input regarding one or more photos as part of a family or caregroup project. The life harvest form 1300 includes a form identification barcode 1310 in one or more locations to allow the communication service provider to identify and parse the form, a photo query sector 1320 which may include one or more photos for discussion and corresponding handwritten response sectors 1330 for elder feedback.

Figure 14:
FIG. 14 illustrates another sample completed routing form that may be provided by the communication service provider to a digital mailbox appliance user and customized for the user according to one embodiment of the present invention.

FIG. 14 illustrates another sample completed routing form 1400 that may be provided by the communication service provider to a digital mailbox appliance user and customized for the user according to one embodiment of the present invention. According to the present example, the routing form 1400 includes a form identification barcode 1410 in one or more locations to allow the communication service provider to identify and parse the form, an addressing sector 1420, a handwriting sector 1430, and a check-box 1440 to indicate additional pages will follow.

In the example depicted, the user of the digital mailbox appliance has specified broadcast distribution of the written message in the handwriting sector 1430 message by marking check-box 1421 in the addressing sector 1420 corresponding to distribution to "everybody" listed in the addressing sector 1420. According to the present example, if the user of the digital mailbox appliance intended to scan additional pages to be included as part of the distribution, then her/she would simply mark check-box 1440. As described further below, multiple page or continuous communications may be recognized in various other ways.

Figure 15:
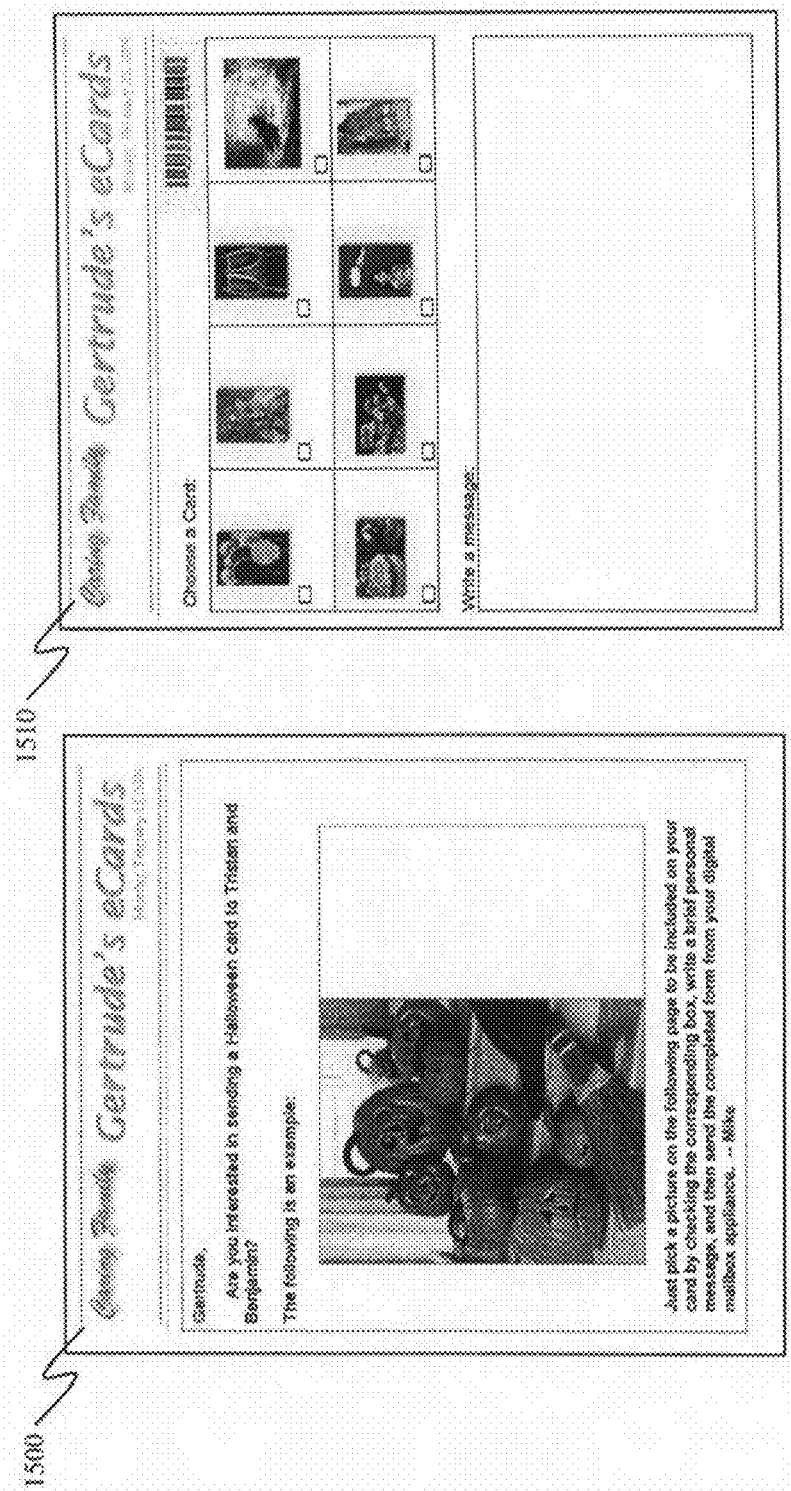
FIG. 15 illustrates a sample coaching message and associated form that may be directed to a digital mailbox appliance user according to one embodiment of the present invention.

FIG. 15 illustrates a sample coaching message 1500 and associated form 1510 that may be directed to a digital mailbox appliance user according to one embodiment of the present invention. In the present example, a caregroup member, Mike, has sent coaching message 1500 containing a sample Halloween eCard and directions to encouraging an elder, Gertrude, to send a Halloween card to the elder's nephews. The caregroup member has also provided the elder with an eCard selection form 1510 to further simplify the task.

Figure 16:
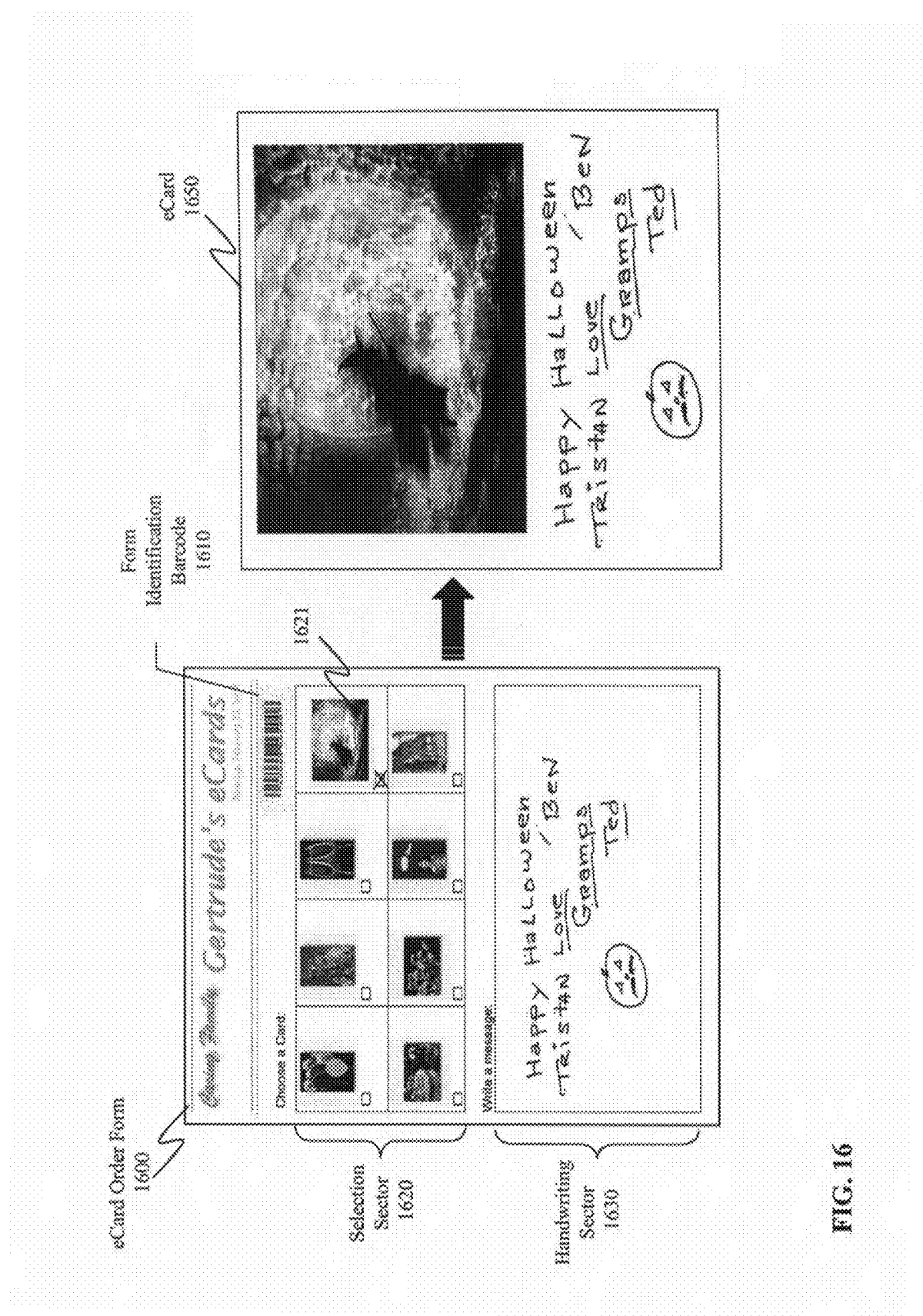
FIG. 16 illustrates a sample completed greeting card form, eCard form, originated at a digital mailbox appliance and a resulting eCard generated responsive thereto according to one embodiment of the present invention.

FIG. 16 illustrates a sample completed eCard form 1600 originated at a digital mailbox appliance and a resulting eCard 1650 generated responsive thereto according to one embodiment of the present invention. In the present example, an elder, Gramps Ted, has completed eCard form 1600 by marking a desired image 1621 in the selection sector 1620 and providing a personalized message in the handwriting sector 1630. As will be described further below, by simply checking boxes a user of a digital mailbox is able to specify the composition of a customized eCard, such as the resulting eCard 1650. In the present example, responsive to receipt and processing of eCard form 1600 by the communication service provider, the resulting eCard 1650 may be composed by retrieving the desired image 1621 from the central service database and combining the retrieved image with handwritten materials extracted from handwriting sector 1630 of eCard form 1600.

While the examples of FIGS. 15 and 16 are explained with reference to a manually initiated coaching message and a specific holiday, similar coaching messages may be automatically generated for various other holidays or family "days of note," such as birthdays, anniversaries, or the like, such as any condition when a traditional greeting card would be appropriate.

Figure 17:
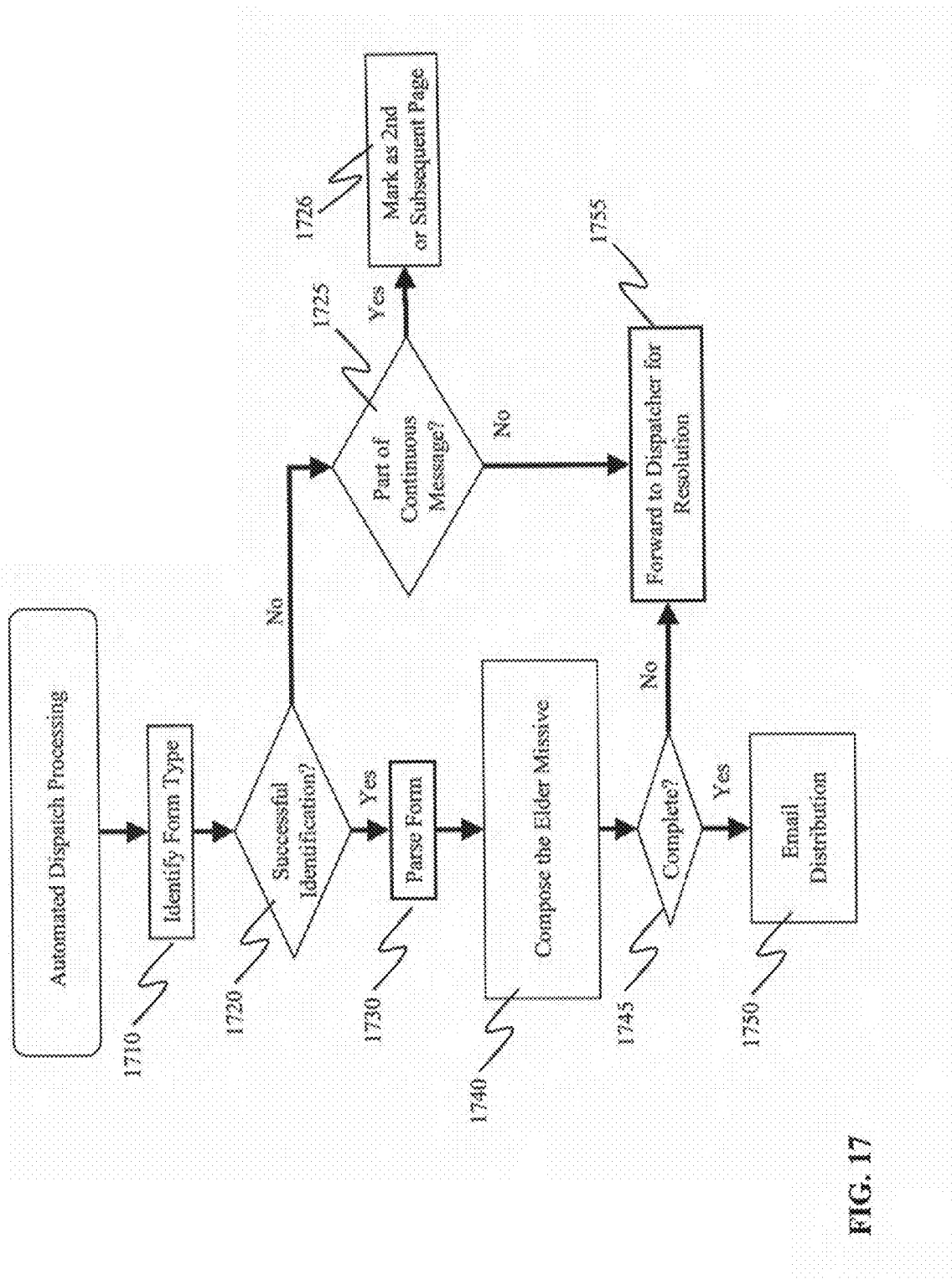
FIG. 17 is a flow diagram illustrating a method of performing automated dispatch according to one embodiment of the present invention.

FIG. 17 is a flow diagram illustrating a method of performing automated dispatch according to one embodiment of the present invention. In the present example, responsive to a set of scans uploaded from a digital mailbox appliance, the distribution server of the communication service provider initiates image processing at block 1710 to identify the type of predefined form employed for this particular missive. Typically, the first page of an elder missive will include form identification marks that allows a determination to be made regarding which of a predefined set of forms is represented by the first page of the elder missive. For example, in one embodiment, the form identification marks are a barcode that is included on each form in the upper right-hand corner of the form and the lower left-hand corner of the form. Various other identification marks and locations may be employed. For example, barcodes (code 128, code 39, Interleaved, EAN, . . . etc), data matrix, MaxiCode, OCR (A or B) and other machine readable codes. Depending upon the particular implementation, there are certain tradeoffs among identification mark density, resolution, transmission time, software availability/price/programmability, etc. that would typically be evaluated.

Certain simplifying assumptions made in the automated dispatch techniques described below include an assumption that blank page, empty scanner and backside-down page errors are resolved local to the digital mailbox appliance or at least prior to execution of this automated dispatch processing. Additionally, it is assumed that certain physical page placement restrictions are implemented at the digital mailbox appliance resulting in only three possible orientations of a scanned version of a form (i.e., rightside-up, upside-down and backside-down). Finally, it is assumed that the item or form identification marks are included at one or more predetermined locations on each type of form of the set of predetermined forms. According to one embodiment, the communication service provider may supply special paper for use with the digital mailbox appliance to force a specific orientation in the flatbed scanner. For example, the bottom right hand corner of the supplied paper may be clipped off to match a feature of the flatbed scanner and/or the input tray to require a specific orientation of the paper at scan time.

Given the above simplifying assumptions, the form recognition and identification processing need only examine one or two general locations of the scan (one assuming the form is rightside-up and one assuming the form is upside-down) for purposes of locating form identification marks. If a form identification mark, such as a MaxiCode barcode, is located, then the information conveyed thereby may then be used to retrieve information regarding the corresponding form type. For example, the characters of information represented by a barcode (e.g., the barcode value) may be used as part of a query to retrieve information from the central service database of the communication service provider.

If, at block 1710, no form identification marks are located, the form type identification process has failed and further analysis is performed to determine if the current scan is a second or subsequent page of a multipage message. If form identification marks are located, however, then as a result of each value defining a specific form of a set of predefined forms, information regarding the characteristics of the form now identified may be retrieved. As described above, each form type may have a set of defined form segments, such as zero or more address sectors or areas, selection sectors or areas, and/or handwriting sectors or areas. After having failed in determining the type of form or having succeeded in determining the type of form represented by the current scan and retrieving information regarding the form's characteristics (e.g., the number, type and locations of the various included segments), automated dispatch processing continues with decision block 1720.

At decision block 1720, a determination is made regarding the successful identification of a form type associated with the current scan. If a form type was successfully identified in block 1710, then processing continues with block 1730; otherwise processing branches to decision block 1725.

At decision block 1725, it is known that no form identification marks were located within the current scan. In view of the simplifying assumptions summarized above, it can be appropriately deduced that either (1) the current scan "page" was intended by the originator to be part of a continuing correspondence and should therefore should be dispatched in accordance with the prior scan page; or (2) the page of correspondence represented by the current scan page did not employ a recognized form.

A determination is made at decision block 1725 whether the current scan is intended to be part of a continuing communication. According to one embodiment of the invention, if additional scanned images are received within a predefined period of time of a prior scan, those images are assumed to be included with the previous image and are sent to the recipients identified in or associated with the previous image. The communication service provider may infer that received scans are $2^{nd}$ or subsequent pages of a continuing communication (collectively or individually "follow-on" pages) based on the timing of the scans and a lack of identification markings. barcode. In one embodiment, scans are considered follow-on pages only if they are originally scanned within a short duration, e.g., seconds to minutes, after the 1st page form (e.g., a routing form). The duration may be a configurable parameter set by the communication service provider and/or an administrating caregiver. If subsequent scans have different recipient information, however, then the automated dispatch process will treat such subsequent scans as a new message to be sent to a new set of recipients identifiable by information contained within such subsequent scans. In this manner, the elder is able to send multiple pages to a set of recipients without having to identify the set of recipients on each page.

As described earlier, in alternative embodiments, the elder may check a box on the first page of a correspondence to indicate whether one or more pages follow. Alternatively, a check box may be included on follow-on form pages to allow them to be marked by the user of the digital mailbox appliance as being associated with an earlier scanned "address" or routing page. Regardless of the mechanism or algorithm use to make the determination, if, at decision block 1725, it is determined the current scan is part of a continuing communication, then processing continues with block 1726. Otherwise, processing continues with block 1755.

At block 1726, the current scan is marked as a follow-on page (e.g., a $2^{nd}$ or subsequent page of a continuing communication). According to one embodiment, this marking process includes modifying information stored in the corresponding scan data structure in the central service database. As discussed further below, the composition process notes the existence of follow-on pages and appends them to the basic missive to be emailed to the addressee(s).

At block 1755, the current scan is forwarded to a dispatcher for manual resolution, e.g., determination of missing information, such as addressee(s) and/or choices, and/or determination regarding the current scan's association with earlier scanned pages.

At block 1730, the form represented by the current scan is parsed in accordance with the type of form previously identified and the characteristics thereof. Information typically sought, identified and/or extracted during form parsing includes one or more of addressee(s), choices, images spaces, such as handwritten material, drawings, photos, clippings, etc., and $2^{nd}$ or following pages. According to one embodiment, addressee(s) and choices may be determined using various image processing techniques, such as XORing the original sector of the form with the marked version. In this manner, checked boxes, filled-in boxes and boxes marked in other ways may be interpreted as a selection of the addressee or choice associated with the marked box.

Some information is optionally defaulted within the scan data structure based upon the barcode value. For example, in the case of an eCard resulting from a coaching message, the communication service provider may know a priori the addressee(s) and need only determine one or more choices and an image region containing a handwritten message to complete composition of the missive.

In one embodiment, information extracted from a form filled in by the elder may be used to build a digital gift for one or more addressees. For example, a one-page form, such as eCard form 1600 of FIG. 16, may be used by an elder to select a type of Halloween eCard for delivery to one or more members of the elder's caregroup. The form may include an area for selecting one or more addressees (or the addressees may be determined based on the form identification barcode 1610), an area for the elder to provide a hand-written note (e.g., handwriting sector 1630), and a selection area to indicate choices made, such as a check-off list for selection of a desired image to be used for the Halloween eCard (e.g., selection sector 1620). Continuing with the present Halloween eCard example of FIG. 16, upon receipt of the scanned image of the eCard form, the form type is determined from the form identification barcode 1610, the originator may be determined based upon the form identification barcode 1610 or the unique ID associated with the digital mailbox appliance, and the addressees (e.g., the two nephews and an appropriate email address (or addresses) for delivery, such as their mother's email account) may be determined based upon information marked by the elder in an address segment of the form or based upon the form identification barcode 1610, which may associated the form with a particular coaching message concerning the nephews. Additionally, a determination can be made regarding the image the elder has selected to send (e.g., from a marking in a check box associated with the desired image 1621). Finally, an image of writing and/or any additional drawings may be extracted from the handwriting sector 1630 to form the inside of the eCard being sent.

According to one embodiment, instructions for composition of the elder missive based upon the particular form employed are retrieved from the central service database. The instructions from the central service database may then be used to compose a completed missive from the parsed components. This includes appending follow-on page images to the core document (for example an embedded handwritten note appended to a birthday card).

At decision block 1745, a determination is made regarding the completeness of the missive. If insufficient data is available to construct the missive (e.g., no marking in a selection section of the form), then composition cannot be completed, the processing state is marked in the central service database, a notification is sent to the dispatcher and processing continues with block 1755. If sufficient data is available to construct the missive, then processing continues with block 1750.

At block 1750, the missive is sent (e.g., emailed) to the appropriate addressee(s) by the methods specified in their respective personal information stored in the central service database. Typically, the specified method is defaulted to the primary email address.

Figure 18:
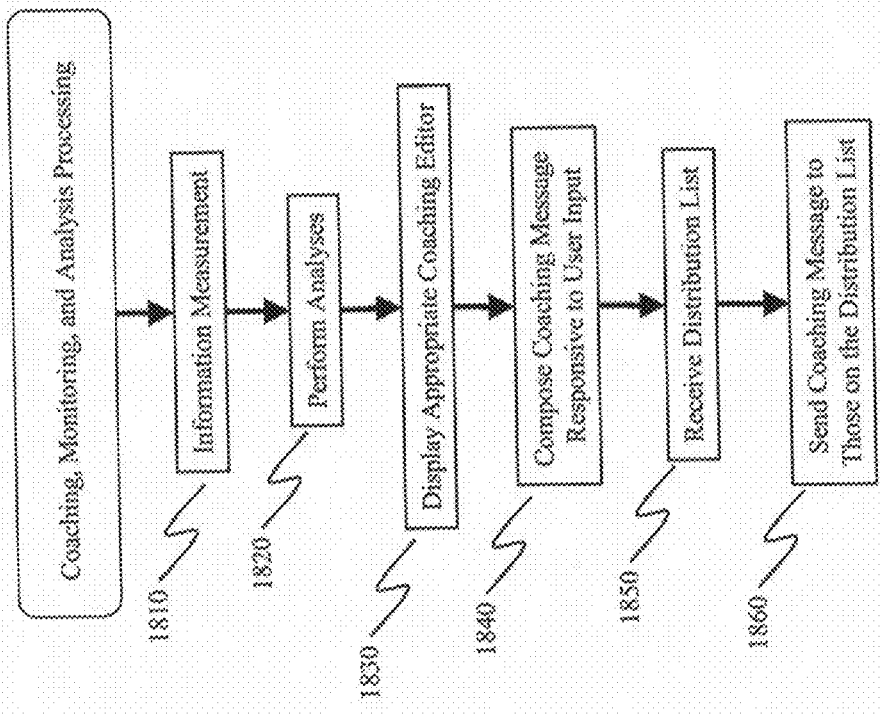
FIG. 18 is a flow diagram illustrating a method of performing coaching and monitoring analysis according to one embodiment of the present invention.

FIG. 18 is a flow diagram illustrating a method of performing coaching and monitoring analysis according to one embodiment of the present invention. While making the interfaces to the communication service provider for both the caregroup members and the target of the caregroup exceptionally easy is one mechanism to influence the quality, quantity, effect and timeliness of communications; a variety of monitoring and assessment techniques are also provided according to various embodiments to allow the administrating caregiver(s) and other authorized family members to influence communications to and from the elder.

According to various embodiments, the communication service provider may be provided limited access to communications exchanged between members of caregroups and corresponding caregroup targets for the purpose of facilitating the monitoring of usage of various technologies and features provided by the communication service platform and then taking or suggesting actions to administrating caregivers in response to various observed usage patterns. In one embodiment, such actions suggested or taken by the communication service platform are designed to seek to enhance the effectiveness of the communication system platform in supporting elders, for example, by stimulating increased communication with the elder if a drop in communication rate is detected.

The coaching features may employ a supporting technology referred to as project templates. An example of a project template is a user tool that (1) makes it easy for a family member to initiate a project, such as building a family recipe collection, or creating a cryptogram puzzle with text of interest to the elder, or providing a Health Tip of the Week, while (2) allowing the communication service platform to recognize and track that the activity is taking place. By monitoring the use of such project templates, the communication service platform can determine which system features are being used and which are not, and suggest new projects and/or activities, if appropriate, in response to a drop in communication with the elder. Additionally, the communication service platform may provide guidance and/or direction regarding potentially useful features of the system that are not being used spontaneously by members. For example, coaching messages may be delivered to caregroup members regarding content types they have not yet used (e.g., eCards, crossword puzzles, family recipes, carousels for supplying commercial and/or family data streams, health advice, amusing news, entertainment topics, such as celebrity gossip and TV and/or movie reviews, special interest etc.). According to various embodiments of the present invention, each content type is supported by a corresponding project template that may act both as a tool to make it easier for caregroup members to use the associated feature, and as a marker, enabling the communication system platform to recognize and track the features being utilized.

According to one embodiment, administrating caregiver(s), other authorized family members and personnel associated with the communication service provider (if desired and authorized by the caregroup) may be provided with access to a communications dashboard that presents communication history (under a variety of novel analyses) and a wide variety of coaching tools that can be used to influence communications to and from the elder. These coaching tools may be coupled with subtle (often indirect) coaching techniques to encourage the creation of digital gifts and other communications to and/or from the elder.

At block 1810, various information is measured regarding the communications exchanged between members of a caregroup and the target of the caregroup. In one embodiment, information measured and/or tracked includes number of digital gifts exchanged, time, date, sources and types of digital gifts and the content employed (e.g., component images embedded in the digital gifts), the level of personalization of digital gifts, and key words indicative of effectiveness of the communication.

At block 1820, various analyses are performed based upon the information measured. For example, analysis may be performed to produce one or more of an effectiveness rating, a rating regarding intellectual stimulus, and a rating regarding activity inducement. Digital gifts often include family annotated images. These annotations allow metrics to be generated regarding the emotional content of the digital gifts. For example, a digital gift including an annotated photo that refers to the name or nickname of grandchildren and/or includes affective terms (e.g., smiling, happy, . . . etc.) may have a higher affective value rating than a digital gift including a stock photo. Lexical Semantic Indexing (LSI) and Lexical Semantic Analysis (LSA) may also be used as one measure of the similarity between images. Other specific information available for analysis includes names, nicknames, kinship, elder ratings of information received (from, for example, best-of ratings that may occasionally be requested from the elder), family events from the schedule (birthdays, valentine's day, . . . etc.).

Simplistic analysis may involve a count of digital gifts delivered by member, by type, by time. More complex analysis may involve rating various parameters, such as affective-emotional value (A) of communications, intellectual stimulus value (IS) of communications, and activity induced value (AI) of communications, based on the content of the communications, e.g., digital gifts and associated images and text.

According to one embodiment, digital gifts may be scored based on the sum of items plus an individual weighting for various digital gift types. For example, digital gifts may have associated base rating value tuplets (A, IS, AI) with enhanced points available for specific content analysis (e.g., use of a family photo of the granddaughter over a stock photo, a new stock image was selected as opposed to using the system supplied first guess, whether personalized text was added, . . . etc.).

Scoring a crossword puzzle might proceed as follows. If delivered as a personalized digital gift from a member of the caregroup, base gift value of (5, 10, 5). If delivered in stock form (not personalized), base gift value of (1, 3, 2). Puzzles also might include associated rating value tuplets (A, IS, AI) based on difficulty, complexity, number of words, length, subject matter, etc. Puzzles might have IS ratings of 1 to 10 and AI ratings of 1 to 10. A particular puzzle might have a rating value tuplet of (0, 5, 5). According to the present example, when this particular puzzle is delivered as a personalized digital gift the total score would be (5+0, 10+5, 5+5)= (5, 15, 10). In contrast, when this particular puzzle is delivered without personalization, the total score would be (1+0, 3+5, 2+5)=(1, 8, 7).

Scoring a photo essay might proceed as follows. Base gift value of (5, 2, 0), plus an author bonus of 1 to 10 points (A) depending on age and kinship, plus a per item bonus of 1 to 10 point (A) for each image included in the photo essay depending upon the subject matter depicted.

According to one embodiment, intellectual stimulus of content from various information feeds and from the central service database of the communication service provider that are delivered to elders, such as crossword puzzles, interest based items, . . . etc., may be rated by the communication service provider based on the content source or by explicit ratings stored within the central service database by a content management team associated with the communication service provider.

At block 1830, responsive to a selection of a coaching tool from the dashboard of the communication service provider website interface by an appropriate caregroup member, the corresponding coaching editor is displayed. The dashboard may support a number of coaching and reminding tools and editors available both to the appropriate family member(s) and the communication service provider (human-driven and/or automated). Various forms of indirect coaching and prompting have been found to have a significant impact on the quantity and quality of communications. According to various embodiments, authorized family members may use coaching tools/editors to perform one or more of the following:

- annotate a weekly summary of digital gifts (and in particular their family photos) sent widely throughout the family,
- launch reminders of upcoming family events (birthdays, father's day, . . . etc.) with embedded digital gifts ready for immediate sending or editing (to the elder or other family members),
- send projects of varying sizes to the elder (e.g., a return-reply requested form, such as a photo journal (see FIG. 12), a life harvest album (see FIG. 13), or an eCard form for sending a birthday card or holiday card to a specific family member (see FIG. 15 and FIG. 16)). Furthermore, these items can be directed through other family members to broaden the base of communications.
- welcome new members to the caregroup,
- notify members of the availability of new digital gift editors or new content enhancing existing digital gift editors,
- create best-of selections,
- remind members of digital gifts that they have not tried, or not tried for a significant length of time (this function is typically automated based upon parameters set by the dashboard operator),
- request additional personal information from members for the directory and the family schedule (such as birthday information), Examples of various coaching editors are described below. At block 1840, the coaching editor composes the coaching message responsive to user input. At block 1850, the coaching editor receives a list of one or more addressees to which the coaching message is to be distributed. At block 1860, the coaching message is distributed to the addressees.

The dashboard may also enable the user to specify notifications and/or reminders to be sent to him/herself on specific conditions (e.g., low levels on specified content carousels, lack of personalized communications to the elder, lack of intellectual stimulus items, . . . etc.).

Similar and/or additional dashboard capabilities may also be made available to communication service provider operated services. Thus, the communication service provider may automate various coaching methodologies for a newly formed caregroup until one or more family members take responsibility for various services (e.g., providing a weekly update of elder deliveries to the caregroup, notification of new editors of content, event reminders, . . . etc.).

Simple coaching (automated and/or manual) is based on use or nonuse of specific features, or on overall usage levels. But, more sophisticated coaching may also encourage particular categories of use as described further below. For example, by examining the assessed value of communications between caregroup members and the target of the caregroup and/or usage of various project templates across a family, the communication service platform may detect that the family is making little use of features that emphasize affective content (for example, family photos), or features that promote cognitive stimulation (for example, puzzles or projects), and suggest features in these categories. Similarly, if a family is not using any features that direct health or lifestyle information to the elders, coaching messages may be used to encourage doing so.

According to an alternative embodiment, digital gifts can be gathered into a daily delivery or "Daily Edition", rather like a family newsletter. Typically, a cover photo and a table of contents is used as a cover page. The Digital Edition also plays a useful role in encouraging communication among family members: when family members know what the elder is seeing in the Digital Edition, it stimulates them to communicate more with the elder, and with one another. That is, one family member's communication prompts communication by others. According to one embodiment, the communication service supports this implicit coaching effect by making Digital Edition contents available to family members on the Web via the family VPN website, for example.

Figure 19:
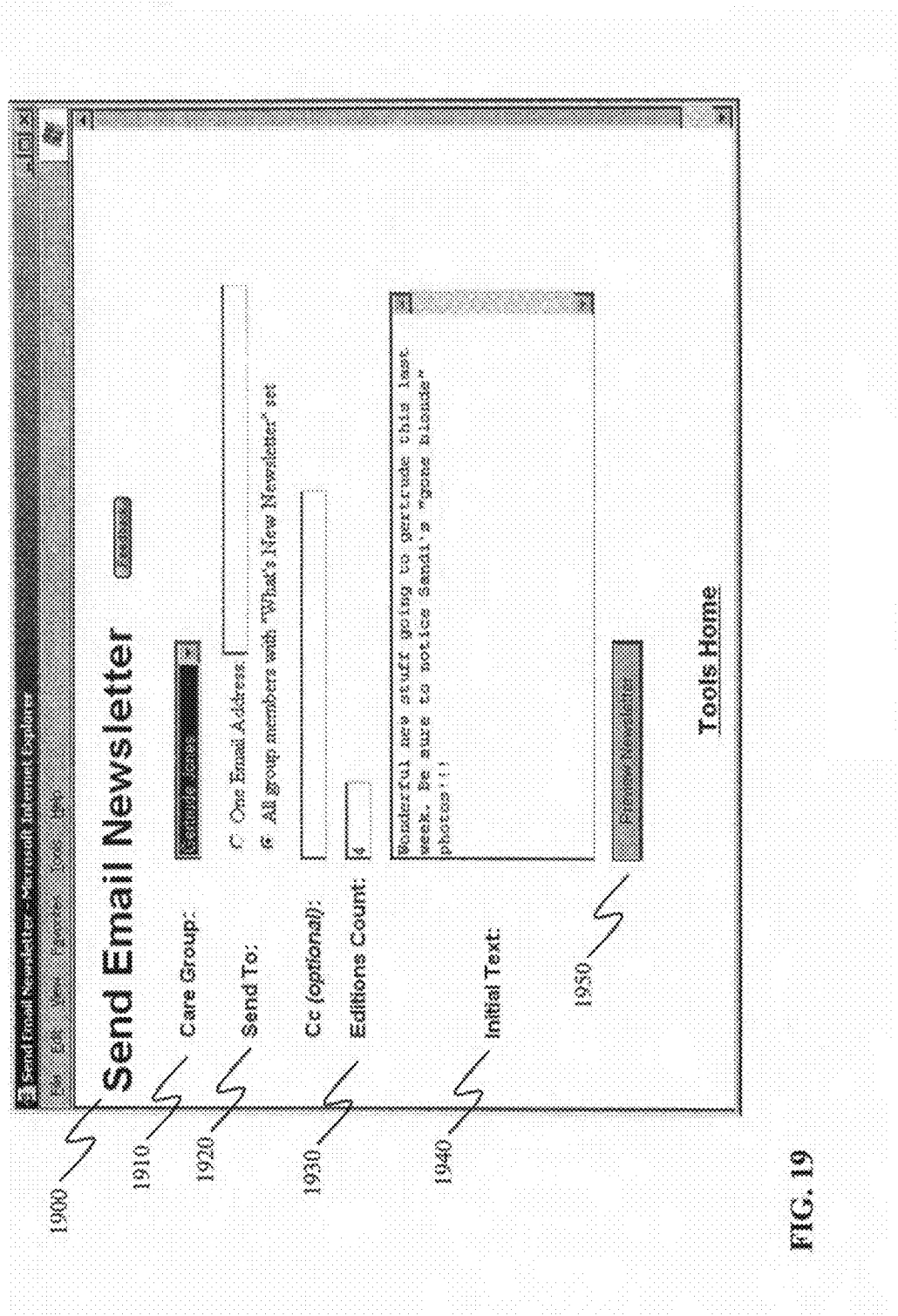
FIG. 19 illustrates a user interface screen depicting a coaching message editor for a weekly summary according to one embodiment of the present invention.

FIG. 19 illustrates a user interface screen 1900 depicting a coaching message editor for a weekly summary according to one embodiment of the present invention. According to the present example, the administrating caregiver(s) may periodically, e.g., weekly, provide an update or summary to the caregroup regarding communications among the caregroup members and the user of the digital mailbox appliance corresponding to the caregroup.

If the administrating caregiver(s) participate in more than one caregroup, they initially select the caregroup via a user interface input object, such as a caregroup dropdown list 1910. The administrating caregiver may also select the caregroup members to which this coaching message is to be sent by using user interface input objects, such as the "Send To" radio buttons 1920 and/or corresponding dropdown Caregroup member email list.

According to various embodiments, some types of coaching message pre-filter (or at least suggest a filtering) of member addressees. For example: ex-officio members may be filtered from certain types of coaching messages as appropriate. A welcome coaching message suggests inclusion of only caregroup members who have not been introduced to the communication service or website, or who have not responded to an earlier welcome coaching message. The weekly summary email newsletter coaching message may filter caregroup members who have opt-ed out. A coaching message relating to encouraging the use of a particular digital gift type would presumably filter any caregroup members who have tried the particular digital gift type within a specified time period. Coaching messages requesting personal information may filter caregroup members who are current with regard to their personal data.

Returning to the present example, an "Editions Count" numeric display field 1930 may provide an indication of the number of daily deliveries that were sent to the digital mailbox appliance user during the corresponding period being summarized. The administrating caregiver may provide text commentary in an "Initial Text" text input field 1940 explaining the newsletter or pointing our items of particular interest. Finally, before distributing the newsletter, the administrating caregiver may preview the newsletter by selecting the "Preview Newsletter" button 1950. Responsive to selection of the "Preview Newsletter" button 1950 a user interface screen may be presented to the administrating caregiver to allow the newsletter to be viewed in the form in which it will be distributed according to currently selected parameters, such as timeframe, recipients, etc.

Figure 20:
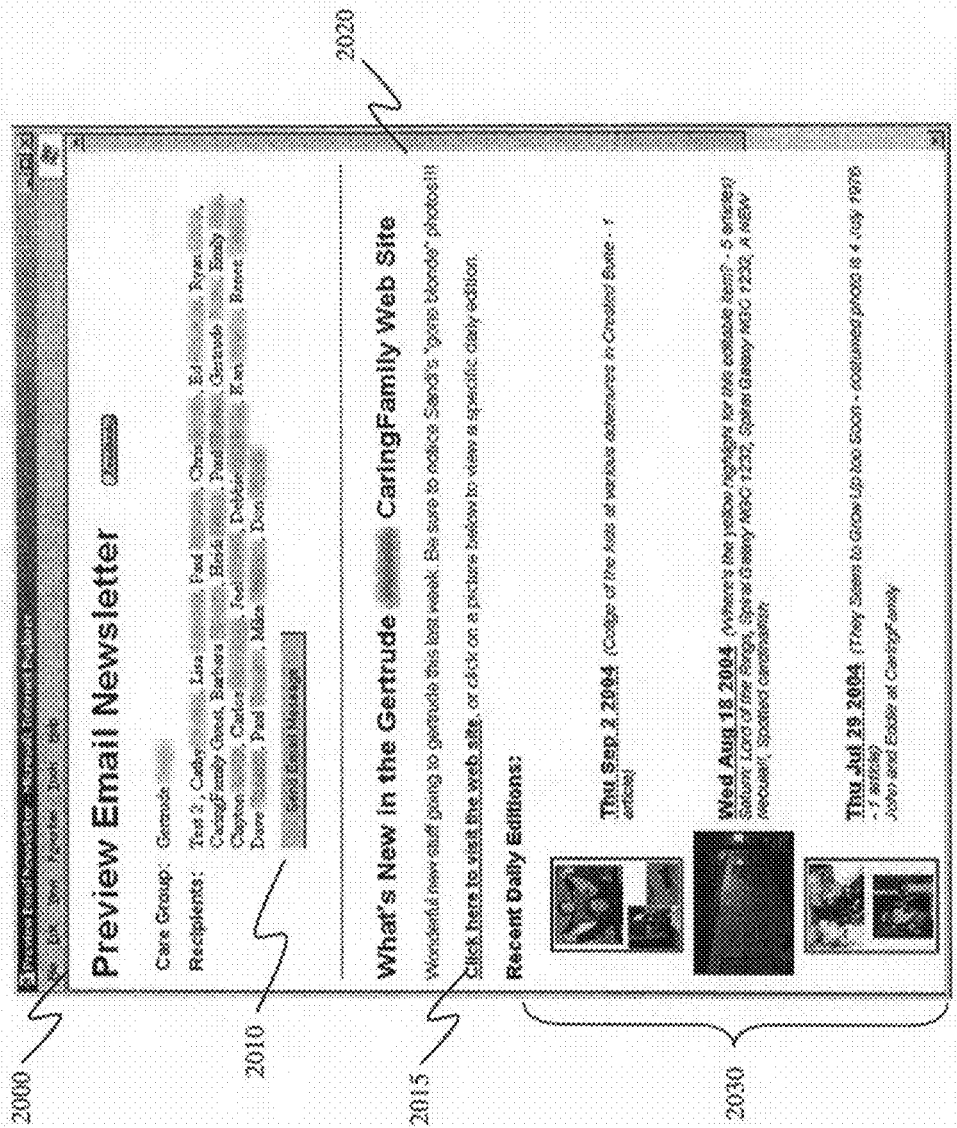
FIG. 20 illustrates a review coaching message user interface screen according to one embodiment of the present invention.

FIG. 20 illustrates a review coaching message user interface screen 2000 according to one embodiment of the present invention. In the present example, the administrating caregiver is provided an opportunity to review the newsletter prior to distribution to the list of recipients. The text message entered within the "Initial Text" text input field 1940 is displayed as introductory text 2020. A link 2015 is provided to facilitate easy access to the caregroup's website and encourage caregroup members to visit the website. The preview also includes a set of thumbnail image links 2030 to the various daily deliveries sent to the digital mailbox appliance user during the period at issue.

Figure 21:
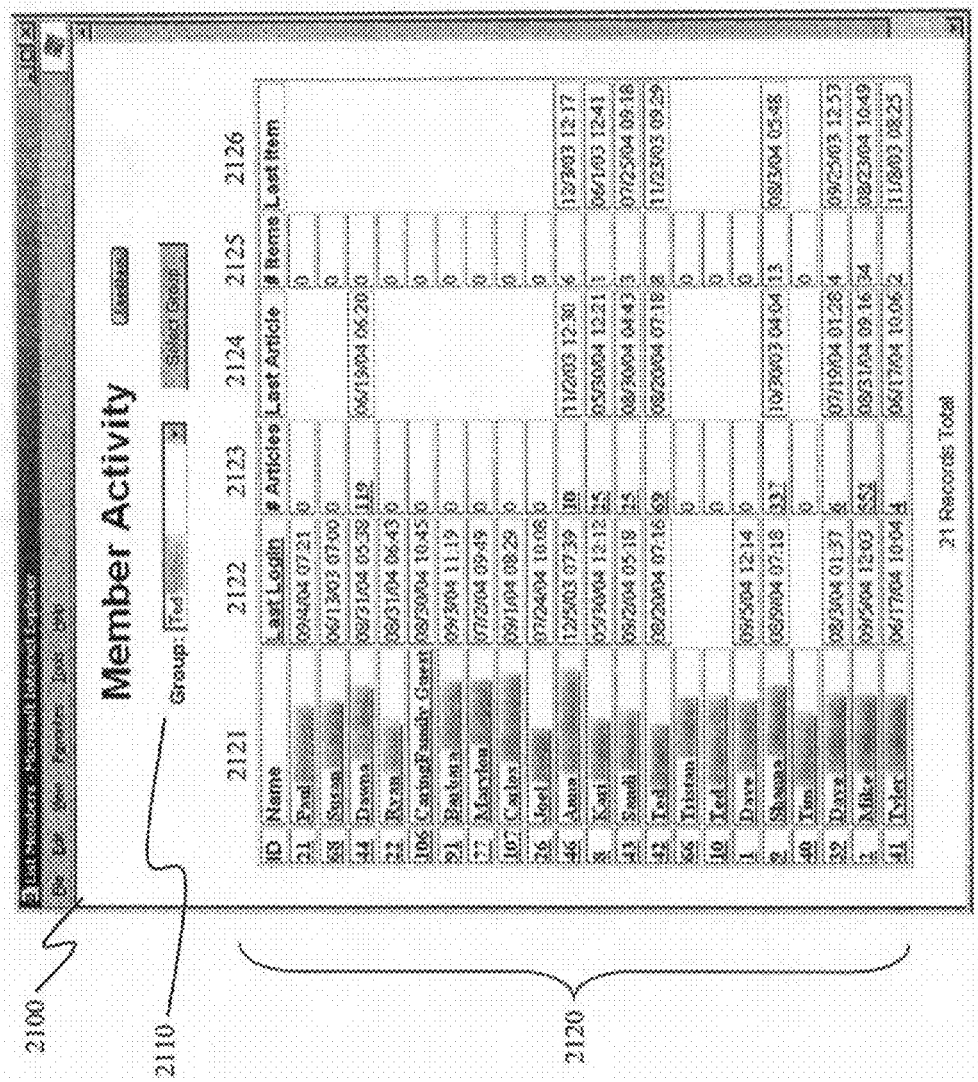
FIG. 21 illustrates a member activity user interface screen summarizing information regarding communications by members of a particular caregroup according to one embodiment of the present invention.

FIG. 21 illustrates a member activity user interface screen 2100 summarizing information regarding communications by members of a particular caregroup according to one embodiment of the present invention. In the present example, if the administrating caregiver participates in more than one caregroup, he/she may select one of the caregroups via a user interface input object, such as a caregroup dropdown list 2110.

Responsive to selection of the caregroup of interest, a member activity report 2120 may be displayed. In the present example, the member activity report 2120 includes a name column 2121, a last login column 2122, a number of articles column 2123, a last article column 2124, a number of items column 2125, and a last item column 2126. More or fewer columns may be provided depending upon predetermined or configurable settings associated with the member activity report 2120. For example, columns may be included for the individual rating values described above, e.g., effectiveness rating, intellectual stimulus rating, and activity inducement rating.

The member activity report 2120 may be used by administrating caregivers and/or customer service representatives of the communication service provider to make decisions regarding the types of coaching messages they would like to send and the targets of such coaching messages. In one embodiment, the administrating caregiver may sort the various columns 2121-2126 in ascending or descending order to assist processing of the information presented in the member activity report 2120. The administrating caregiver may also select an individual caregroup member from the member activity report 2120 to obtain detailed information concerning the selected caregroup member's communications and activities within the communication system. As described further below various other charts, meters, tables, and reports may be provided to the administrating caregiver(s) and/or customer service operators of the communication service provider. Such tools may be used to analyze the communications being exchanged among the caregroup members and the digital mailbox appliance user corresponding to the caregroup.

After having used various communications analysis tools, the administrating caregiver may select a coaching messages tab from his/her dashboard to choose from a collection of prompt editors. The administrating caregiver may create special coaching messages or edit the configurations of automated prompts (e.g. weekly summary, new gifts, . . . etc.).

Returning to the present example, the name column 2121 of the member activity report 2120 lists the members of the selected caregroup and the digital mailbox appliance user associated with the selected caregroup. The last login column 2122 indicates the time and date of the last caregroup website login by the corresponding caregroup member. The number of articles column 2123 indicates the number of articles that have been contributed to the daily delivery by the corresponding caregroup member allowing the administrating caregiver to evaluate the relative participation of the caregroup members. The last article column 2124 provides information regarding the date and time of the last article contributed to the daily delivery by the corresponding caregroup member allowing the administrating caregiver to see how current the particular caregroup members' participation in the daily delivery is. The number of items column 2125 provides information regarding the number of digital gifts delivered to the user of the digital mailbox appliance by the corresponding caregroup member. The last item column 2126 provides information regarding the date and time of the last digital gift sent by the corresponding caregroup member.

Figure 22:
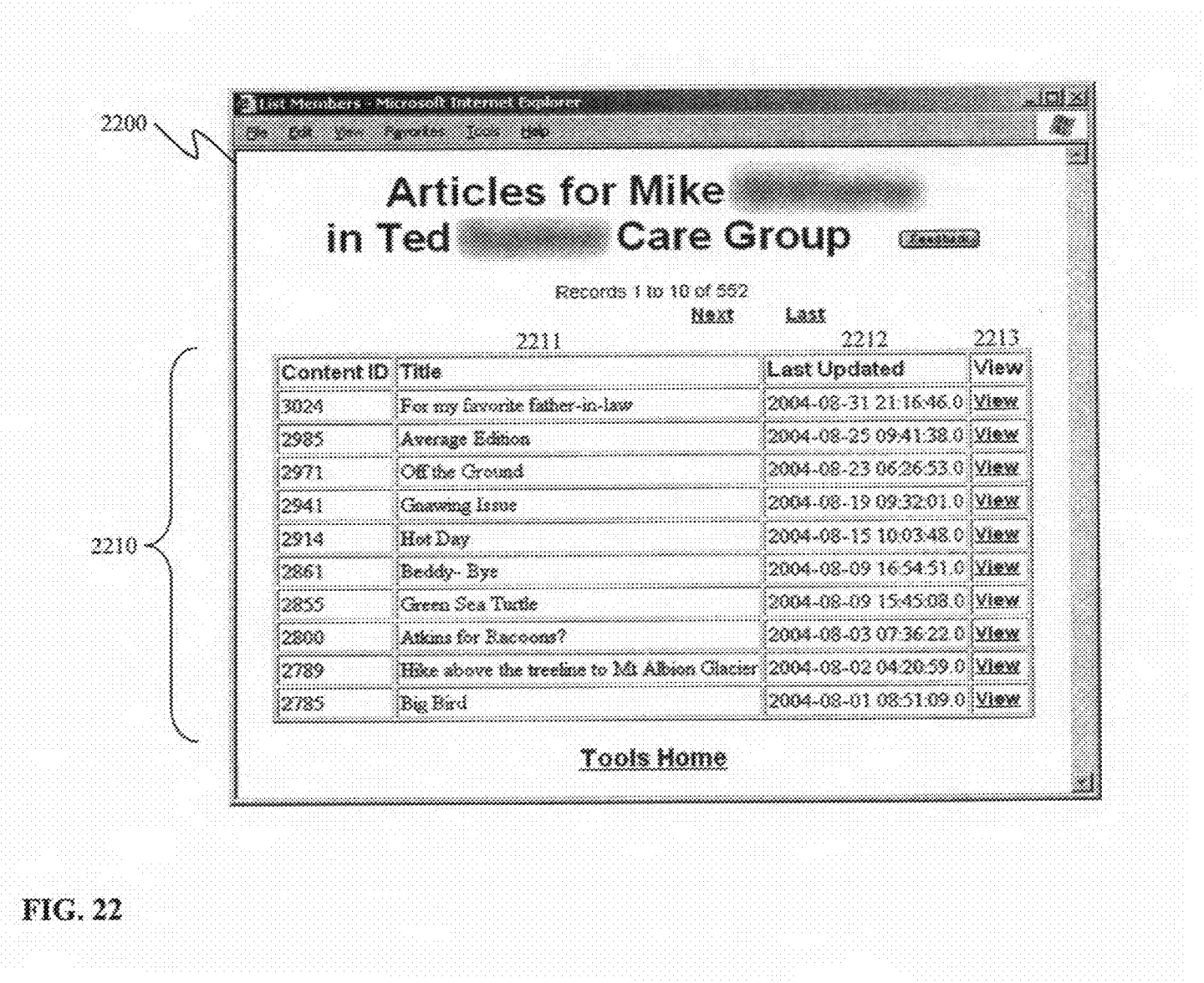

FIG. 22 illustrates a drill down member activity user interface screen 2200 listing communications by a specific member of a caregroup according to one embodiment of the present invention. In the present example, the drill down member activity user interface screen 2200 is presented responsive to selection of a particular caregroup member by the administrating caregiver from the member activity report 2120. According to one embodiment the drill down member activity user interface screen 2200 may display a drill down member activity report 2210 including a title column 2211, a last updated column 2212 and a view column 2213. As above, more or fewer columns may be provided depending upon predetermined or configurable settings associated with the drill down member activity report 2220. For example, columns may be included for one or more of individual affectiveness, intellectual stimulus and activity inducement rating values. Additionally, a column may be included relating to the various digital gifts sent by the caregroup member. Alternatively, a separate drill down member activity report relating to digital gifts may be included among the communication analysis tools provided to administrating caregivers.

In the present example, the title column 2211 of the drill down member activity report 2210 lists the titles of the various articles contributed by the selected caregroup member. The last updated column 2212 indicates the date and time the corresponding article was last updated. Finally, the view column 2213 provides a link to the corresponding article to allow the administrating caregiver to quickly review contributions by the selected caregroup member.

Figure 23:
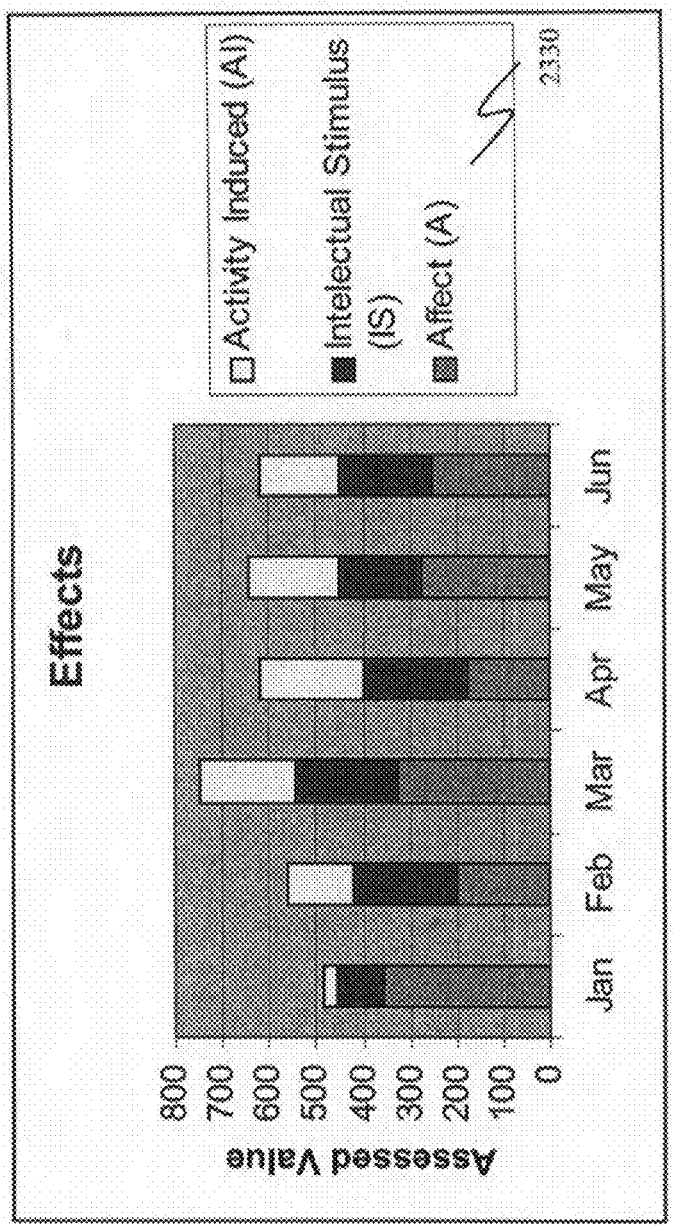
FIG. 23 illustrates an exemplary chart or dashboard monitor for effects of communications delivered to a particular elder that may be displayed within a user interface screen according to one embodiment of the present invention.

FIG. 23 illustrates an exemplary chart or dashboard monitor 2300 for effects of communications delivered to a particular elder that may be displayed within a user interface screen according to one embodiment of the present invention. According to the example illustrated, the effects chart 2300 visually depicts cumulative assessed rating values in the form of a bar chart for three exemplary categories of effects, i.e., activity induced 2310, intellectual stimulus 2320, and affectiveness 2330, by month. Various other charting formats may be used, e.g., histogram, pie chart, etc., and differing aggregation timeframes may be used, e.g., day, week, year, etc. Charting and/or timeframe parameters may be predefined and user selectable or configurable by the administrating caregiver.

Figure 24:
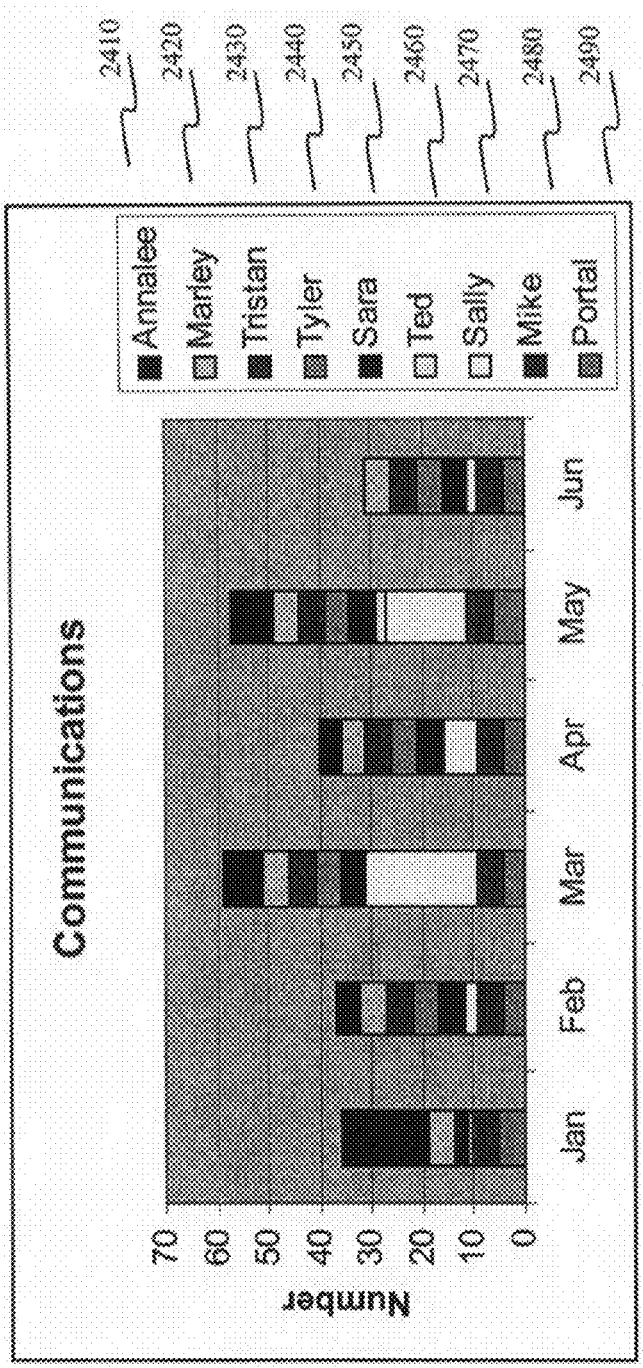
FIG. 24 illustrates an exemplary chart or dashboard monitor of communications delivered to a particular elder by caregroup member that may be displayed within a user interface screen according to one embodiment of the present invention.

FIG. 24 illustrates an exemplary chart or dashboard monitor 2400 of communications delivered to a particular elder by caregroup member that may be displayed within a user interface screen according to one embodiment of the present invention. According to the example illustrated, the communications chart 2300 visually depicts the cumulative number of communications delivered to the particular elder in the form of a bar chart by caregroup member 2410-2490 and by month. Various other charting formats may be used, e.g., histogram, pie chart, etc., and differing aggregation timeframes may be used, e.g., day, week, year, etc. Charting and/or timeframe parameters may be predefined and user selectable or configurable by the administrating caregiver.

Figure 25:
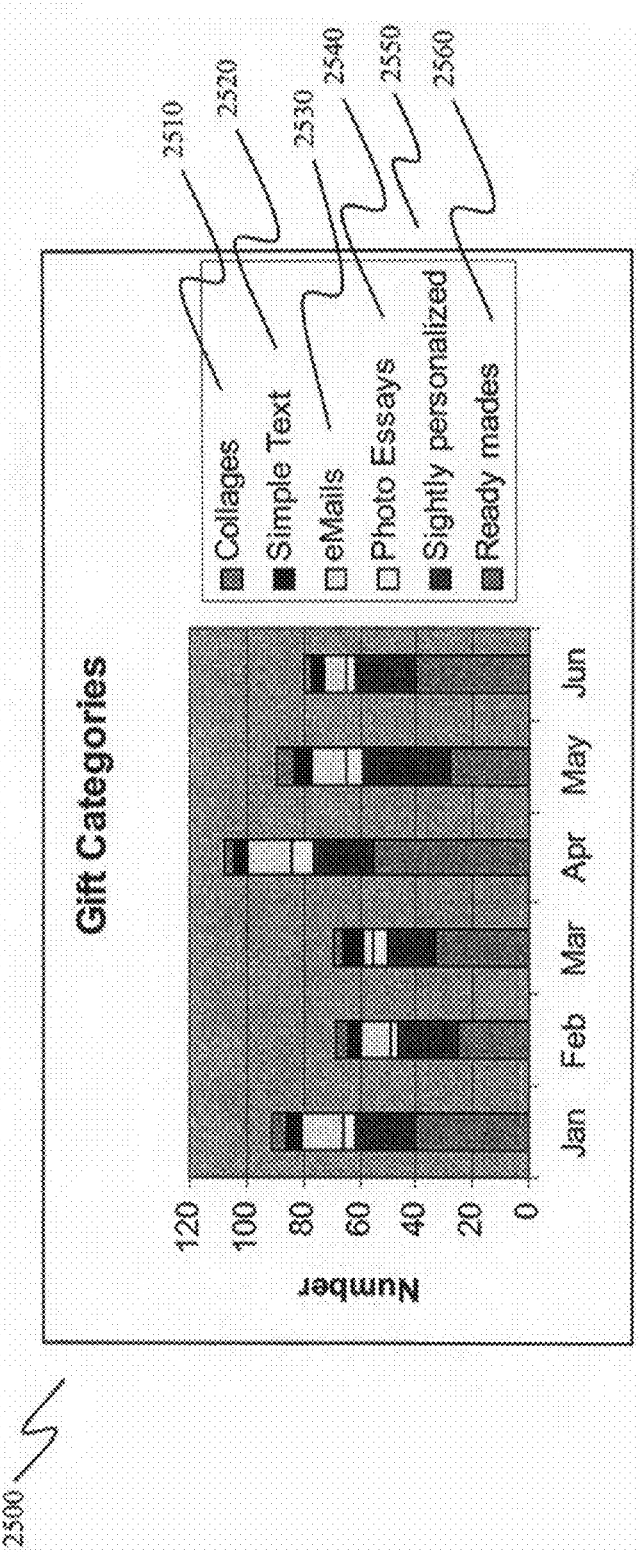
FIG. 25 illustrates an exemplary chart or dashboard monitor of digital gifts by category delivered to a particular elder that may be displayed within a user interface screen according to one embodiment of the present invention.

FIG. 25 illustrates an exemplary chart or dashboard monitor 2500 of digital gifts by category delivered to a particular elder that may be displayed within a user interface screen according to one embodiment of the present invention. According to the example illustrated, the gift categories chart 2500 visually depicts the cumulative number of digital gifts delivered to the particular elder in the form of a bar chart by digital gift category 2510-2560 and by month. Various other charting formats may be used, e.g., histogram, pie chart, etc., and differing aggregation timeframes may be used, e.g., day, week, year, etc. Charting and/or timeframe parameters may be predefined and user selectable or configurable by the administrating caregiver.

Figure 26:
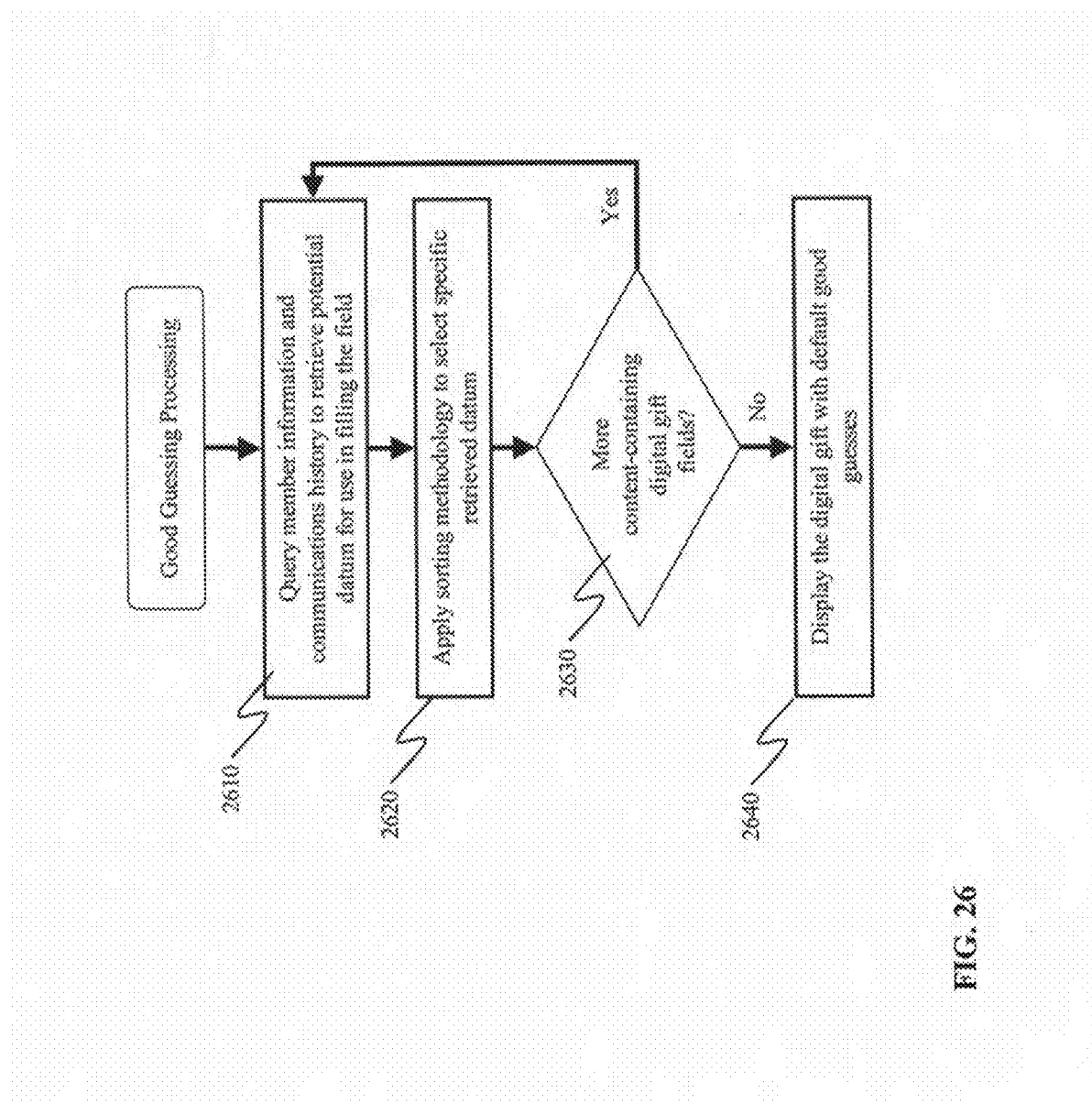
FIG. 26 is a flow diagram illustrating a method of performing good guessing according to one embodiment of the present invention.

FIG. 26 is a flow diagram illustrating a method of performing good guessing according to one embodiment of the present invention. According to various embodiments of the present invention, the communication system platform, via caregroup websites, for example, may provide distinct editors for each digital gift type. In one embodiment, in order to facilitate the creation of digital gifts and encourage caregroup members to participate in digital gift giving to the digital mailbox appliance user associated with the caregroup, techniques are employed to establish intelligent defaults for content fields of digital gifts. These techniques are referred to herein as "good guessing."

Examples of content fields include an eCard image, the greeting title text, and the 'interior' sentiment and signature text. According to one embodiment, good guessing is predicated on data collected by the communication service provider about the family or caregroup and/or context of the communication or the type of communication. For example, various information that may be used during good guessing processing includes one or more of the following: the caregroup member's biographic information; information regarding communications history between one or more members of the caregroup and the focus of the caregroup, such as the caregroup's specific communications activities, the specific communication history between the caregroup member and the user of the digital mailbox appliance; ascertained preferences of the target of the caregroup, the content created by the caregroup and/or the particular caregroup member, the type of the digital gift, and/or any survey data collected regarding their "out of band communications" (e.g., phone calls, emails between caregroup members that are not though the communication service provider, physical visits, etc.). Additionally, images and text included in digital gifts have associated keywords that may be used in categorization schemes for specific editors, such as a birthday card editor. Content supplied by the communication service provider and used by caregroup members may also have value in a search for a good guess.

According to the present example, each content-containing component of a digital gift has an associated query that is used to select from content items. Content items have fields for the image URL, subtitle text, commenting text, source (e.g., caregroup member, communication service provider staff), date, key-words (used for categories, etc.), seen (date) over which the queries are run. At block 2610, the data collected and maintained in the communication service provider's central service data base is queried to retrieve potential datum for use in filling the current content containing digital gift field. For example, the query may be against the caregroup member's information and communications history with the user of the digital mailbox appliance and/or with others. Various other examples of specific data that may be collected for use in good guessing is described further below.

At block 2620, a sorting methodology is applied to the retrieved datum to select a specific retrieved datum for inclusion in the current content-containing component of the digital gift. Various sorting techniques may be employed, such as goodness of fit to various numerical assessments, least recently used, randomization, etc.

At decision block 2630, a determination is made whether more content-containing components remain that have not been assigned a good guessing default. If so, then processing continues with block 2610; otherwise, processing proceeds to block 2640.

At block 2640, the selected digital gift is displayed within the corresponding digital gift editor and each content-containing field of the digital gift is filled-in with the previously guessed content.

As indicated above, good guessing relies upon data collected and maintained by the communications service provider. Examples of specific data collected includes information about caregroup members (such as that entered into a member personal information user interface screen 2700 like that depicted in FIG. 27), about the elder/family schedule (such as that entered into an elder's schedule user interface screen 2800 like that depicted in FIG. 28), about specific communications (such as a photo essay 2900 like that depicted in FIG. 29), from occasional surveys that might be conducted. Data from such surveys might include recollection of phone calls, recollection of member-member emailing outside of the communication system platform and recent visits to the elder, including, duration, topics discussed, . . . etc.

Figure 27:
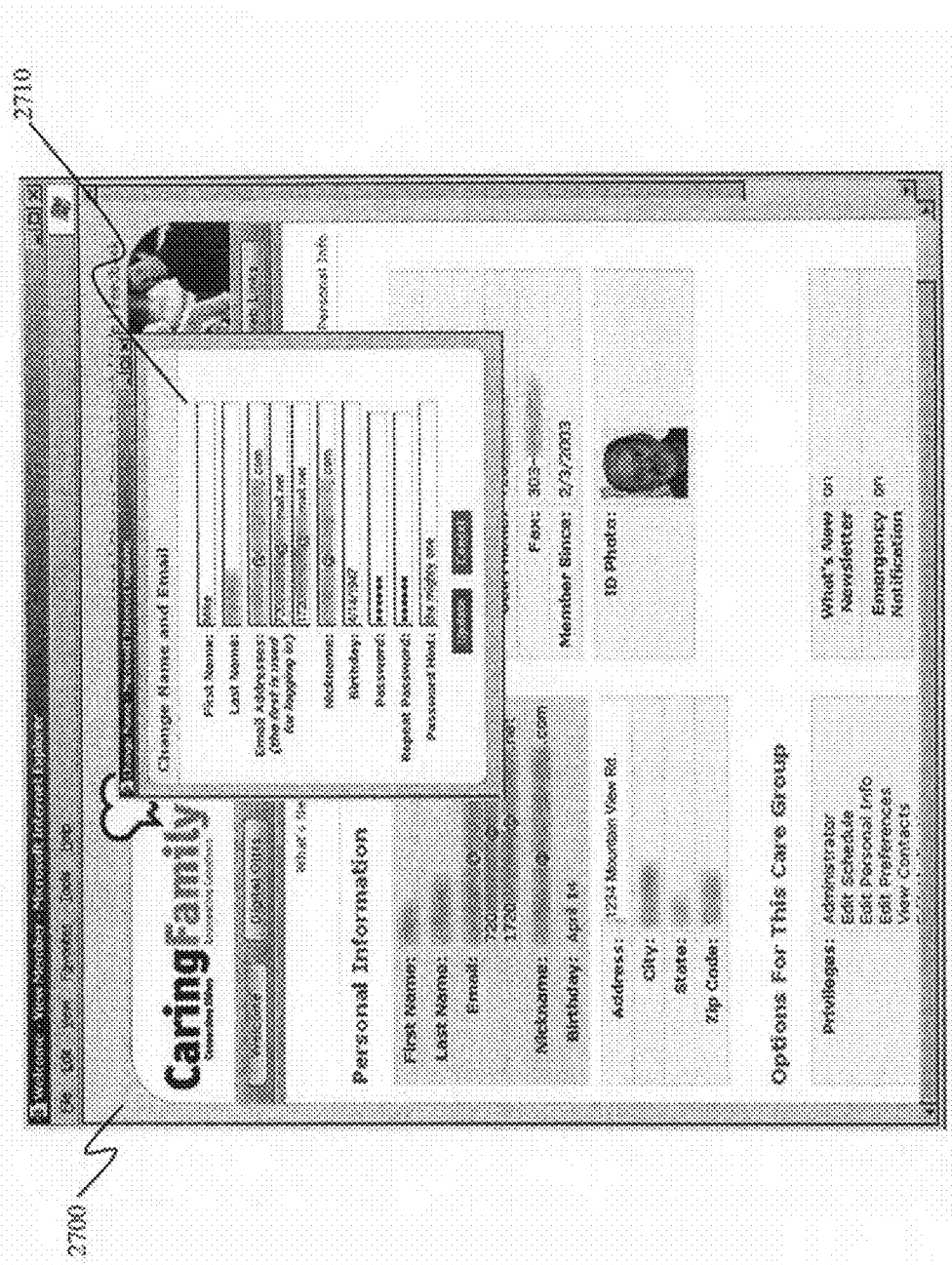
FIG. 27 illustrates a member personal information user interface screen according to one embodiment of the present invention.

FIG. 27 illustrates a member personal information user interface screen 2700 according to one embodiment of the present invention. Caregroup members or administrating caregivers may enter various information, such as name, address, phone numbers, email addresses (including cameraphone addresses), birthdate (the year is recorded but may not be posted), ID photo(s), opt-in coaching permissions, editing privileges, . . . etc.), nick names, . . . etc., via a pop-up editor (or pop-ups) as shown 2710 and as described further below.

Figure 28:
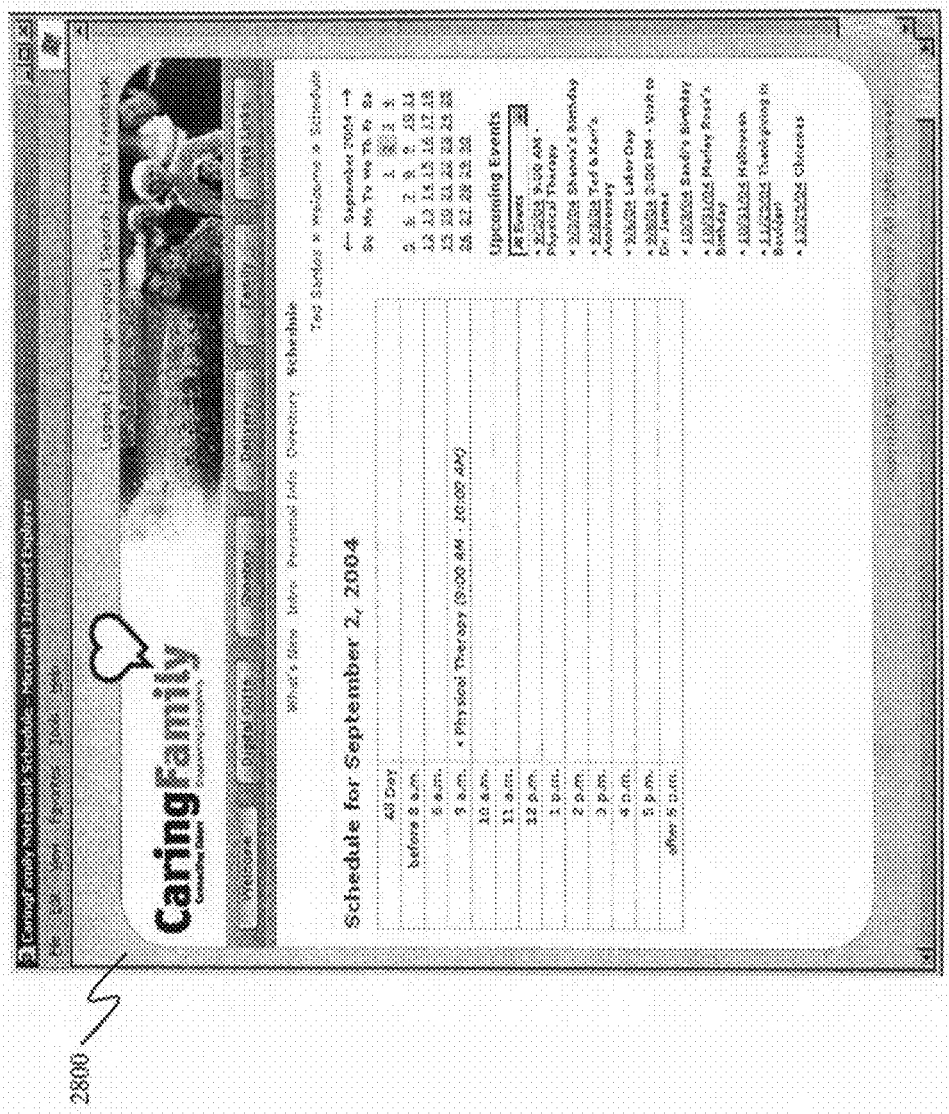
FIG. 28 illustrates an elder's schedule user interface screen according to one embodiment of the present invention.

FIG. 28 illustrates an elder's schedule user interface screen 2800 according to one embodiment of the present invention. In one embodiment, information regarding the elder's and/or the family's schedule may be provided via user interface screen 2800. Examples of information that might be entered and maintained on behalf of a family caregroup includes family recognized holidays, birthdays (from the core member data), events (e.g., a Thanksgiving reunion), doctor's appointments, . . . etc. Information here can be used to drive various coaching opportunities to both the elder and caregroup members.

Figure 29:
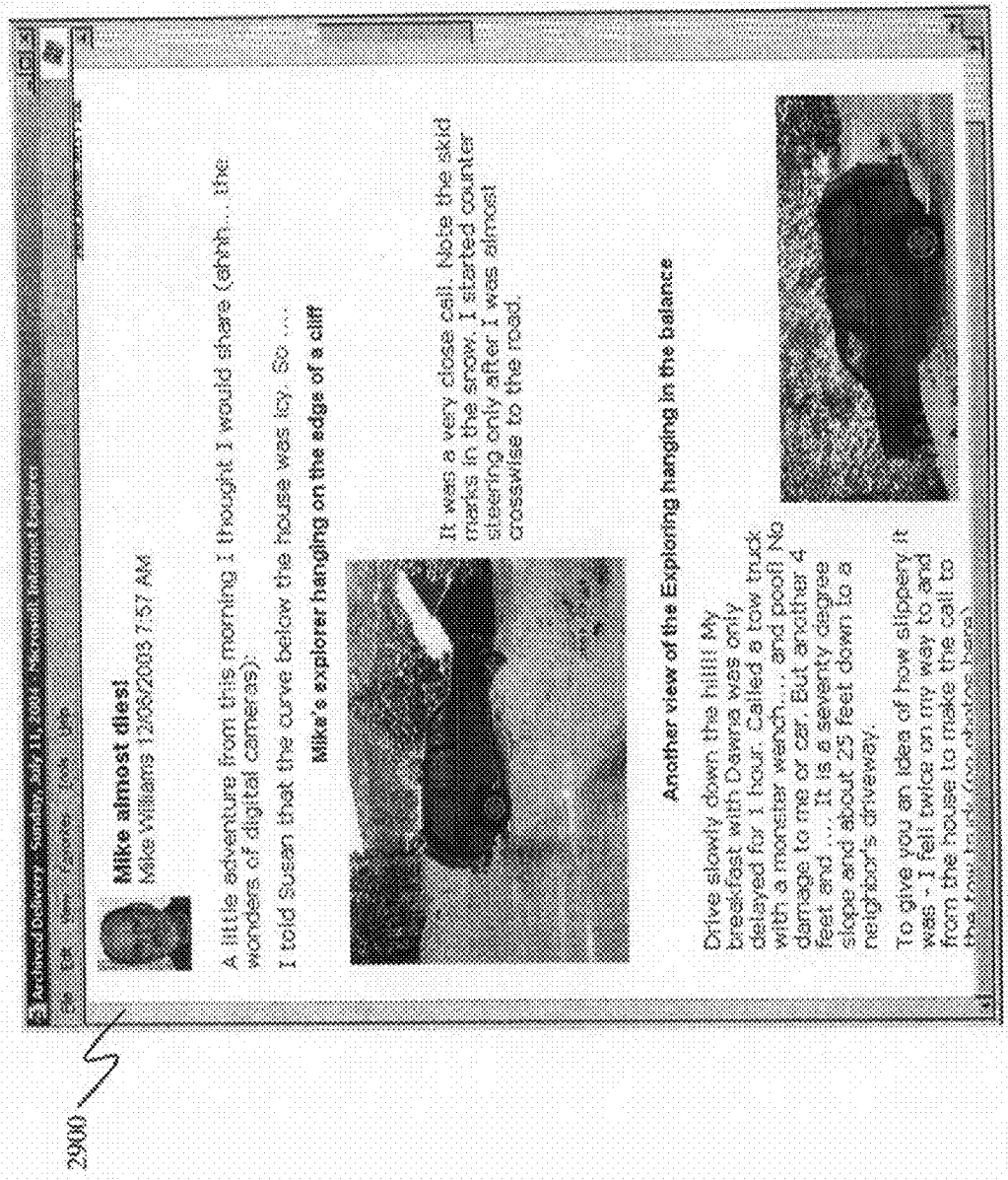
FIG. 29 illustrates an example of a user interface screen depicting a photo essay type digital gift according to one embodiment of the present invention.

FIG. 29 illustrates an example of a user interface screen 2900 depicting a photo essay type digital gift according to one embodiment of the present invention. According to one embodiment, the communication service provider collects and maintains information about specific communications in order to facilitate charting and reporting to the administrating caregiver(s) and to support good guessing.

Such information collection is simplified by the fact that all digital gifts delivered are generated from a database record created by the caregroup member's interactions with a specific digital gift editor, or parsing of a traditional email. The more precise the records, the more helpful the coaching and good guessing will be.

Information that may be collected regarding a particular digital gift includes the type of message (e.g., digital gift), header information (such as source, recipient(s), date, title, etc.), gift type (e.g., photo essay), creation date, delivery date, images used (both family content and content supplied by the communication service provider), various categories of text (such as that associated with specific images), . . . etc. Images typically have subtitle and body text associated with them. This text often contains information that can be correlated and used in good guessing.

Figure 30:
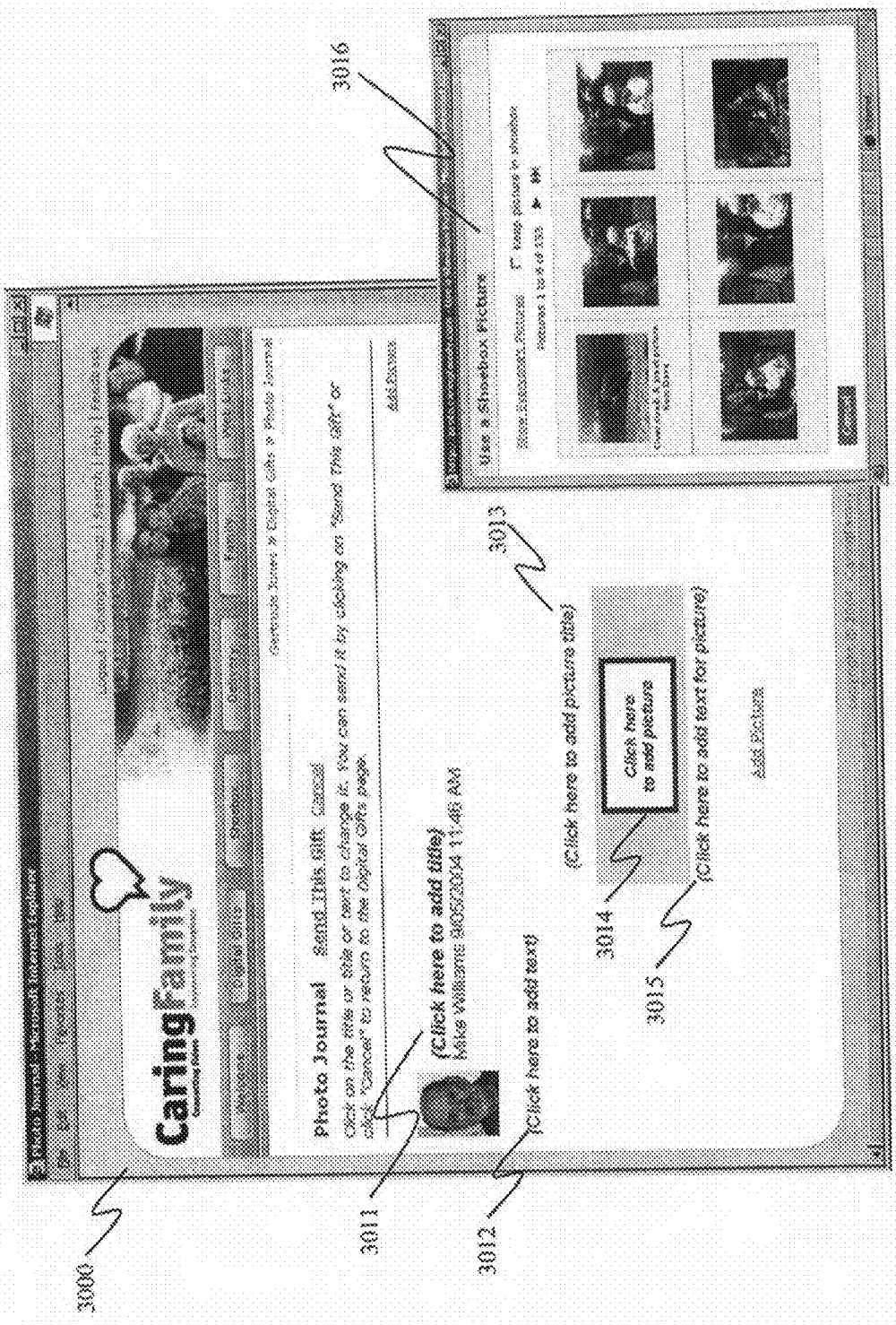
FIG. 30 illustrates a user interface screen depicting an initial (blank) photo essay (or photo journal) type of digital gift with embedded edit stimulus markers according to one embodiment of the present invention.

FIG. 30 illustrates a user interface screen 3000 depicting an initial (blank) photo essay 3010 (or photo journal) type of digital gift with embedded edit stimulus markers 3011-3115 according to one embodiment of the present invention. Using the popup editor mechanism, each field presents (one or more) presentation components. Thus, responsive to selection of an editable field, such as 3014, by the end user, an image editor 3016 might present a light table with image content supplied by the communication service provider, or family images or an image uploading tool.

Figure 31:
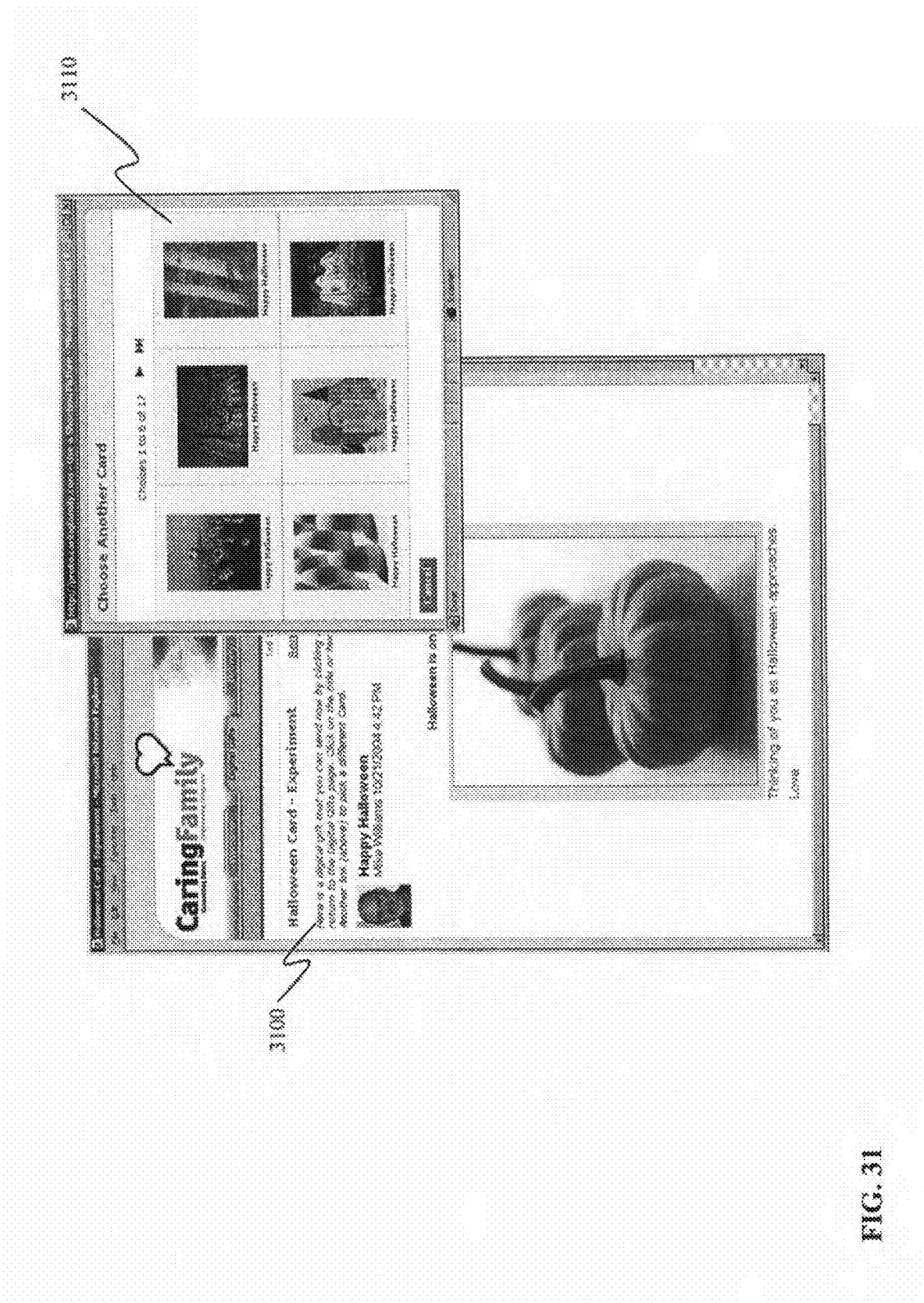
FIG. 31 illustrates a user interface screen depicting a personalizable ready made eCard type of digital gift resulting from good guessing according to one embodiment of the present invention.

FIG. 31 illustrates a user interface screen depicting a personalizable ready made eCard type of digital gift resulting from good guessing according to one embodiment of the present invention. Within the basic eCard editor 3100 the system has guessed that a Halloween card is what is likely to be appropriate and in particular a colorful image of Halloween gourds has been guessed. It is highlighted yellow because the user has passed the mouse over the image. Selecting the image brings up a light table of likely alternative images 3110. Selecting and image from the light table of likely alternative images 3110 would replace the current eCard image.

Figure 32:
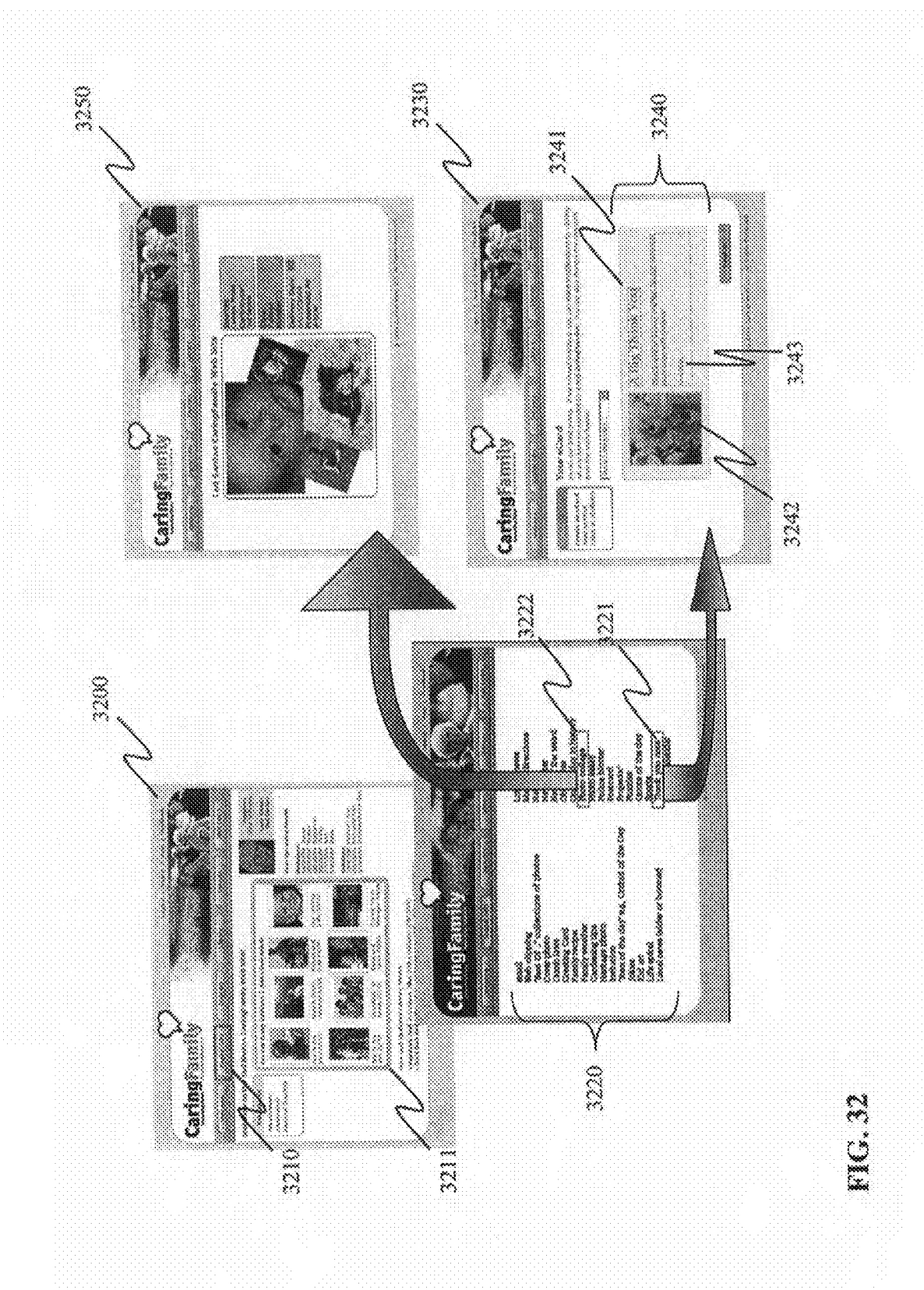
FIG. 32 illustrates various user interface screen shots, selection from a collection of digital gifts and good guessing defaults according to one embodiment of the present invention.

FIG. 32 illustrates various user interface screen shots, selection from a collection of digital gifts and good guessing defaults according to one embodiment of the present invention. According to the present example, a caregiver has logged into a caregroup VPN and is taken to a home page 3200 for the caregroup website, e.g., the "What's new?" page. Here the caregroup member may be presented with cover photo thumbnails 3211 from the last week's daily deliveries that have already been delivered to the elder. Selecting one of the thumbnails 3211 retrieves and presents an electronic rendering of the corresponding daily delivery. Selecting a digital gifts button 3210 (2nd from the left on the navigation bar) the caregroup member is presented with a list of possible digital gifts 3220 to send the elder (or another member of the caregroup).

Upon selecting a digital gift type, a custom editor for the selected digital gift type is opened. For example, if the caregroup member indicates he/she would like to send a thank you note by selecting the "Thank you note" hyper link 3221, then a thank you note editor 3230 is presented with a thank you note 3240 containing good guessing defaults for the title 3241, picture 3242, and sentiment 3243 as described earlier. The good guessing defaults may be changed by the caregroup member by selecting the particular content containing element and replacing it with personalized content. Alternatively, if the caregroup member indicates he/she would like to send a photo collage by selecting the "Photo collage" hypertext link 3222, then a photo collage editor 3250 is presented with recently uploaded photos from the caregroup member's camera phone. Again, the caregroup member may edit the digital gift before sending it by adding, deleting and/or replacing photos, for example.

Figure 33:
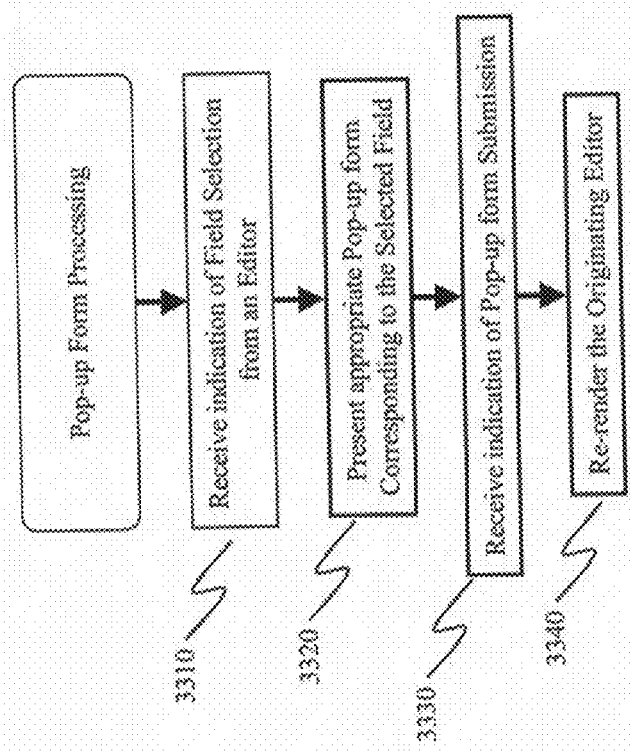
FIG. 33 is a flow diagram illustrating a method of interacting with pop-up forms according to one embodiment of the present invention.

FIG. 33 is a flow diagram illustrating a method of interacting with pop-up forms according to one embodiment of the present invention. In the example depicted, pop-up form processing begins at block 3310 responsive to selection of a field or group of fields by a caregroup member from within an editor, such as a digital gift editor. At block 3310, an indication of the selected field or group of fields is received. At block 3320, a pop-up form corresponding to the selected field or group of fields is presented to the caregroup member. After the caregroup member has made the appropriate choices and/or provided the requested information and submitted the pop-up form, at block 3330, an indication is received by the originating editor that the pop-up form has been completed. Then, at block 3340, the originating editor is re-rendered based upon the information submitted via the pop-up editor thereby giving the caregroup member real-time feedback regarding the effects his/her decisions/selections have on a digital gift being created, for example.

Figure 34:
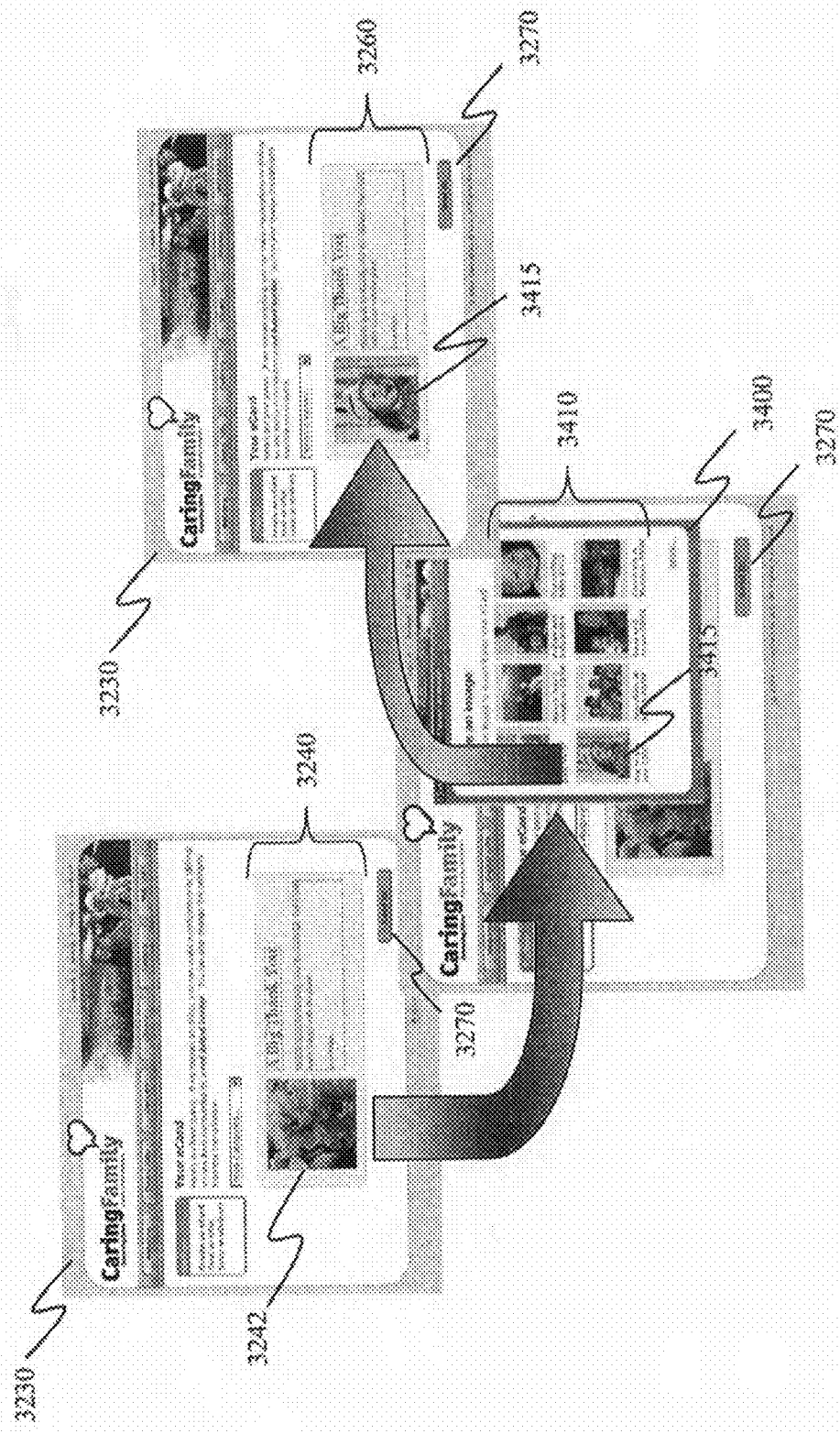
FIG. 34 illustrates customization and re-rendering of a pop-up in the context of a note editor according to one embodiment of the present invention.

FIG. 34 illustrates customization and re-rendering of a pop-up in the context of a note editor according to one embodiment of the present invention. Continuing with the example discussed with reference to FIG. 32, upon receiving an indication by a caregroup member that he/she would like to create a thank you note, the "thank you note" editor 3230 is presented with "good guesses" regarding appropriate content for fields, such as a likely image for picture field 3232, within the thank you note 3240. Note the "Send it!" button 3270 in the lower right hand corner of the thank you note editor 3230. The thank you note 3240 is ready to go if the caregroup member is satisfied with the defaults selected by the good guessing process. If the caregroup member likes what they see they can send the thank you note 3240 immediately.

As described earlier, the thank you note editor 3230 employs good guessing to supply the likely image, text for the title, and even a draft sentiment (derived from the message type, communications histories of both the caregiver and the elder, and numbers of other parameters). If the caregroup member would like to revise one of the editable components, such as the image for picture field 3232, they are highlighted in some manner to indicate their editability, for example, by being bordered with a dashed red outline. In the present example, the caregroup member has selected the picture field 3232 to chose a different image. Selecting the picture field 3232 brings up a pop-up window 3400 providing a table of options 3410. Choosing a personal picture of the grand daughter 3415 from the table of options 3410 causes the thank you note editor 3230 to re-render the revised thank you note 3260 (which now includes the selected image 3415 in the picture field 3232) to send or modify further.

Figure 35:
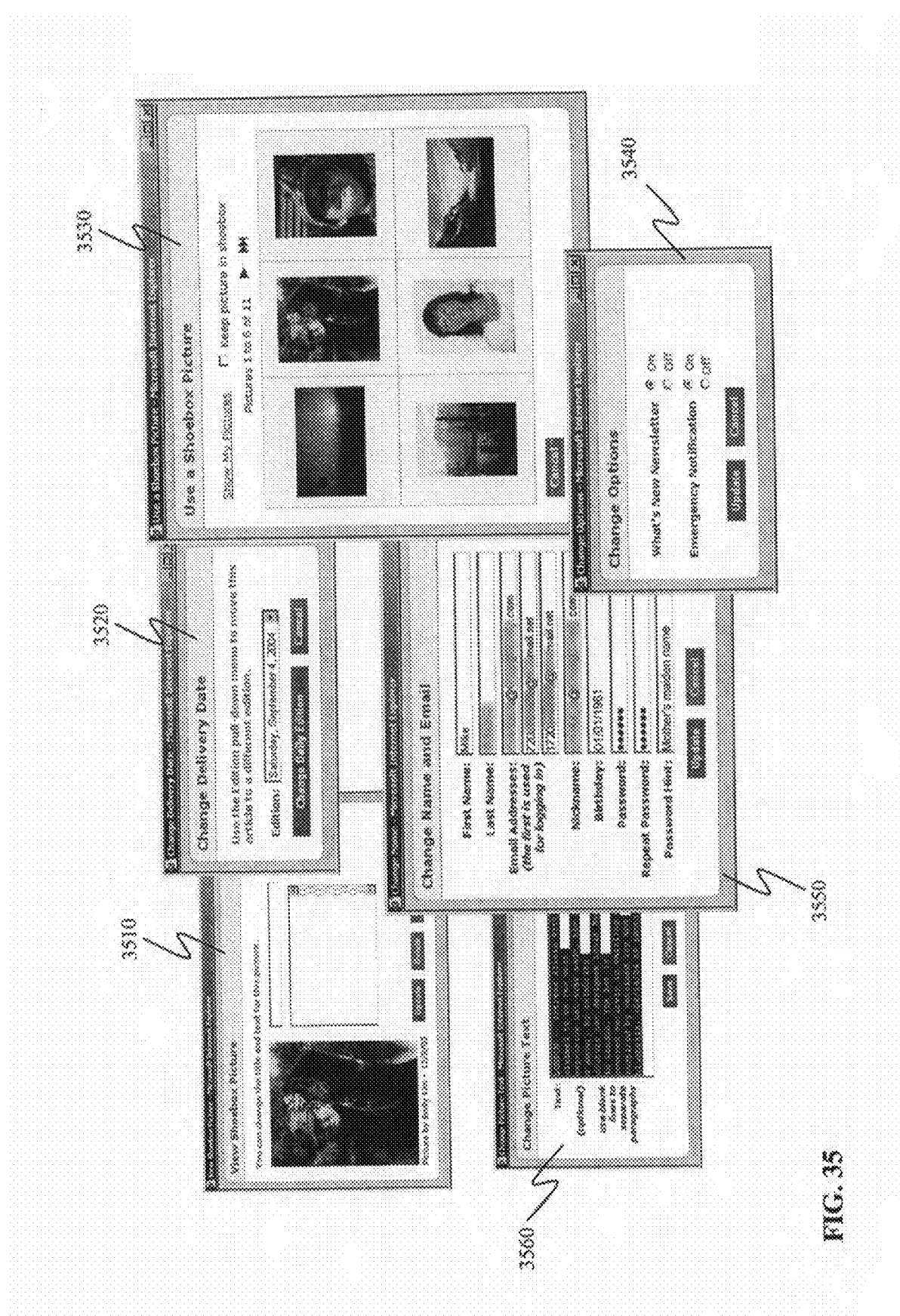
FIG. 35 illustrates examples of various pop-ups according to one embodiment of the present invention.

FIG. 35 illustrates examples of various pop-ups 3510-3560 according to one embodiment of the present invention. Pop-up 3510 is an example of a pop-up window that may be used to change the title and text associated with a picture in the caregroup member's shoebox. Pop-up 3520 is an example of a pop-up window that may be used to change the delivery date of an article submitted by a caregroup member for publication in a daily delivery. Pop-up 3530 is an example of a pop-up window that may be used to allow a caregroup member to select a picture from the caregroup member's shoebox. Pop-up 3540 is an example of a pop-up window that may be used to provide an administrative caregiver with mutually exclusive options from which to select for configuring various parameters within the caregroup VPN. Pop-up 3550 is an example of a pop-up window that may be used to edit groups of related fields, such as biographic information and contact information. Pop-up 3560 is an example of a pop-up window that may be used to change text associated with a picture in the context of a photo essay or photo journal digital gift, for example.

Figure 36:
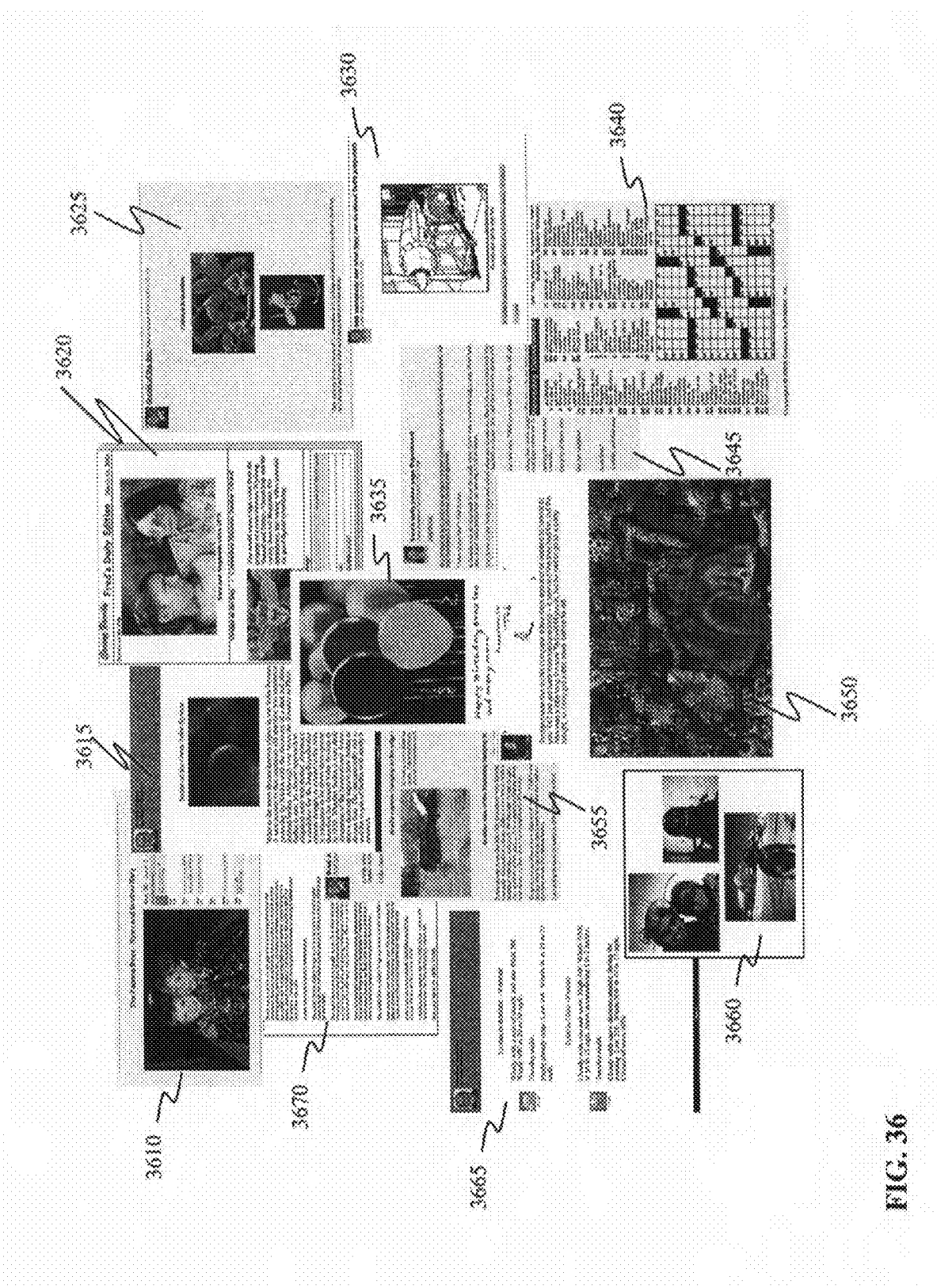
FIG. 36 illustrates examples of various digital gifts according to one embodiment of the present invention.

FIG. 36 illustrates examples of various digital gifts according to one embodiment of the present invention in the form of a collage including a personalized weekly calendar digital gift 3610, an astronomy picture of the day digital gift 3615, a daily delivery publication digital gift 3620, an orchid of the day digital gift 3625, an annotated cartoon digital gift 3630, a personalized (eCard) birthday card digital gift 3635, a crossword puzzle digital gift 3640, a daily jokes digital gift 3645, a kid art digital gift 3650, a photo essay digital gift 3655, a photo collage digital gift 3660, a family weather digital gift 3665, a web clipping digital gift 3670.

As should be appreciated, various art and projects from the elder's grand children or other relatives serve as particularly valued contributions to the daily delivery. In pilot studies, both the elder and all the adult caregroup members remarked in surveys on their particular pleasure in these occasional contributions.

A favorite family photo with the next week's schedule of events, maintained as part of the Discussion site, for example, may serve as the raw material. Any family member can use the calendar Digital Gift to provide a calendar that the elder can print out and post. The weekly calendar is of particular interest because it may serve as a mechanism for family members to coach the elder for upcoming events such as doctor's appointments, family visits, the monthly hair appointment, physical therapy, . . . etc.

While embodiments of the invention have been illustrated and described, it will be clear that the invention is not limited to these embodiments only. Numerous modifications, changes, variations, substitutions, and equivalents will be apparent to those skilled in the art, without departing from the spirit and scope of the invention, as described in the claims.

What is claimed is:

1. A method of supporting routing of electronic communications among a caregroup, the method comprising:
   receiving, by a central service database of a communication service provider, information defining the caregroup, including members of the caregroup, a target of the caregroup and one or more administrating caregivers of the caregroup;
   receiving, by a scan upload module operable within a distribution server of the communication service provider, a digital representation of an annotated routing form from a hardcopy-based email appliance located remotely from the distribution server, the hardcopy-based email appliance operable to both accept hardcopy input from and produce hardcopy output for the target of the caregroup, the annotated routing form having a particular form type of a plurality of predetermined form types, one or more portions of the digital representation of the annotated routing form intended for email delivery to one or more of the members of the caregroup, the annotated routing form including thereon a set of item identification marks;
   reading, by an automated dispatching module operable within the distribution server, the set of item identification marks from the digital representation of the annotated routing form;
   determining, by the automated dispatching module, the particular form type of the annotated routing form and one or more characteristics of the annotated routing form based on the set of item identification marks, the one or more characteristics of the annotated routing form including information regarding a location of an address sector within the annotated routing form;
   attempting, by the automated dispatching module, to determine the one or more members of the caregroup by processing a portion of the digital representation corresponding to the location of the address sector;
   composing, by the automated dispatching module, a digital representation of a resulting message based at least in part upon the particular form type;
   if said attempting, by the automated dispatching module, to determine the one or more members of the caregroup is successful, then distributing, by the automated dispatching module, the digital representation of the resulting message by associating the digital representation of the resulting message with an email message addressed to email accounts of each of the one or more members of the caregroup;
   if said attempting, by the automated dispatching module, to determine the one or more members of the caregroup is inconclusive, then submitting, by the automated dispatching module, the digital representation of the annotated routing form to a human augmented dispatch system; and
   wherein the scan upload module and the automated dispatching module are implemented in one or more computer processors and one or more computer-readable storage media of the distribution server, the one or more computer-readable storage media having instructions tangibly embodied therein representing the scan upload module and the automated dispatching module that are executable by the one or more computer processors.

2. The method of claim 1, further comprising:
   after said receiving, by a scan upload module operable within a distribution server of a communication service provider, a digital representation of an annotated routing form, receiving, by the scan upload module, a digital representation of a subsequent page of correspondence; and
   determining, by the automated dispatching module, the digital representation of the subsequent page of correspondence is to be distributed to the one or more members of the caregroup as part of the digital representation of the resulting message.

3. The method of claim 2, wherein said determining, by the automated dispatching module, the digital representation of the subsequent page of correspondence is to be distributed to the one or more members of the caregroup as part of the digital representation of the resulting message is based upon (i) a lack of identifiable addressing information associated with the subsequent page of correspondence, and (ii) a difference in time between (a) a time stamp associated with the digital representation of the subsequent page of correspondence and (b) a time stamp associated with the digital representation of the annotated routing form being within a predetermined threshold.

4. The method of claim 1, further comprising:
   parsing, by the automated dispatching module, the digital representation of the annotated routing form based on the particular form type; and
   wherein said attempting, by the automated dispatching module, to determine the one or more members of the caregroup includes performing one or more image processing techniques to compare one or more portions of the address sector within the digital representation of the annotated routing form to corresponding portions of the address sector within an original version of the particular form type.

5. The method of claim 1, wherein the digital representation of the resulting message comprises a digital gift suitable for printing.

6. The method of claim 5, wherein aesthetic appearance of the digital gift is enhanced by including within the digital representation of the resulting message a background design associated with the particular form type.

7. The method of claim 1, wherein the one or more characteristics include information regarding a physical location within the annotated routing form of one or more of a handwriting sector and a choice sector.

8. The method of claim 7, further comprising retrieving content from a database for inclusion in the digital representation of the resulting message based upon one or more content selections indicated within the choice sector of the annotated routing form.

9. The method of claim 1, wherein said composing, by the automated dispatching module, a digital representation of a resulting message further comprises extracting, by the automated dispatching module, the one or more portions from the digital representation of the annotated routing form and including digital representations of the one or more extracted portions within the digital representation of the resulting message.

10. The method of claim 1, wherein the set of identification marks comprises one or more of a barcode and a semicode.

11. A method comprising:
receiving, by a communication service dashboard module operable within a web server of a communication service provider, information defining a caregroup, including members of the caregroup, a target of the caregroup and one or more administrating caregivers of the caregroup;
receiving, by a digital gift editor module operable within a web server of the communication service provider from a member of the caregroup, an indication of a digital gift desired to be generated and caused to be delivered in hardcopy form to a hardcopy-based email appliance of the target of the caregroup, the hardcopy-based email appliance operable to both accept hardcopy input from and produce hardcopy output for the target of the caregroup;
for each content-containing component of the digital gift, selecting, by the digital gift editor module, default content items based upon one or more of biographical information previously supplied by one or more members of the caregroup, information regarding communications history between one or more members of the caregroup and the target of the caregroup, ascertained preferences of the target of the caregroup, and a type of the digital gift;
allowing, by the digital gift editor module, the caregroup member to immediately initiate delivery of the digital gift with the selected default content items or personalize the digital gift prior to delivery by presenting the digital gift within a corresponding digital gift editor; and
wherein the communication service dashboard module and the digital gift editor module are implemented in one or more computer processors and one or more computer-readable storage media of the web server, the one or more computer-readable storage media having instructions tangibly embodied therein representing the communication service dashboard module and the digital gift editor module that are executable by the one or more computer processors.

12. The method of claim 11, wherein content items from which the default content items are selected are stored in a database, and wherein said selecting, by the digital gift editor module, default content items further comprises running one or more queries on fields associated with the content items.

13. The method of claim 12, further comprising applying a sorting methodology to results of the one or more queries.

14. The method of claim 13, wherein the sorting methodology comprises one or more of randomization, least recently used, and alphabetical.

15. A method of facilitating caregroup coaching, the method comprising:
receiving, by a communication service dashboard module operable within one or more computer systems of a communication service provider, information defining a family support network, including members of the family support network, a target of the family support network and one or more administrating caregivers of the family support network;
the communication service provider maintaining information regarding events of significance to the members of the family support network and the target of the family support network and dates associated with the events of significance;
responsive to determining, by a coaching module operable within one or more computer systems of the communication service provider, a particular event among the events of significance is within a predetermined amount of time, the coaching module encouraging communications among the members of the family support network and the target of the family support network at least in part by causing a coaching message regarding the particular event to be delivered in hardcopy form to a hardcopy-based communication appliance associated with the family support network and used by the target of the family support network, the hardcopy-based communication appliance operable to both accept hardcopy input and produce hardcopy output, the coaching message including a suggestion regarding an appropriate digital gift that may be sent via the communication service provider by the target of the family support network to one or more members of the family support network, the coaching message including a form depicting representations of one or more images from which the target of the family support network may select to personalize the suggested digital gift; and
wherein the communication service dashboard module and the coaching module are implemented in one or more computer processors and one or more computer-readable storage media of the one or more computer systems, the one or more computer-readable storage media having instructions tangibly embodied therein representing the communication service dashboard module and the coaching module that are executable by the one or more computer processors.

16. The method of claim 15, wherein the particular event is a holiday celebrated by the members of the family support network.

17. The method of claim 15, wherein the particular event is a birthday or an anniversary of a member of the family support network.

18. The method of claim 15, wherein the form comprises an eCard order form which allows the target of the family support network to have delivered via email a personalized eCard by marking one or more selections regarding desired content on the eCard order form to create a filled-out eCard order form and returning the filled-out eCard order form to the communication service provider via the hardcopy-based communication appliance.

19. A method of facilitating caregroup coaching, the method comprising:
providing a communication service configured to facilitate and encourage communications among a plurality of members of a caregroup and a target of the caregroup, the target of the caregroup using a hardcopy-based communication appliance associated with the caregroup to transmit, based on hardcopy input, electronic communications to one or more of the plurality of the members of the caregroup via the communication service and output hardcopies of electronic communications received via the communication service from one or more of the plurality of members of the caregroup;

receiving, by a communication service dashboard module operable within a one or more computer systems of the communication service, information defining the caregroup, including the plurality of members of the caregroup, the target of the caregroup and one or more administrating caregivers of the caregroup;

capturing, by a monitoring module operable within the one or more computer systems, information regarding digital gifts exchanged among the plurality of members of the caregroup and the target of the caregroup via the communication service;

calculating, by the monitoring module, one or more metrics based on the captured information;

based on the one or more metrics, a coaching module operable within the one or more computer systems of the communication service automatically generating and delivering a coaching message to one or more members of the plurality of members of the caregroup, the coaching message including a suggestion regarding an appropriate digital gift to be sent to the hardcopy-based communication appliance of the target of the caregroup via the communication service; and wherein the communication service dashboard module, the monitoring module and the coaching module are implemented in one or more computer processors and one or more computer-readable storage media of the one or more computer systems, the one or more computer-readable storage media having instructions tangibly embodied therein representing the communication service dashboard module, the monitoring module and the coaching module that are executable by the one or more computer processors.

20. The method of claim 19, further comprising allowing, by the coaching module, the one or more administrating caregivers to send coaching messages to other members of the plurality of members of the caregroup.

21. The method of claim 20, wherein the coaching messages are directed to those of the other members of the plurality of members of the caregroup that have not tried a particular type of digital gift available via the communication service or not used the particular type of digital gift for a predetermined amount of time.

22. The method of claim 20, wherein the one or more metrics include one or more of:
- a rating regarding an affective-emotional value of digital gifts received by the target of the caregroup;
- a rating regarding an intellectual stimulus value of the digital gifts received by the target of the caregroup;
- a rating regarding activity induced value of the digital gifts received by the target of the caregroup; and
- information regarding historical norms of communications frequencies with the target of the caregroup by individual members of the plurality of members of the caregroup.

23. The method of claim 22, further comprising a communications dashboard module operable within a web server of the communication service facilitating member-to-member coaching by providing the one or more administrating caregivers with access to visual presentations or summaries of the one or more metrics.

24. The method of claim 20, further comprising the coaching module facilitating member-to-member coaching by suggesting appropriate coaching messages to be sent by the one or more administrating caregivers.

25. A method of facilitating two-way electronic communications between a member of a caregroup and a target of the caregroup, the method comprising:

receiving, by a communication service dashboard module operable within a web server of a communication service provider, information defining a caregroup, including members of the caregroup, a target of the caregroup and one or more administrating caregivers of the caregroup;

delivering, by a print job module operable within a distribution server of the communication service provider, an electronic communication originated by a member of the caregroup to the target of the caregroup that is associated with a hardcopy-based communication appliance by causing the hardcopy-based communication appliance to print a paper-based representation of the electronic communication, wherein the paper-based representation of the electronic communication includes thereon a set of identification marks that uniquely associate the paper-based representation with a record in a database of the distribution server containing an electronic mail (email) address of the member of the caregroup;

after said delivering, receiving, by a scan upload module operable within the distribution server from the hardcopy-based communication appliance, a digital representation of an explicit reply to the electronic communication as a result of hardcopy-based input provided to the hardcopy-based communication appliance in the form of an annotated version of the paper-based representation;

reading, by an automated dispatching module operable within the distribution server, the set of item identification marks from the digital representation of the annotated version of the paper-based representation;

determining, by the automated dispatching module, the email address of the member of the caregroup by retrieving the record from the database based upon a value represented by the set of item identification marks;

composing, by the automated dispatching module, a digital representation of a reply message based on annotations of the annotated version of the paper-based representation;

directly or indirectly distributing, by the automated dispatching module, the digital representation of the reply message to the member of the caregroup by associating the digital representation of the reply message with an email message addressed to the email address of the member of the caregroup; and wherein the communication service dashboard module, the print job module, the scan upload module and the automated dispatching module are implemented in one or more computer processors and one or more computer-readable storage media of the distribution server or the web server, the one or more computer-readable storage media having instructions tangibly embodied therein representing the communication service dashboard module, the print job module, the scan upload module and the automated dispatching module that are executable by the one or more computer processors.

26. The method of claim 25, wherein said directly or indirectly distributing, by the automated dispatching module, the digital representation of the reply message to the member of the caregroup comprises causing an email message to be delivered to the member of the caregroup, the email message containing a link to the digital representation of the reply message.

27. The method of claim 25, wherein said directly or indirectly distributing, by the automated dispatching module, the digital representation of the reply message to the member of the caregroup comprises causing an email message to be delivered to the member of the caregroup, the email message having embedded therein the digital representation of the reply message.

28. The method of claim 25, wherein said directly or indirectly distributing, by the automated dispatching module, the digital representation of the reply message to the member of the caregroup comprises causing an email message to be delivered to the member of the caregroup, the email message having attached thereto the digital representation of the reply message.

29. The method of claim 25, wherein the record also contains information indicative of a particular form type of a plurality of predetermined form types represented by the paper-based representation of the electronic communication.

30. The method of claim 25, wherein the set of item identification marks comprises one or more of a barcode and a semicode.

31. A program storage device readable by one or more computer systems of a communication service provider, tangibly embodying a program of instructions executable by the one or more computer systems to perform method steps for facilitating and encouraging communications among a plurality of members of a caregroup and a target of the caregroup, said method steps comprising:

receiving information defining the caregroup, including the plurality of members of the caregroup, the target of the caregroup and one or more administrating caregivers of the caregroup, wherein the target of the caregroup uses a hardcopy-based communication appliance associated with the caregroup to transmit, based on hardcopy input, electronic communications to one or more of the plurality of the members of the caregroup via the communication service provider and receive output hardcopies of electronic communications received via the communication service provider from one or more of the plurality of members of the caregroup;

capturing information regarding digital gifts exchanged among the plurality of members of the caregroup and the target of the caregroup via the communication service provider;

calculating one or more metrics based on the captured information; and based on the one or more metrics automatically generating and delivering a coaching message to one or more members of the plurality of members of the caregroup, the coaching message including a suggestion regarding an appropriate digital gift to be sent to the hardcopy-based communication appliance of the target of the caregroup via the communication service provider.

32. The program storage device of claim 31, wherein said method steps further comprise allowing the one or more administrating caregivers to send coaching messages to other members of the plurality of members of the caregroup.

33. The program storage device of claim 32, wherein the coaching messages are directed to those of the other members of the plurality of members of the caregroup that have not tried a particular type of digital gift available via the communication service provider or not used the particular type of digital gift for a predetermined amount of time.

34. The program storage device of claim 32, wherein the one or more metrics include one or more of:

a rating regarding an affective-emotional value of digital gifts received by the target of the caregroup;

a rating regarding an intellectual stimulus value of the digital gifts received by the target of the caregroup;

a rating regarding activity induced value of the digital gifts received by the target of the caregroup; and information regarding historical norms of communications frequencies with the target of the caregroup by individual members of the plurality of members of the caregroup.

35. The program storage device of claim 34, wherein said method steps further comprise facilitating member-to-member coaching by providing the one or more administrating caregivers with access to visual presentations or summaries of the one or more metrics.

36. The program storage device of claim 32, wherein said method steps further comprise facilitating member-to-member coaching by suggesting appropriate coaching messages to be sent by the one or more administrating caregivers.

37. A program storage device readable by one or more computer systems of a communication service provider, tangibly embodying a program of instructions executable by the one or more computer systems to perform method steps for facilitating two-way electronic communications between a member of a caregroup and a target of the caregroup, said method steps comprising:

receiving information defining the caregroup, including members of the caregroup, the target of the caregroup and one or more administrating caregivers of the caregroup;

delivering an electronic communication originated by a member of the caregroup to the target of the caregroup that is associated with a hardcopy-based communication appliance by causing the hardcopy-based communication appliance to print a paper-based representation of the electronic communication, wherein the paper-based representation of the electronic communication includes thereon a set of identification marks that uniquely associate the paper-based representation with a record in a database of the distribution server containing an electronic mail (email) address of the member of the caregroup;

after said delivering, receiving from the hardcopy-based communication appliance, a digital representation of an explicit reply to the electronic communication as a result of hardcopy-based input provided to the hardcopy-based communication appliance in the form of an annotated version of the paper-based representation;

reading the set of item identification marks from the digital representation of the annotated version of the paper-based representation;

determining the email address of the member of the caregroup by retrieving the record from the database based upon a value represented by the set of item identification marks;

composing a digital representation of a reply message based on annotations of the annotated version of the paper-based representation; and directly or indirectly distributing the digital representation of the reply message to the member of the caregroup by associating the digital representation of the reply message with an email message addressed to the email address of the member of the caregroup.

38. A program storage device readable by one or more computer systems of a communication service provider, tangibly embodying a program of instructions executable by the one or more computer systems to perform method steps for facilitating caregroup coaching, said method steps comprising:

receiving information defining a family support network, including members of the family support network, a target of the family support network and one or more administrating caregivers of the family support network, maintaining maintains information regarding events of significance to the members of the family support network and the target of the family support network and dates associated with the events of significance;

determining a particular event among the events of significance is within a predetermined amount of time; and responsive to said determining, encouraging communications among the members of the family support network and the target of the family support network at least in part by causing a coaching message regarding the particular event to be delivered in hardcopy form to a hardcopy-based communication appliance associated with the family support network and used by the target of the family support network, wherein the hardcopy-based communication appliance is operable to both accept hardcopy input and produce hardcopy output, the coaching message including a suggestion regarding an appropriate digital gift that may be sent via the communication service provider by the target of the family support network to one or more members of the family support network, the coaching message including a form depicting representations of one or more images from which the target of the family support network may select to personalize the suggested digital gift.

39. The program storage device of claim 38, wherein the particular event is a holiday celebrated by the members of the family support network.

40. The program storage device of claim 38, wherein the particular event is a birthday or an anniversary of a member of the family support network.

41. The program storage device of claim 38, wherein the form comprises an eCard order form which allows the target of the family support network to have delivered via email to one or more members of the family support network a personalized eCard by marking one or more selections regarding desired content on the eCard order form to create a filled-out eCard order form and returning the filled-out eCard order form to the communication service provider via the hardcopy-based communication appliance.

* * * * *